US011305004B2

United States Patent
He et al.

(10) Patent No.: US 11,305,004 B2
(45) Date of Patent: Apr. 19, 2022

(54) COMPOSITIONS AND METHODS RELATED TO EBOLAVIRUS VACCINES

(71) Applicant: The Scripps Research Institute, La Jolla, CA (US)

(72) Inventors: Linling He, San Diego, CA (US); Jiang Zhu, San Diego, CA (US); Anshul Chaudhary, La Jolla, CA (US); Ian Wilson, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 17/397,340

(22) Filed: Aug. 9, 2021

(65) Prior Publication Data

US 2022/0040286 A1    Feb. 10, 2022

Related U.S. Application Data

(60) Provisional application No. 63/063,530, filed on Aug. 10, 2020.

(51) Int. Cl.
*A61K 39/12* (2006.01)
*C12N 7/00* (2006.01)
*C07K 14/47* (2006.01)

(52) U.S. Cl.
CPC ............ *A61K 39/12* (2013.01); *C07K 14/473* (2013.01); *C12N 7/00* (2013.01); *C07K 2317/34* (2013.01); *C07K 2319/735* (2013.01); *C12N 2760/14134* (2013.01)

(58) Field of Classification Search
None
See application file for complete search history.

(56) References Cited

FOREIGN PATENT DOCUMENTS

WO    WO 2017/172622 A1 * 10/2017

OTHER PUBLICATIONS

Bornholdt et al., Host-Primed Ebola Virus GP Exposes a Hydrophobic NPC1 Receptor-Binding Pocket, Revealing a Target for Broadly Neutralizing Antibodies, American Society for Microbiology, Jan./Feb. 2013, pp. 1-11, vol. 7, Issue 1.
Gaudinski et al., Safety, Tolerability, Pharmacokinetics, and Immunogenicity of mAb114: A Phase 1 Trial of a Therapeutic Monoclonal Antibody Targeting Ebola Virus Glycoprotein, Lancet, Mar. 2, 2019, pp. 889-898.
Geisbert et al., Vesicular Stomatitis Virus-Based Ebola Vaccine Is Well-Tolerated and Protects Immunocompromised Nonhuman Primates, PLOS Pathogens, Nov. 2008, pp. 1-9, vol. 4, Issue 11.
Geisbert et al., Single-Injection Vaccine Protects Nonhuman Primates against Infection with Marburg Virus and Three Species of Ebola Virus, Journal of Virology, Jul. 2009, pp. 7296-7304, vol. 83, No. 14.
Gilchuk et al., Analysis of a Therapeutic Antibody Cocktail Reveals Determinants for Cooperative and Broad Ebolavirus Neutralization, Immunity, Feb. 18, 2020, pp. 388-403, vol. 52.
He et al., Presenting Native-like Trimeric HIV-1 Antigens with Self-Assembling Nanoparticles, Nature Communications, Jun. 28, 2016, pp. 1-15.
He et al., HIV-1 Vaccine Design Through Minimizing Envelope Metastability, Science Advances, Nov. 21, 2018, pp. 1-19.
Hsia et al., Design of a Hyperstable 60-subunit Protein Icosahedron, Nature, Jul. 7, 2016, pp. 136-139.
Jones et al., Live Attenuated Recombinant Vaccine Protects Nonhuman Primates Against Ebola and Marburg Viruses, Nature Medicine, Jul. 2005, pp. 786-790, vol. 11, No. 7.
Kennedy et al., Phase 2 Placebo-Controlled Trial of Two Vaccines to Prevent Ebola in Liberia, The New England Journal of Medicine, Oct. 12, 2017, pp. 1438 1447.
Kong et al., Uncleaved Prefusion-optimized gp140 Trimers Derived from Analysis of HIV-1 Envelope Metastability, Nature Communications, Jun. 28, 2016, pp. 1-15.
Marzi et al., Antibodies are Necessary for rVSV/ZEBOV-GP-mediated Protection Against Lethal Ebola Virus Challenge in Nonhuman Primates, PNAS, Jan. 29, 2013, pp. 1893-1898, vol. 110, No. 5.
Murin et al., Structures of Protective Antibodies Reveal Sites of Vulnerability on Ebola Virus, PNAS, Dec. 2, 2014, p. 17182-17187, vol. 111, No. 48.
Pallesen et al., Structures of Ebola Virus GP and sGP in Complex with Therapeutic Antibodies, Nat Microbiol., Feb. 8, 2016, pp. 1-23.
Oui et al., Mucosal Immunization of Cynomolgus Macaques with the VSVDG/ZEBOVGP Vaccine Stimulates Strong Ebola GP-Specific Immune Responses, PLOS One, May 2009, pp. 1-11, vol. 4, Issue 5.
Rutton et al., Structure-Based Design of Prefusion-Stabilized Filovirus Glycoprotein Trimers, Cell Reports, Mar. 31, 2020, pp. 4540-4550, vol. 30.
Zhu et al., Safety and Immunogenicity of a Recombinant Adenovirus Type-5 Vector-based Ebola Vaccine in Healthy Adults in Sierra Leone: a Single-centre, Randomised, Double-blind, Placebo-controlled, Phase 2 Trial, The Lancet, Feb. 11, 2017, pp. 621-628, vol. 389.

\* cited by examiner

*Primary Examiner* — Stacy B Chen
(74) *Attorney, Agent, or Firm* — Hugh Wang; Thomas Fitting

(57) ABSTRACT

The present invention provides novel engineered Ebolavirus GP proteins and polypeptides, as well as scaffolded vaccine compositions that display the engineered proteins. The invention also provides methods of using such engineered Ebolavirus GP proteins and vaccine compositions in various therapeutic applications, e.g., for preventing or treating Ebolavirus infections.

29 Claims, 14 Drawing Sheets

Specification includes a Sequence Listing.

FIG. 1

84.8% sequence conservation in HR1+HR2 across ebolavirus species

```
                                                    HR1
                                                       HR1c
                                           |----------------|----------->

Bundibugyo-ebolavirus      ████████LICGLRQLANETTQALQLFLRA████████ILNRKAIDFLLQR
Tai-Forest-ebolavirus      ████████LICGLRQLANETTQALQLFLRA████████ILNRKAIDFLLQR
Zaire-ebolavirus           ████████LICGLRQLANETTQALQLFLRA████████ILNRKAIDFLLQR
Reston-ebolavirus          ████████LICGLRQLANETTQALQLFLRA████████SLNRKAIDFLLQR
Sudan-ebolavirus           ████████LVCGLRQLANETTQALQLFLRA████████ILNRKAIDFLLRR
                           ████████ *.*********.***********    **********.*

Bundibugyo-ebolavirus      WGGTCHILGPDCCIEPHD█TKNITDKIDQIIHDFID████████
Tai-Forest-ebolavirus      WGGTCHILGPDCCIEPQD█TKNITDKIDQIIHDFVD████████
Zaire-ebolavirus           WGGTCHILGPDCCIEPHD█ITDKIDQIIHDFVD████tension████
Reston-ebolavirus          WGGTCRILGPSCCIEPHD█TKNITDEINQIKHDFID████████
Sudan-ebolavirus           WGGTCRILGPDCCIEPHD█TKNITDKINQIIHDFID████████
                           *****.****.******* .**** .*   **.*: *. * **
```

Dimeric locking domains (LD) for stabilizing the NP-forming interface

>LD1 1NI8_A (40aa after C-terminal deletion)
SEALKILNNIRTLRAQARECTLETLEEMLEKLEVVVNERREEESAA

>LD2 4AYA_B (44aa after N-/C-terminal deletion)
MNDCYSKLKELVPSIPQNKKVSKMEILQHVIDYILDLQIALDSH >LD3 1OVX_A (50aa after N-terminal deletion)
GHHHHHHTDKRKDGSGKLLYCSFCGKSQHEVRKLIAGPSVYICDECVDLCNDIIREEIKEVAPHRER >LD4 2MG4_A (58aa after N-terminal deletion)
MEKRPRTEFSEEQKKALDLAFYFDRRLTPEWRRYLSQRLGLNEEQIERWFRRKEQQIGWSHPQFEK >LD5 2JV7_A (78aa, without deletion)
DQPSVGDAFDKYNEAVRVFTQLSSAANCDWAACLSSLSASSAACIAAVGELGLDVPLDLACAATATSSATEACKGCLW >LD6 1JR5_A (88aa after N-terminal deletion)
MNKNIDTVREIITVASILIKFSREDIVENRANFIAFLNEIGVTHEGRKLNQNSFRKIVSELTQEDKKTLIDEFNEGFEGVYRYLEMYTNK >LD7 1PZQ_A (46aa after N-/C-terminal deletion)
GSAASPAVDIGDRLDELEKALEALSAEDGHDDVGQRLESLLRRWNSRRADAPSTSAISED

>LD8 1R2A_A (39aa after N-terminal deletion)
HMGHIQIPPGLTELLQGYTVEVLRQQPPDLVDFAVEYFTRLREARR >LD9 2JRX_A (65aa after N-/C-terminal deletion and glycan deletion)
MPQISRYSDEQVEQLLAELLNVLEKHKAPTDLSLMVLGNMVTNLINTAIAPAQRQAIANSFARALQSSINEDKAHLEHHHHHH

B

Antigenic evaluation of NPs presenting a stabilized GPΔmuc trimer

KZ52, c2G4, c4G7, mAb100, mAb114, c13C6, BDBV223, ADI-15878, ADI-15946, CA45

- GPΔmuc-WL²P²-foldon
- GPΔmuc-WL²P²-5GS-FR
- GPΔmuc-WL²P²-E2p-L4P
- GPΔmuc-WL²P²-10GS-I3-01-L7P

C

EC$_{50}$ values of EBOV GPΔmuc trimer and nanoparticles binding to 10 antibodies [a].

|  | KZ52 | c2G4 | c4G7 | mAb100 | mAb114 | c13C6 | BDBV223 | ADI-15878 | ADI-15946 | CA45 |
|---|---|---|---|---|---|---|---|---|---|---|
| GPΔmuc-WL²P²-foldon | 0.00626 | 0.009672 | 0.01087 | 0.007854 | 0.007466 | 0.007691 | 0.006012 | 0.009685 | 0.01087 | 0.01248 |
| GPΔmuc-WL²P²-5GS-FR | 0.006621 | 0.01025 | 0.009148 | 0.008558 | 0.005154 | 0.004143 | 0.01762 | 0.009293 | 0.005012 | 0.03987 |
| GPΔmuc-WL²P²-E2p-L4P | 0.006684 | 0.01345 | 0.009341 | 0.007583 | 0.004013 | 0.003659 | 0.01308 | 0.0116 | 0.005695 | 0.01685 |
| GPΔmuc-WL²P²-10GS-I3-01-L7P | 0.01321 | 0.02416 | 0.0226 | 0.00991 | 0.004625 | 0.007286 | 0.01489 | 0.06458 | 0.009234 | 0.04948 |

[a] EC$_{50}$ values were calculated from the besting fitting in GraphPad Prism 8.4.3.

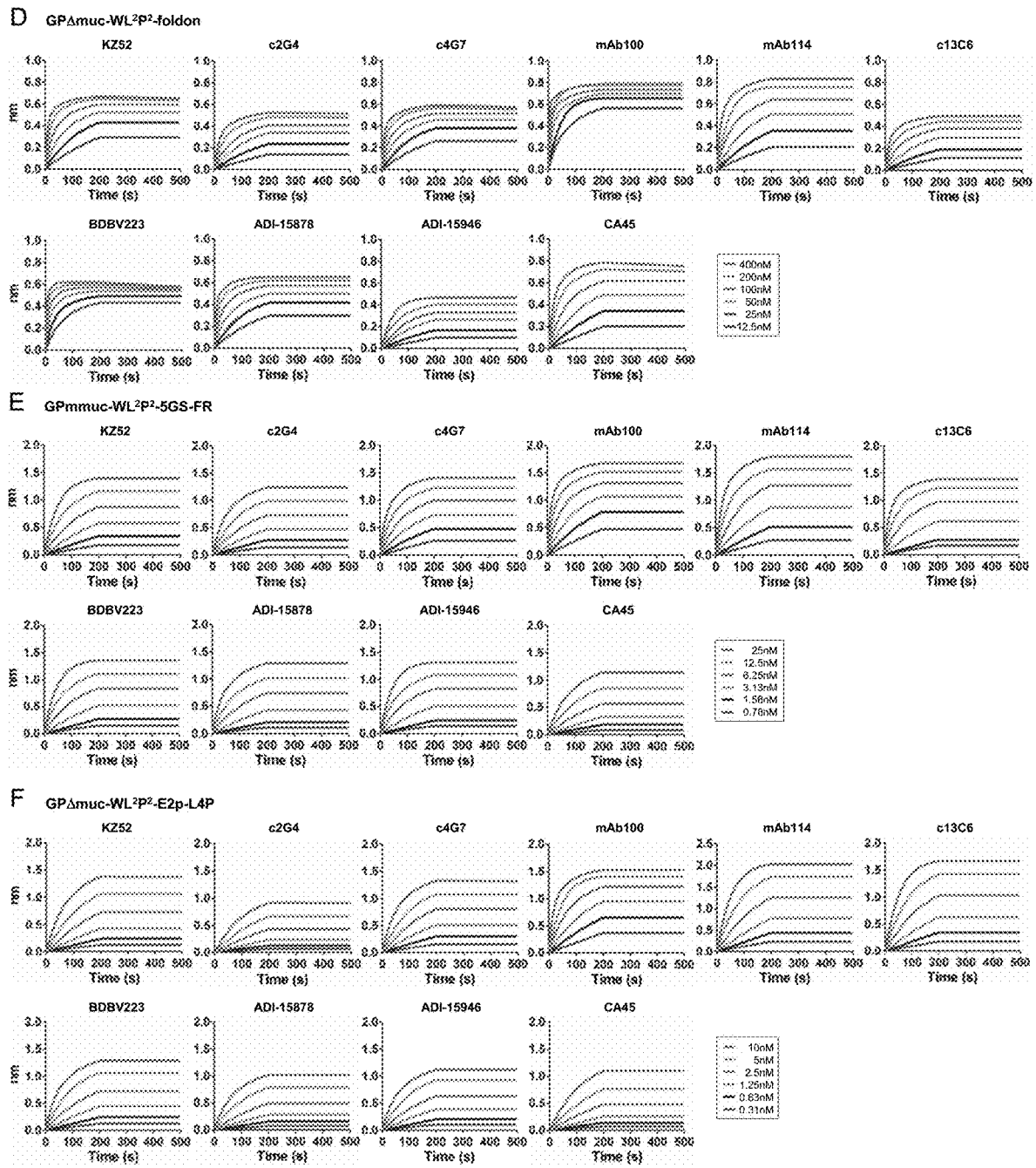
FIG. 4–cont.

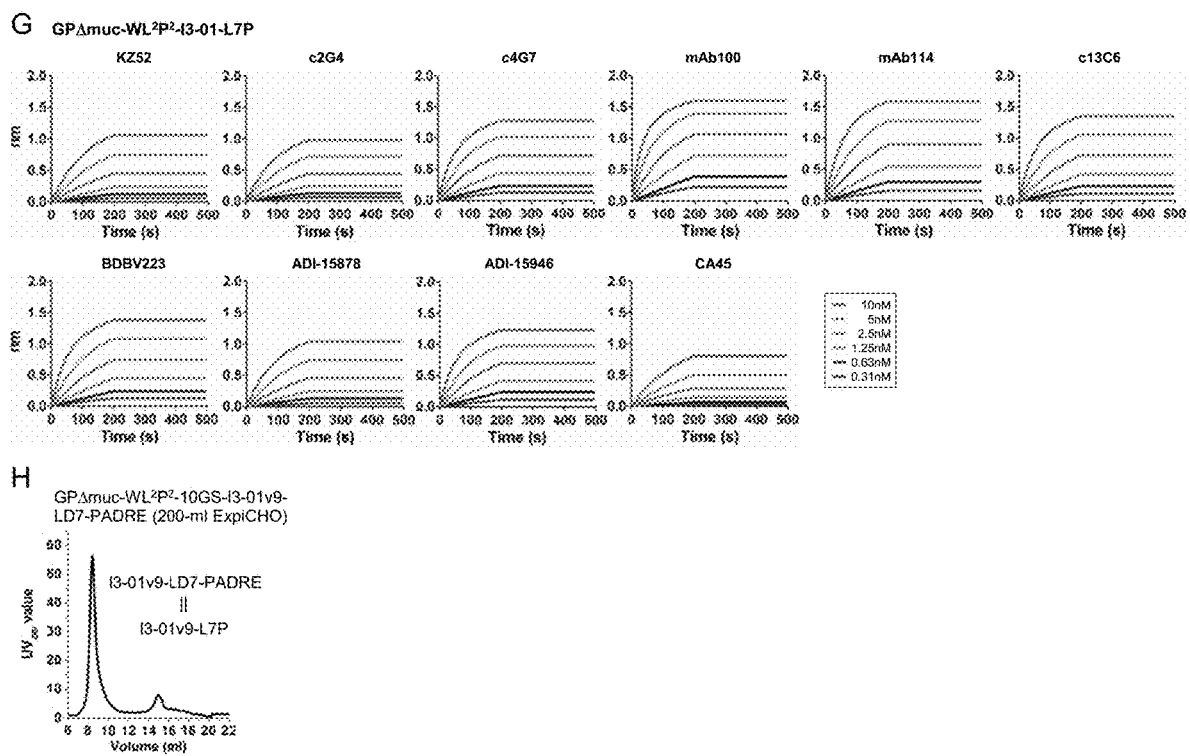
FIG. 4-cont.

FIG. 5

A  Serum antibody response during mouse immunization with GPΔMuc trimers and nanoparticles Rows (top to bottom): WT GP-foldon; WT GPΔMuc-foldon; GPΔMuc-WL²P²-foldon; GPΔMuc-WL²P²-5GS-FR; GPΔMuc-WL²P²-E2p-L4P; GPΔMuc-WL²P²-10GS-I3-01-L7P Columns: W2, W5, W8, W11

Right labels: WT GP trimer; WT GPΔMuc trimer; GPΔMuc-WL²P² trimer; GPΔMuc-WL²P²-based nanoparticles Legend: M1, M2, M3, M4, M5, M6, M7, M8

B $EC_{50}$ titers (fold of dilution) of mouse sera binding to EBOV GP trimers[a]

| | W2 | | | W5 | | | W8 | | | W11 | | |
|---|---|---|---|---|---|---|---|---|---|---|---|---|
| | WT GP-Foldon | WT GPΔMuc-foldon | GPΔMuc-WL²P²-foldon | WT GP-Foldon | WT GPΔMuc-foldon | GPΔMuc-WL²P²-foldon | WT GP-Foldon | WT GPΔMuc-foldon | GPΔMuc-WL²P²-foldon | WT GP-Foldon | WT GPΔMuc-foldon | GPΔMuc-WL²P²-foldon |
| M1 | 0.2454 | 71.1 | 92.87 | 606.5 | 8377 | 10280 | 10740 | 32034 | 18532 | 10467 | 56041 | 36300 |
| M2 | 21.07 | 118.6 | 13.88 | 4050 | 5879 | 3894 | 3663 | 40677 | 20082 | 20353 | 83513 | 28303 |
| M3 | 4.523 | -- | 67.15 | 376.3 | -- | 4851 | 3323 | -- | 14595 | 16418 | -- | 37914 |
| M4 | 1.434 | 16.29 | 30.62 | 1183 | 2755 | 8470 | 4338 | 10690 | 19570 | 11262 | 37135 | 49211 |
| M5 | 2.982 | 88.95 | 186.9 | 289 | 15768 | 8994 | 2382 | 35240 | 22712 | 16546 | 56785 | 46695 |
| M6 | 20.05 | 30.65 | 127 | 1804 | 2752 | 8816 | 5651 | 9447 | 35455 | 18888 | 16351 | 64055 |
| M7 | 5.3 | 6.727 | -- | 739.7 | 6293 | -- | 5066 | 33547 | -- | 26293 | 42415 | -- |
| M8 | 11.84 | 45.82 | 30.65 | 1449 | 1591 | 7248 | 17622 | 56265 | 25518 | 20626 | 117745 | 33217 |

[a] The $EC_{50}$ values were calculated from the besting fitting in GraphPad Prism 8.

EC$_{50}$ titers (fold of dilution) of mouse sera binding to EBOV GPΔMuc-WL$^2$P$^2$-presenting nanoparticles [a]

| | | W2 | | | W5 | | | W8 | | | W11 | |
|---|---|---|---|---|---|---|---|---|---|---|---|---|
| | GPΔMuc-WL$^2$P$^2$-5GS-FR | GPΔMuc-WL$^2$P$^2$-E2p-L4P | GPΔMuc-WL$^2$P$^2$-10GS-I3-01-L7P | GPΔMuc-WL$^2$P$^2$-5GS-FR | GPΔMuc-WL$^2$P$^2$-E2p-L4P | GPΔMuc-WL$^2$P$^2$-10GS-I3-01-L7P | GPΔMuc-WL$^2$P$^2$-5GS-FR | GPΔMuc-WL$^2$P$^2$-E2p-L4P | GPΔMuc-WL$^2$P$^2$-10GS-I3-01-L7P | GPΔMuc-WL$^2$P$^2$-5GS-FR | GPΔMuc-WL$^2$P$^2$-E2p-L4P | GPΔMuc-WL$^2$P$^2$-10GS-I3-01-L7P |
| M1 | 152.9 | 172.3 | 147.5 | 2367 | 4154 | 4389 | 9932 | 11715 | 7637 | 24325 | 17631 | 13984 |
| M2 | 146.4 | 112.1 | 40.52 | 3115 | 2559 | 5927 | 10324 | 12871 | 11689 | 22640 | 11150 | 34464 |
| M3 | 101.6 | 85.93 | 115.2 | 1691 | 4077 | 7196 | 4239 | 8701 | 14184 | 10166 | 15309 | 26621 |
| M4 | 158.5 | 121 | 158.9 | 2053 | 3426 | 4860 | 7750 | 6774 | 16144 | 23135 | 18605 | 18439 |
| M5 | 99.49 | 105.6 | 164.8 | 3598 | 692.1 | 8006 | 6227 | 9166 | 19698 | 38846 | 13793 | 19315 |
| M6 | 83.85 | 104.8 | 66.92 | 4238 | 2973 | 5440 | 17428 | 12140 | 10331 | | 24189 | 17649 |
| M7 | 100.8 | 142.3 | 305 | 9029 | 3443 | 3872 | 20184 | 10342 | 11975 | 34598 | 15778 | 21201 |
| M8 | 103.8 | 178 | 93.03 | 725.6 | 3022 | 15325 | 11421 | 7550 | 16234 | 13170 | 11012 | 37636 |

[a] The EC$_{50}$ values were calculated from the besting fitting in GraphPad Prism 8.

D Control antibody neutralization of EBOV-Makona in TZM-bl cells

E Control antibody neutralization of MLV in 293T cells

F Mouse serum IgG neutralization of MLV in 293T cells

FIG. 6

A Serum antibody response during rabbit immunization with GPΔMuc trimers and nanoparticles

B

EC$_{50}$ titers (fold of dilution) of rabbit sera binding to EBOV GP trimers[a]

| | W2 | | W5 | | W8 | | W11 | | W13 | |
|---|---|---|---|---|---|---|---|---|---|---|
| | WT GPΔMuc-foldon | GPΔMuc-WL²P²-foldon | WT GPΔMuc-foldon | GPΔMuc-WL²P²-foldon | WT GPΔMuc-foldon | GPΔMuc-WL²P²-foldon | WT GPΔMuc-foldon | GPΔMuc-WL²P²-foldon | WT GPΔMuc-foldon | GPΔMuc-WL²P²-foldon |
| M1 | 464.2 | 2428 | 9404 | 35115 | 13868 | 10110 | 18135 | 16116 | 12777 | 13338 |
| M2 | 455.9 | 1044 | 8904 | 26144 | 4647 | 12073 | 4446 | 8694 | 3143 | 5177 |
| M3 | 701.1 | 378 | 8943 | 13273 | 12652 | 8363 | 9807 | 6517 | 6681 | 3586 |
| M4 | 56.68 | 336.2 | 2392 | 18008 | 2220 | 6092 | 2663 | 6901 | 1443 | 3424 |

[a] The EC$_{50}$ values were calculated from the besting fitting in GraphPad Prism 8.4.3.

EC$_{50}$ titers (fold of dilution) of mouse sera binding to EBOV WT GPΔMuc-presenting nanoparticles [a]

| | W2 | | | W5 | | | W8 | | | W11 | | |
|---|---|---|---|---|---|---|---|---|---|---|---|---|
| | WT GPΔMuc-5GS-FR | WT GPΔMuc-E2p-L4P | WT GPΔMuc-10GS-I3-01-L7P | WT GPΔMuc-5GS-FR | WT GPΔMuc-E2p-L4P | WT GPΔMuc-10GS-I3-01-L7P | WT GPΔMuc-5GS-FR | WT GPΔMuc-E2p-L4P | WT GPΔMuc-10GS-I3-01-L7P | WT GPΔMuc-5GS-FR | WT GPΔMuc-E2p-L4P | WT GPΔMuc-10GS-I3-01-L7P |
| M1 | 392.7 | 133.3 | 404.2 | 9406 | 14736 | 21261 | 12961 | 11405 | 32895 | 9041 | 8972 | 26363 |
| M2 | 116.9 | 734.7 | 1207 | 20093 | 23950 | 44607 | 12927 | 15609 | 45311 | 8893 | 16560 | 31073 |
| M3 | 120 | 201.1 | 1774 | 18894 | 19727 | 41440 | 12770 | 12457 | 47664 | 8644 | 9954 | 28526 |
| M4 | 368.2 | 1126 | 1382 | 16116 | 34695 | 27118 | 13140 | 22771 | 32291 | 10558 | 16803 | 25205 |

| | W13 | | |
|---|---|---|---|
| | WT GPΔMuc-5GS-FR | WT GPΔMuc-E2p-L4P | WT GPΔMuc-10GS-I3-01-L7P |
| M1 | 5272 | 5795 | 16907 |
| M2 | 6817 | 12387 | 18398 |
| M3 | 4146 | 4889 | 16645 |
| M4 | 5047 | 8066 | 18753 |

The EC$_{50}$ values were calculated from the besting fitting in GraphPad Prism 8.4.3.

E  Ebolavirus-pp neutralization by purified rabbit IgG at the 3rd time point (w5)

BDBV

MLV-pp neutralization by purified rabbit IgG at the first time point (w5)

Sign of ADE

F  Ebolavirus-pp neutralization by purified rabbit IgG at the 4th time point (w8)

EBOV-Makona

BDBV

MLV-pp neutralization by purified rabbit IgG at the first time point (w8)

Sign of ADE

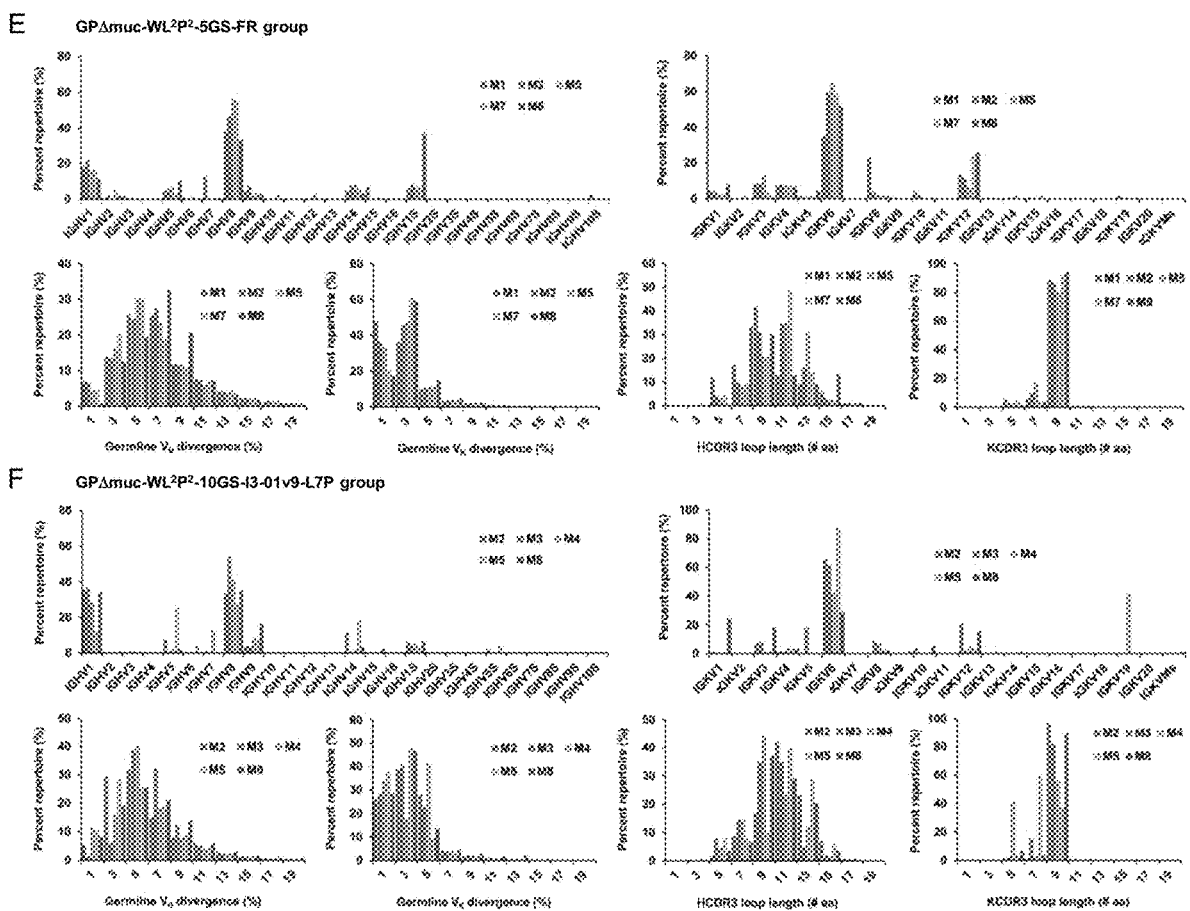
FIG. 7-cont.

ns in HR1. In some embodiments,

```
                           SEQUENCE LISTING

<160> NUMBER OF SEQ ID NOS: 62

<210> SEQ ID NO 1
<211> LENGTH: 676
<212> TYPE: PRT
<213> ORGANISM: Ebola virus

<400> SEQUENCE: 1

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
            35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
                325                 330                 335
```

Glu Asp His Lys Ile Met Ala Ser Glu Asn Ser Ser Ala Met Val Gln
                340                 345                 350

Val His Ser Gln Gly Arg Glu Ala Val Ser His Leu Thr Thr Leu
        355                 360                 365

Ala Thr Ile Ser Thr Ser Pro Gln Ser Leu Thr Thr Lys Pro Gly Pro
    370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
                405                 410                 415

Ala Ser Asp Thr Pro Ser Ala Thr Thr Ala Ala Gly Pro Pro Lys Ala
            420                 425                 430

Glu Asn Thr Asn Thr Ser Lys Ser Thr Asp Phe Leu Asp Pro Ala Thr
        435                 440                 445

Thr Thr Ser Pro Gln Asn His Ser Glu Thr Ala Gly Asn Asn Asn Thr
    450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Ile
    530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
        675

<210> SEQ ID NO 2
<211> LENGTH: 896
<212> TYPE: PRT
<213> ORGANISM: Artificial sequence
<220> FEATURE:
<223> OTHER INFORMATION: Synthetic sequence

<400> SEQUENCE: 2

Pro Leu Gly Val Ile His Asn Ser Thr Leu Gln Val Ser Asp Val Asp
1               5                   10                  15

```
Lys Leu Val Cys Arg Asp Lys Leu Ser Ser Thr Asn Gln Leu Arg Ser
             20                  25                  30

Val Gly Leu Asn Leu Glu Gly Asn Gly Val Ala Thr Asp Val Pro Ser
         35                  40                  45

Ala Thr Lys Arg Trp Gly Phe Arg Ser Gly Val Pro Pro Lys Val Val
 50                  55                  60

Asn Tyr Glu Ala Gly Glu Trp Ala Glu Asn Cys Tyr Asn Leu Glu Ile
 65                  70                  75                  80

Lys Lys Pro Asp Gly Ser Glu Cys Leu Pro Ala Ala Pro Asp Gly Ile
                 85                  90                  95

Arg Gly Phe Pro Arg Cys Arg Tyr Val His Lys Val Ser Gly Thr Gly
                100                 105                 110

Pro Cys Ala Gly Asp Phe Ala Phe His Lys Glu Gly Ala Phe Phe Leu
         115                 120                 125

Tyr Asp Arg Leu Ala Ser Thr Val Ile Tyr Arg Gly Thr Thr Phe Ala
130                 135                 140

Glu Gly Val Val Ala Phe Leu Ile Leu Pro Gln Ala Lys Lys Asp Phe
145                 150                 155                 160

Phe Ser Ser His Pro Leu Arg Glu Pro Val Asn Ala Thr Glu Asp Pro
                165                 170                 175

Ser Ser Gly Tyr Tyr Ser Thr Thr Ile Arg Tyr Gln Ala Thr Gly Phe
                180                 185                 190

Gly Thr Asn Glu Thr Glu Tyr Leu Phe Glu Val Asp Asn Leu Thr Tyr
         195                 200                 205

Val Gln Leu Glu Ser Arg Phe Thr Pro Gln Phe Leu Leu Gln Leu Asn
         210                 215                 220

Glu Thr Ile Tyr Thr Ser Gly Lys Arg Ser Asn Thr Thr Gly Lys Leu
225                 230                 235                 240

Ile Trp Lys Val Asn Pro Glu Ile Asp Thr Thr Ile Gly Glu Trp Ala
                245                 250                 255

Phe Trp Glu Thr Lys Lys Asn Leu Thr Arg Lys Ile Arg Ser Glu Glu
                260                 265                 270

Leu Ser Phe Thr Val Val Ser Thr His His Gln Asp Thr Gly Glu Glu
         275                 280                 285

Ser Ala Ser Ser Gly Lys Leu Gly Leu Ile Thr Asn Thr Ile Ala Gly
290                 295                 300

Val Ala Gly Leu Ile Thr Gly Gly Arg Arg Thr Arg Arg Glu Ala Ile
305                 310                 315                 320

Val Asn Ala Gln Pro Lys Cys Asn Pro Asn Leu His Tyr Trp Thr Thr
                325                 330                 335

Gln Asp Glu Gly Ala Ala Ile Gly Leu Ala Trp Ile Pro Tyr Phe Gly
         340                 345                 350

Pro Ala Ala Glu Gly Ile Tyr Ile Glu Gly Leu Met His Asn Gln Asp
         355                 360                 365

Gly Leu Ile Cys Gly Leu Arg Gln Leu Ala Asn Glu Thr Thr Gln Ala
         370                 375                 380

Leu Gln Leu Phe Leu Arg Ala Thr Thr Glu Leu Arg Thr Phe Ser Ile
385                 390                 395                 400

Leu Asn Arg Lys Ala Ile Asp Phe Leu Leu Gln Arg Trp Gly Gly Thr
                405                 410                 415

Cys His Ile Leu Gly Pro Asp Cys Cys Ile Glu Pro His Asp Trp Thr
                420                 425                 430
```

```
Lys Asn Ile Thr Asp Lys Ile Asp Gln Ile Ile His Asp Phe Val Asp
            435                 440                 445

Pro Leu Gly Val Ile His Asn Ser Thr Leu Gln Val Ser Asp Val Asp
        450                 455                 460

Lys Leu Val Cys Arg Asp Lys Leu Ser Ser Thr Asn Gln Leu Arg Ser
465                 470                 475                 480

Val Gly Leu Asn Leu Glu Gly Asn Gly Val Ala Thr Asp Val Pro Ser
                485                 490                 495

Ala Thr Lys Arg Trp Gly Phe Arg Ser Gly Val Pro Lys Val Val
                500                 505                 510

Asn Tyr Glu Ala Gly Glu Trp Ala Glu Asn Cys Tyr Asn Leu Glu Ile
            515                 520                 525

Lys Lys Pro Asp Gly Ser Glu Cys Leu Pro Ala Ala Pro Asp Gly Ile
        530                 535                 540

Arg Gly Phe Pro Arg Cys Arg Tyr Val His Lys Val Ser Gly Thr Gly
545                 550                 555                 560

Pro Cys Ala Gly Asp Phe Ala Phe His Lys Glu Gly Ala Phe Phe Leu
                565                 570                 575

Tyr Asp Arg Leu Ala Ser Thr Val Ile Tyr Arg Gly Thr Thr Phe Ala
            580                 585                 590

Glu Gly Val Val Ala Phe Leu Ile Leu Pro Gln Ala Lys Lys Asp Phe
        595                 600                 605

Phe Ser Ser His Pro Leu Arg Glu Pro Val Asn Ala Thr Glu Asp Pro
610                 615                 620

Ser Ser Gly Tyr Tyr Ser Thr Thr Ile Arg Tyr Gln Ala Thr Gly Phe
625                 630                 635                 640

Gly Thr Asn Glu Thr Glu Tyr Leu Phe Glu Val Asp Asn Leu Thr Tyr
                645                 650                 655

Val Gln Leu Glu Ser Arg Phe Thr Pro Gln Phe Leu Leu Gln Leu Asn
            660                 665                 670

Glu Thr Ile Tyr Thr Ser Gly Lys Arg Ser Asn Thr Thr Gly Lys Leu
        675                 680                 685

Ile Trp Lys Val Asn Pro Glu Ile Asp Thr Thr Ile Gly Glu Trp Ala
690                 695                 700

Phe Trp Glu Thr Lys Lys Asn Leu Thr Arg Lys Ile Arg Ser Glu Glu
705                 710                 715                 720

Leu Ser Phe Thr Val Val Ser Thr His His Gln Asp Thr Gly Glu Glu
                725                 730                 735

Ser Ala Ser Ser Gly Lys Leu Gly Leu Ile Thr Asn Thr Ile Ala Gly
            740                 745                 750

Val Ala Gly Leu Ile Thr Gly Gly Arg Arg Thr Arg Arg Glu Ala Ile
        755                 760                 765

Val Asn Ala Gln Pro Lys Cys Asn Pro Asn Leu His Tyr Trp Thr Thr
770                 775                 780

Gln Asp Glu Gly Ala Ala Ile Gly Leu Ala Trp Ile Pro Tyr Phe Gly
785                 790                 795                 800

Pro Ala Ala Glu Gly Ile Tyr Ile Glu Gly Leu Met His Asn Gln Asp
                805                 810                 815

Gly Leu Ile Cys Gly Leu Arg Gln Leu Ala Asn Glu Thr Thr Gln Ala
            820                 825                 830

Leu Gln Leu Phe Leu Arg Ala Thr Thr Glu Leu Arg Thr Phe Ser Ile
        835                 840                 845

Leu Asn Arg Lys Ala Ile Asp Phe Leu Leu Gln Arg Trp Gly Gly Thr
```

```
                850              855              860
Cys His Ile Leu Gly Pro Asp Cys Cys Ile Glu Pro His Asp Trp Thr
865              870              875              880

Lys Asn Ile Thr Asp Lys Ile Asp Gln Ile Ile His Asp Phe Val Asp
                885              890              895

<210> SEQ ID NO 3
<211> LENGTH: 448
<212> TYPE: PRT
<213> ORGANISM: Artificial sequence
<220> FEATURE:
<223> OTHER INFORMATION: Synthetic sequence

<400> SEQUENCE: 3

Pro Leu Gly Val Ile His Asn Ser Ala Leu Gln Val Ser Asp Val Asp
1               5                  10                  15

Lys Leu Val Cys Arg Asp Lys Leu Ser Ser Thr Asn Gln Leu Arg Ser
                20                  25                  30

Val Gly Leu Asn Leu Glu Gly Asn Gly Val Ala Thr Asp Val Pro Ser
            35                  40                  45

Ala Thr Lys Arg Trp Gly Phe Arg Ser Gly Val Pro Pro Lys Val Val
50                  55                  60

Asn Tyr Glu Ala Gly Glu Trp Ala Glu Asn Cys Tyr Asn Leu Glu Ile
65                  70                  75                  80

Lys Lys Pro Asp Gly Ser Glu Cys Leu Pro Ala Ala Pro Asp Gly Ile
                85                  90                  95

Arg Gly Phe Pro Arg Cys Arg Tyr Val His Lys Val Ser Gly Thr Gly
                100                 105                 110

Pro Cys Ala Gly Asp Phe Ala Phe His Lys Glu Gly Ala Phe Phe Leu
            115                 120                 125

Tyr Asp Arg Leu Ala Ser Thr Val Ile Tyr Arg Gly Thr Thr Phe Ala
130                 135                 140

Glu Gly Val Val Ala Phe Leu Ile Leu Pro Gln Ala Lys Lys Asp Phe
145                 150                 155                 160

Phe Ser Ser His Pro Leu Arg Glu Pro Val Asn Ala Thr Glu Asp Pro
                165                 170                 175

Ser Ser Gly Tyr Tyr Ser Thr Thr Ile Arg Tyr Gln Ala Thr Gly Phe
            180                 185                 190

Gly Thr Asn Glu Thr Glu Tyr Leu Phe Glu Val Asp Asn Leu Thr Tyr
        195                 200                 205

Val Gln Leu Glu Ser Arg Phe Thr Pro Gln Phe Leu Leu Gln Leu Asn
210                 215                 220

Glu Thr Ile Tyr Thr Ser Gly Lys Arg Ser Asn Thr Thr Gly Lys Leu
225                 230                 235                 240

Ile Trp Lys Val Asn Pro Glu Ile Asp Thr Thr Ile Gly Glu Trp Ala
                245                 250                 255

Phe Trp Glu Thr Lys Lys Asn Leu Thr Arg Lys Ile Arg Ser Glu Glu
            260                 265                 270

Leu Ser Phe Thr Val Val Ser Thr His His Gln Asp Thr Gly Glu Glu
        275                 280                 285

Ser Ala Ser Ser Gly Lys Leu Gly Leu Ile Thr Asn Thr Ile Ala Gly
    290                 295                 300

Val Ala Gly Leu Ile Thr Gly Gly Arg Arg Thr Arg Arg Glu Ala Ile
305                 310                 315                 320

Val Asn Ala Gln Pro Lys Cys Asn Pro Asn Leu His Tyr Trp Thr Thr
```

```
                    325                 330                 335
Gln Asp Glu Gly Ala Ala Ile Gly Leu Ala Trp Ile Pro Tyr Phe Gly
                340                 345                 350

Pro Ala Ala Glu Gly Ile Tyr Ile Glu Gly Leu Met His Asn Gln Asp
            355                 360                 365

Gly Leu Ile Cys Gly Leu Arg Gln Leu Ala Asn Glu Thr Thr Gln Ala
        370                 375                 380

Leu Gln Leu Phe Leu Arg Ala Thr Thr Glu Leu Arg Thr Phe Ser Ile
385                 390                 395                 400

Leu Asn Arg Lys Ala Ile Asp Phe Leu Leu Gln Arg Trp Gly Gly Thr
                405                 410                 415

Cys His Ile Leu Gly Pro Asp Cys Cys Ile Glu Pro His Asp Trp Thr
                420                 425                 430

Lys Asn Ile Thr Asp Lys Ile Asp Gln Ile Ile His Asp Phe Val Asp
                435                 440                 445

<210> SEQ ID NO 4
<211> LENGTH: 448
<212> TYPE: PRT
<213> ORGANISM: Artificial sequence
<220> FEATURE:
<223> OTHER INFORMATION: Synthetic sequence

<400> SEQUENCE: 4

Pro Leu Gly Val Ile His Asn Ser Ala Leu Gln Val Ser Asp Val Asp
1               5                   10                  15

Lys Leu Val Cys Arg Asp Lys Leu Ser Ser Thr Asn Gln Leu Arg Ser
                20                  25                  30

Val Gly Leu Asn Leu Glu Gly Asn Gly Val Ala Thr Asp Val Pro Ser
            35                  40                  45

Ala Thr Lys Arg Trp Gly Phe Arg Ser Gly Val Pro Pro Lys Val Val
        50                  55                  60

Asn Tyr Glu Ala Gly Glu Trp Ala Glu Asn Cys Tyr Asn Leu Glu Ile
65                  70                  75                  80

Lys Lys Pro Asp Gly Ser Glu Cys Leu Pro Ala Ala Pro Asp Gly Ile
                85                  90                  95

Arg Gly Phe Pro Arg Cys Arg Tyr Val His Lys Val Ser Gly Thr Gly
                100                 105                 110

Pro Cys Ala Gly Asp Phe Ala Phe His Lys Glu Gly Ala Phe Phe Leu
            115                 120                 125

Tyr Asp Arg Leu Ala Ser Thr Val Ile Tyr Arg Gly Thr Thr Phe Ala
        130                 135                 140

Glu Gly Val Val Ala Phe Leu Ile Leu Pro Gln Ala Lys Lys Asp Phe
145                 150                 155                 160

Phe Ser Ser His Pro Leu Arg Glu Pro Val Asn Ala Thr Glu Asp Pro
                165                 170                 175

Ser Ser Gly Tyr Tyr Ser Thr Thr Ile Arg Tyr Gln Ala Thr Gly Phe
            180                 185                 190

Gly Thr Asn Glu Thr Glu Tyr Leu Phe Glu Val Asp Asn Leu Thr Tyr
        195                 200                 205

Val Gln Leu Glu Ser Arg Phe Thr Pro Gln Phe Leu Leu Gln Leu Asn
        210                 215                 220

Glu Thr Ile Tyr Thr Ser Gly Lys Arg Ser Asn Thr Thr Gly Lys Leu
225                 230                 235                 240

Ile Trp Lys Val Asn Pro Glu Ile Asp Thr Thr Ile Gly Glu Trp Ala
```

```
                  245                 250                 255
Phe Trp Glu Thr Lys Asn Leu Thr Arg Lys Ile Arg Ser Glu Glu
            260                 265                 270

Leu Ser Phe Thr Val Val Ser Thr His His Gln Asp Thr Gly Glu Glu
            275                 280                 285

Ser Ala Ser Ser Gly Lys Leu Gly Leu Ile Thr Asn Thr Ile Ala Gly
            290                 295                 300

Val Ala Gly Leu Ile Thr Gly Gly Arg Arg Thr Arg Arg Glu Ala Ile
305                 310                 315                 320

Val Asn Ala Gln Pro Lys Cys Asn Pro Asn Leu His Tyr Trp Thr Thr
                325                 330                 335

Gln Asp Glu Gly Ala Ala Ile Gly Leu Ala Trp Ile Pro Tyr Phe Gly
            340                 345                 350

Pro Ala Ala Glu Gly Ile Tyr Ile Glu Gly Leu Met His Asn Gln Asp
            355                 360                 365

Gly Leu Ile Cys Gly Leu Arg Gln Leu Ala Asn Glu Thr Thr Gln Ala
    370                 375                 380

Leu Gln Leu Phe Leu Arg Ala Thr Thr Glu Leu Arg Thr Phe Ser Ile
385                 390                 395                 400

Leu Asn Arg Lys Ala Ile Asp Phe Leu Leu Gln Arg Trp Gly Gly Thr
                405                 410                 415

Cys His Ile Leu Gly Pro Asp Cys Cys Ile Glu Pro His Asp Leu Thr
            420                 425                 430

Lys Asn Ile Thr Asp Lys Ile Asp Gln Ile Ile His Asp Phe Val Asp
            435                 440                 445

<210> SEQ ID NO 5
<211> LENGTH: 463
<212> TYPE: PRT
<213> ORGANISM: Artificial sequence
<220> FEATURE:
<223> OTHER INFORMATION: Synthetic sequence

<400> SEQUENCE: 5

Pro Leu Gly Val Ile His Asn Ser Ala Leu Gln Val Ser Asp Val Asp
1               5                   10                  15

Lys Leu Val Cys Arg Asp Lys Leu Ser Ser Thr Asn Gln Leu Arg Ser
            20                  25                  30

Val Gly Leu Asn Leu Glu Gly Asn Gly Val Ala Thr Asp Val Pro Ser
        35                  40                  45

Ala Thr Lys Arg Trp Gly Phe Arg Ser Gly Val Pro Pro Lys Val Val
50                  55                  60

Asn Tyr Glu Ala Gly Glu Trp Ala Glu Asn Cys Tyr Asn Leu Glu Ile
65                  70                  75                  80

Lys Lys Pro Asp Gly Ser Glu Cys Leu Pro Ala Ala Pro Asp Gly Ile
                85                  90                  95

Arg Gly Phe Pro Arg Cys Arg Tyr Val His Lys Val Ser Gly Thr Gly
            100                 105                 110

Pro Cys Ala Gly Asp Phe Ala Phe His Lys Glu Gly Ala Phe Phe Leu
        115                 120                 125

Tyr Asp Arg Leu Ala Ser Thr Val Ile Tyr Arg Gly Thr Thr Phe Ala
    130                 135                 140

Glu Gly Val Val Ala Phe Leu Ile Leu Pro Gln Ala Lys Lys Asp Phe
145                 150                 155                 160

Phe Ser Ser His Pro Leu Arg Glu Pro Val Asn Ala Thr Glu Asp Pro
```

```
                165                 170                 175
Ser Ser Gly Tyr Tyr Ser Thr Thr Ile Arg Tyr Gln Ala Thr Gly Phe
                180                 185                 190

Gly Thr Asn Glu Thr Glu Tyr Leu Phe Glu Val Asp Asn Leu Thr Tyr
                195                 200                 205

Val Gln Leu Glu Ser Arg Phe Thr Pro Gln Phe Leu Leu Gln Leu Asn
210                 215                 220

Glu Thr Ile Tyr Thr Ser Gly Lys Arg Ser Asn Thr Thr Gly Lys Leu
225                 230                 235                 240

Ile Trp Lys Val Asn Pro Glu Ile Asp Thr Thr Ile Gly Glu Trp Ala
                245                 250                 255

Phe Trp Glu Thr Lys Lys Asn Leu Thr Arg Lys Ile Arg Ser Glu Glu
                260                 265                 270

Leu Ser Phe Thr Val Val Ser Thr His His Gln Asp Thr Gly Glu Glu
                275                 280                 285

Ser Ala Ser Ser Gly Lys Leu Gly Leu Ile Thr Asn Thr Ile Ala Gly
                290                 295                 300

Val Ala Gly Leu Ile Thr Gly Gly Arg Arg Thr Arg Arg Glu Ala Ile
305                 310                 315                 320

Val Asn Ala Gln Pro Lys Cys Asn Pro Asn Leu His Tyr Trp Thr Thr
                325                 330                 335

Gln Asp Glu Gly Ala Ala Ile Gly Leu Ala Trp Ile Pro Tyr Phe Gly
                340                 345                 350

Pro Ala Ala Glu Gly Ile Tyr Ile Glu Gly Leu Met His Asn Gln Asp
                355                 360                 365

Gly Leu Ile Cys Gly Leu Arg Gln Leu Ala Asn Glu Thr Thr Gln Ala
                370                 375                 380

Leu Gln Leu Phe Leu Arg Ala Thr Thr Glu Leu Arg Thr Phe Ser Ile
385                 390                 395                 400

Leu Asn Arg Lys Ala Ile Asp Phe Leu Leu Gln Arg Trp Gly Gly Thr
                405                 410                 415

Cys His Ile Leu Gly Pro Asp Cys Cys Ile Glu Gly His Asp Phe Thr
                420                 425                 430

Lys Gln Leu Glu Asp Lys Val Glu Glu Asn Leu Ser Lys Val Tyr His
                435                 440                 445

Asn Glu Asn Glu Val Ala Arg Leu Lys Lys Leu Val Gly Glu Arg
                450                 455                 460

<210> SEQ ID NO 6
<211> LENGTH: 453
<212> TYPE: PRT
<213> ORGANISM: Artificial sequence
<220> FEATURE:
<223> OTHER INFORMATION: Synthetic sequence

<400> SEQUENCE: 6

Pro Leu Gly Val Ile His Asn Ser Ala Leu Gln Val Ser Asp Val Asp
1               5                   10                  15

Lys Leu Val Cys Arg Asp Lys Leu Ser Ser Thr Asn Gln Leu Arg Ser
                20                  25                  30

Val Gly Leu Asn Leu Glu Gly Asn Gly Val Ala Thr Asp Val Pro Ser
                35                  40                  45

Ala Thr Lys Arg Trp Gly Phe Arg Ser Gly Val Pro Pro Lys Val Val
50                  55                  60

Asn Tyr Glu Ala Gly Glu Trp Ala Glu Asn Cys Tyr Asn Leu Glu Ile
```

```
                65                  70                  75                  80
            Lys Lys Pro Asp Gly Ser Glu Cys Leu Pro Ala Ala Pro Asp Gly Ile
                            85                  90                  95

Arg Gly Phe Pro Arg Cys Arg Tyr Val His Lys Val Ser Gly Thr Gly
                        100                 105                 110

Pro Cys Ala Gly Asp Phe Ala Phe His Lys Glu Gly Ala Phe Phe Leu
                        115                 120                 125

Tyr Asp Arg Leu Ala Ser Thr Val Ile Tyr Arg Gly Thr Thr Phe Ala
                    130                 135                 140

Glu Gly Val Val Ala Phe Leu Ile Leu Pro Gln Ala Lys Lys Asp Phe
            145                 150                 155                 160

Phe Ser Ser His Pro Leu Arg Glu Pro Val Asn Ala Thr Glu Asp Pro
                            165                 170                 175

Ser Ser Gly Tyr Tyr Ser Thr Thr Ile Arg Tyr Gln Ala Thr Gly Phe
                        180                 185                 190

Gly Thr Asn Glu Thr Glu Tyr Leu Phe Glu Val Asp Asn Leu Thr Tyr
                        195                 200                 205

Val Gln Leu Glu Ser Arg Phe Thr Pro Gln Phe Leu Leu Gln Leu Asn
                    210                 215                 220

Glu Thr Ile Tyr Thr Ser Gly Lys Arg Ser Asn Thr Gly Lys Leu
            225                 230                 235                 240

Ile Trp Lys Val Asn Pro Glu Ile Asp Thr Thr Ile Gly Glu Trp Ala
                            245                 250                 255

Phe Trp Glu Thr Lys Lys Asn Leu Thr Arg Lys Ile Arg Ser Glu Glu
                        260                 265                 270

Leu Ser Phe Thr Val Val Ser Thr His Gln Asp Thr Gly Glu Glu
                    275                 280                 285

Ser Ala Ser Ser Gly Lys Leu Gly Leu Ile Thr Asn Thr Ile Ala Gly
                    290                 295                 300

Val Ala Gly Leu Ile Thr Gly Gly Arg Arg Thr Arg Arg Glu Ala Ile
            305                 310                 315                 320

Val Asn Ala Gln Pro Lys Cys Asn Pro Asn Leu His Tyr Trp Thr Thr
                            325                 330                 335

Gln Asp Glu Gly Ala Ala Ile Gly Leu Ala Trp Ile Pro Tyr Phe Gly
                        340                 345                 350

Pro Ala Ala Glu Gly Ile Tyr Ile Glu Gly Leu Met His Asn Gln Asp
                        355                 360                 365

Gly Leu Ile Cys Gly Leu Arg Gln Leu Ala Asn Glu Thr Thr Gln Ala
                    370                 375                 380

Leu Gln Leu Phe Leu Arg Ala Thr Thr Glu Leu Arg Thr Phe Ser Ile
            385                 390                 395                 400

Leu Asn Arg Lys Ala Ile Asp Phe Leu Leu Gln Arg Trp Gly Gly Thr
                            405                 410                 415

Cys His Ile Leu Gly Pro Asp Cys Cys Ile Glu Pro His Asp Trp Thr
                        420                 425                 430

Lys Asn Ile Thr Asp Lys Ile Asp Gln Ile Ile His Asp Phe Val Asp
                        435                 440                 445

Lys Thr Leu Pro Asp
                450

<210> SEQ ID NO 7
<211> LENGTH: 459
<212> TYPE: PRT
<213> ORGANISM: Artificial sequence
```

<220> FEATURE:
<223> OTHER INFORMATION: Synthetic sequence

<400> SEQUENCE: 7

```
Pro Leu Gly Val Ile His Asn Ser Ala Leu Gln Val Ser Asp Val Asp
1               5                   10                  15
Lys Leu Val Cys Arg Asp Lys Leu Ser Ser Thr Asn Gln Leu Arg Ser
            20                  25                  30
Val Gly Leu Asn Leu Glu Gly Asn Gly Val Ala Thr Asp Val Pro Ser
        35                  40                  45
Ala Thr Lys Arg Trp Gly Phe Arg Ser Gly Val Pro Pro Lys Val Val
    50                  55                  60
Asn Tyr Glu Ala Gly Glu Trp Ala Glu Asn Cys Tyr Asn Leu Glu Ile
65                  70                  75                  80
Lys Lys Pro Asp Gly Ser Glu Cys Leu Pro Ala Ala Pro Asp Gly Ile
                85                  90                  95
Arg Gly Phe Pro Arg Cys Arg Tyr Val His Lys Val Ser Gly Thr Gly
            100                 105                 110
Pro Cys Ala Gly Asp Phe Ala Phe His Lys Glu Gly Ala Phe Phe Leu
        115                 120                 125
Tyr Asp Arg Leu Ala Ser Thr Val Ile Tyr Arg Gly Thr Thr Phe Ala
    130                 135                 140
Glu Gly Val Val Ala Phe Leu Ile Leu Pro Gln Ala Lys Lys Asp Phe
145                 150                 155                 160
Phe Ser Ser His Pro Leu Arg Glu Pro Val Asn Ala Thr Glu Asp Pro
                165                 170                 175
Ser Ser Gly Tyr Tyr Ser Thr Thr Ile Arg Tyr Gln Ala Thr Gly Phe
            180                 185                 190
Gly Thr Asn Glu Thr Glu Tyr Leu Phe Glu Val Asp Asn Leu Thr Tyr
        195                 200                 205
Val Gln Leu Glu Ser Arg Phe Thr Pro Gln Phe Leu Leu Gln Leu Asn
    210                 215                 220
Glu Thr Ile Tyr Thr Ser Gly Lys Arg Ser Asn Thr Thr Gly Lys Leu
225                 230                 235                 240
Ile Trp Lys Val Asn Pro Glu Ile Asp Thr Thr Ile Gly Glu Trp Ala
                245                 250                 255
Phe Trp Glu Thr Lys Lys Asn Leu Thr Arg Lys Ile Arg Ser Glu Glu
            260                 265                 270
Leu Ser Phe Thr Val Val Ser Thr His His Gln Asp Thr Gly Glu Glu
        275                 280                 285
Ser Ala Ser Ser Gly Lys Leu Gly Leu Ile Thr Asn Thr Ile Ala Gly
    290                 295                 300
Val Ala Gly Leu Ile Thr Gly Gly Arg Arg Thr Arg Glu Ala Ile
305                 310                 315                 320
Val Asn Ala Gln Pro Lys Cys Asn Pro Asn Leu His Tyr Trp Thr Thr
                325                 330                 335
Gln Asp Glu Gly Ala Ala Ile Gly Leu Ala Trp Ile Pro Tyr Phe Gly
            340                 345                 350
Pro Ala Ala Glu Gly Ile Tyr Ile Glu Gly Leu Met His Asn Gln Asp
        355                 360                 365
Gly Leu Ile Cys Gly Leu Arg Gln Leu Ala Asn Glu Thr Thr Gln Ala
    370                 375                 380
Leu Gln Leu Phe Leu Arg Ala Thr Thr Glu Leu Arg Thr Phe Ser Ile
385                 390                 395                 400
```

Leu Asn Arg Lys Ala Ile Asp Phe Leu Leu Gln Arg Trp Gly Gly Thr
            405                 410                 415

Cys His Ile Leu Gly Pro Asp Cys Cys Ile Glu Pro His Asp Trp Thr
            420                 425                 430

Lys Asn Ile Thr Asp Lys Ile Asp Gln Ile Ile His Asp Phe Val Asp
            435                 440                 445

Lys Thr Leu Pro Asp Gln Gly Asp Asn Asp Asn
    450                 455

<210> SEQ ID NO 8
<211> LENGTH: 482
<212> TYPE: PRT
<213> ORGANISM: Artificial sequence
<220> FEATURE:
<223> OTHER INFORMATION: Synthetic sequence

<400> SEQUENCE: 8

Pro Leu Gly Val Ile His Asn Ser Ala Leu Gln Val Ser Asp Val Asp
1               5                   10                  15

Lys Leu Val Cys Arg Asp Lys Leu Ser Ser Thr Asn Gln Leu Arg Ser
            20                  25                  30

Val Gly Leu Asn Leu Glu Gly Asn Gly Val Ala Thr Asp Val Pro Ser
        35                  40                  45

Ala Thr Lys Arg Trp Gly Phe Arg Ser Gly Val Pro Pro Lys Val Val
    50                  55                  60

Asn Tyr Glu Ala Gly Glu Trp Ala Glu Asn Cys Tyr Asn Leu Glu Ile
65                  70                  75                  80

Lys Lys Pro Asp Gly Ser Glu Cys Leu Pro Ala Ala Pro Asp Gly Ile
                85                  90                  95

Arg Gly Phe Pro Arg Cys Arg Tyr Val His Lys Val Ser Gly Thr Gly
            100                 105                 110

Pro Cys Ala Gly Asp Phe Ala Phe His Lys Glu Gly Ala Phe Phe Leu
        115                 120                 125

Tyr Asp Arg Leu Ala Ser Thr Val Ile Tyr Arg Gly Thr Thr Phe Ala
    130                 135                 140

Glu Gly Val Val Ala Phe Leu Ile Leu Pro Gln Ala Lys Lys Asp Phe
145                 150                 155                 160

Phe Ser Ser His Pro Leu Arg Glu Pro Val Asn Ala Thr Glu Asp Pro
                165                 170                 175

Ser Ser Gly Tyr Tyr Ser Thr Thr Ile Arg Tyr Gln Ala Thr Gly Phe
            180                 185                 190

Gly Thr Asn Glu Thr Glu Tyr Leu Phe Glu Val Asp Asn Leu Thr Tyr
        195                 200                 205

Val Gln Leu Glu Ser Arg Phe Thr Pro Gln Phe Leu Leu Gln Leu Asn
    210                 215                 220

Glu Thr Ile Tyr Thr Ser Gly Lys Arg Ser Asn Thr Thr Gly Lys Leu
225                 230                 235                 240

Ile Trp Lys Val Asn Pro Glu Ile Asp Thr Thr Ile Gly Glu Trp Ala
                245                 250                 255

Phe Trp Glu Thr Lys Lys Asn Leu Thr Arg Lys Ile Arg Ser Glu Glu
            260                 265                 270

Leu Ser Phe Thr Val Val Ser Thr His His Gln Asp Thr Gly Glu Glu
        275                 280                 285

Ser Ala Ser Ser Gly Lys Leu Gly Leu Ile Thr Asn Thr Ile Ala Gly
    290                 295                 300

```
Val Ala Gly Leu Ile Thr Gly Gly Arg Arg Thr Arg Arg Glu Ala Ile
305                 310                 315                 320

Val Asn Ala Gln Pro Lys Cys Asn Pro Asn Leu His Tyr Trp Thr Thr
                325                 330                 335

Gln Asp Glu Gly Ala Ala Ile Gly Leu Ala Trp Ile Pro Tyr Phe Gly
            340                 345                 350

Pro Ala Ala Glu Gly Ile Tyr Ile Glu Gly Leu Met His Asn Gln Asp
        355                 360                 365

Gly Leu Ile Cys Gly Leu Arg Gln Leu Ala Asn Glu Thr Thr Gln Ala
    370                 375                 380

Leu Gln Leu Phe Leu Arg Ala Thr Thr Glu Leu Arg Thr Phe Ser Ile
385                 390                 395                 400

Leu Asn Arg Lys Ala Ile Asp Phe Leu Leu Gln Arg Trp Gly Gly Thr
                405                 410                 415

Cys His Ile Leu Gly Pro Asp Cys Cys Ile Glu Pro His Asp Leu Thr
            420                 425                 430

Lys Asn Ile Thr Asp Lys Ile Asp Gln Ile Ile His Asp Phe Val Asp
        435                 440                 445

Lys Thr Leu Pro Asp Ala Ser Gly Tyr Ile Pro Glu Ala Pro Arg Asp
    450                 455                 460

Gly Gln Ala Tyr Val Arg Lys Asp Gly Glu Trp Val Leu Leu Ser Thr
465                 470                 475                 480

Phe Leu

<210> SEQ ID NO 9
<211> LENGTH: 448
<212> TYPE: PRT
<213> ORGANISM: Artificial sequence
<220> FEATURE:
<223> OTHER INFORMATION: Synthetic sequence

<400> SEQUENCE: 9

Pro Leu Gly Val Ile His Asn Ser Ala Leu Gln Val Ser Asp Val Asp
1               5                   10                  15

Lys Leu Val Cys Arg Asp Lys Leu Ser Ser Thr Asn Gln Leu Arg Ser
                20                  25                  30

Val Gly Leu Asn Leu Glu Gly Asn Gly Val Ala Thr Asp Val Pro Ser
            35                  40                  45

Ala Thr Lys Arg Trp Gly Phe Arg Ser Gly Val Pro Pro Lys Val Val
        50                  55                  60

Asn Tyr Glu Ala Gly Glu Trp Ala Glu Asn Cys Tyr Asn Leu Glu Ile
65                  70                  75                  80

Lys Lys Pro Asp Gly Ser Glu Cys Leu Pro Ala Ala Pro Asp Gly Ile
                85                  90                  95

Arg Gly Phe Pro Arg Cys Arg Tyr Val His Lys Val Ser Gly Thr Gly
                100                 105                 110

Pro Cys Ala Gly Asp Phe Ala Phe His Lys Glu Gly Ala Phe Phe Leu
            115                 120                 125

Tyr Asp Arg Leu Ala Ser Thr Val Ile Tyr Arg Gly Thr Thr Phe Ala
        130                 135                 140

Glu Gly Val Val Ala Phe Leu Ile Leu Pro Gln Ala Lys Lys Asp Phe
145                 150                 155                 160

Phe Ser Ser His Pro Leu Arg Glu Pro Val Asn Ala Thr Glu Asp Pro
                165                 170                 175
```

Ser Ser Gly Tyr Tyr Ser Thr Thr Ile Arg Tyr Gln Ala Thr Gly Phe
            180                 185                 190

Gly Thr Asn Glu Thr Glu Tyr Leu Phe Glu Val Asp Asn Leu Thr Tyr
        195                 200                 205

Val Gln Leu Glu Ser Arg Phe Thr Pro Gln Phe Leu Leu Gln Leu Asn
    210                 215                 220

Glu Thr Ile Tyr Thr Ser Gly Lys Arg Ser Asn Thr Thr Gly Lys Leu
225                 230                 235                 240

Ile Trp Lys Val Asn Pro Glu Ile Asp Thr Thr Ile Gly Glu Trp Ala
                245                 250                 255

Phe Trp Glu Thr Lys Lys Asn Leu Thr Arg Lys Ile Arg Ser Glu Glu
            260                 265                 270

Leu Ser Phe Thr Val Val Ser Thr His His Gln Asp Thr Gly Glu Glu
        275                 280                 285

Ser Ala Ser Ser Gly Lys Leu Gly Leu Ile Thr Asn Thr Ile Ala Gly
    290                 295                 300

Val Ala Gly Leu Ile Thr Gly Gly Arg Arg Thr Arg Arg Glu Ala Ile
305                 310                 315                 320

Val Asn Ala Gln Pro Lys Cys Asn Pro Asn Leu His Tyr Trp Thr Thr
                325                 330                 335

Gln Asp Glu Gly Ala Ala Ile Gly Leu Ala Trp Ile Pro Tyr Phe Gly
            340                 345                 350

Pro Ala Ala Glu Gly Ile Tyr Ile Glu Gly Leu Met His Asn Gln Asp
        355                 360                 365

Gly Leu Ile Cys Gly Leu Arg Gln Leu Ala Asn Glu Thr Thr Gln Ala
    370                 375                 380

Leu Gln Leu Phe Leu Arg Ala Pro Thr Glu Leu Arg Thr Phe Ser Ile
385                 390                 395                 400

Leu Asn Arg Lys Ala Ile Asp Phe Leu Leu Gln Arg Trp Gly Gly Thr
                405                 410                 415

Cys His Ile Leu Gly Pro Asp Cys Cys Ile Glu Pro His Asp Leu Thr
            420                 425                 430

Lys Asn Ile Thr Asp Lys Ile Asp Gln Ile Ile His Asp Phe Val Asp
        435                 440                 445

<210> SEQ ID NO 10
<211> LENGTH: 448
<212> TYPE: PRT
<213> ORGANISM: Artificial sequence
<220> FEATURE:
<223> OTHER INFORMATION: Synthetic sequence

<400> SEQUENCE: 10

Pro Leu Gly Val Ile His Asn Ser Ala Leu Gln Val Ser Asp Val Asp
1               5                   10                  15

Lys Leu Val Cys Arg Asp Lys Leu Ser Ser Thr Asn Gln Leu Arg Ser
            20                  25                  30

Val Gly Leu Asn Leu Glu Gly Asn Gly Val Ala Thr Asp Val Pro Ser
        35                  40                  45

Ala Thr Lys Arg Trp Gly Phe Arg Ser Gly Val Pro Pro Lys Val Val
    50                  55                  60

Asn Tyr Glu Ala Gly Glu Trp Ala Glu Asn Cys Tyr Asn Leu Glu Ile
65                  70                  75                  80

Lys Lys Pro Asp Gly Ser Glu Cys Leu Pro Ala Ala Pro Asp Gly Ile
                85                  90                  95

```
Arg Gly Phe Pro Arg Cys Arg Tyr Val His Lys Val Ser Gly Thr Gly
                100                 105                 110

Pro Cys Ala Gly Asp Phe Ala Phe His Lys Glu Gly Ala Phe Phe Leu
            115                 120                 125

Tyr Asp Arg Leu Ala Ser Thr Val Ile Tyr Arg Gly Thr Thr Phe Ala
        130                 135                 140

Glu Gly Val Val Ala Phe Leu Ile Leu Pro Gln Ala Lys Lys Asp Phe
145                 150                 155                 160

Phe Ser Ser His Pro Leu Arg Glu Pro Val Asn Ala Thr Glu Asp Pro
                165                 170                 175

Ser Ser Gly Tyr Tyr Ser Thr Thr Ile Arg Tyr Gln Ala Thr Gly Phe
            180                 185                 190

Gly Thr Asn Glu Thr Glu Tyr Leu Phe Glu Val Asp Asn Leu Thr Tyr
        195                 200                 205

Val Gln Leu Glu Ser Arg Phe Thr Pro Gln Phe Leu Leu Gln Leu Asn
210                 215                 220

Glu Thr Ile Tyr Thr Ser Gly Lys Arg Ser Asn Thr Thr Gly Lys Leu
225                 230                 235                 240

Ile Trp Lys Val Asn Pro Glu Ile Asp Thr Thr Ile Gly Glu Trp Ala
                245                 250                 255

Phe Trp Glu Thr Lys Lys Asn Leu Thr Arg Lys Ile Arg Ser Glu Glu
            260                 265                 270

Leu Ser Phe Thr Val Val Ser Thr His His Gln Asp Thr Gly Glu Glu
        275                 280                 285

Ser Ala Ser Ser Gly Lys Leu Gly Leu Ile Thr Asn Thr Ile Ala Gly
290                 295                 300

Val Ala Gly Leu Ile Thr Gly Gly Arg Arg Thr Arg Arg Glu Ala Ile
305                 310                 315                 320

Val Asn Ala Gln Pro Lys Cys Asn Pro Asn Leu His Tyr Trp Thr Thr
                325                 330                 335

Gln Asp Glu Gly Ala Ala Ile Gly Leu Ala Trp Ile Pro Tyr Phe Gly
            340                 345                 350

Pro Ala Ala Glu Gly Ile Tyr Ile Glu Gly Leu Met His Asn Gln Asp
        355                 360                 365

Gly Leu Ile Cys Gly Leu Arg Gln Leu Ala Asn Glu Thr Thr Gln Ala
370                 375                 380

Leu Gln Leu Phe Leu Arg Ala Thr Pro Glu Leu Arg Thr Phe Ser Ile
385                 390                 395                 400

Leu Asn Arg Lys Ala Ile Asp Phe Leu Leu Gln Arg Trp Gly Gly Thr
                405                 410                 415

Cys His Ile Leu Gly Pro Asp Cys Cys Ile Glu Pro His Asp Leu Thr
            420                 425                 430

Lys Asn Ile Thr Asp Lys Ile Asp Gln Ile Ile His Asp Phe Val Asp
        435                 440                 445

<210> SEQ ID NO 11
<211> LENGTH: 448
<212> TYPE: PRT
<213> ORGANISM: Artificial sequence
<220> FEATURE:
<223> OTHER INFORMATION: Synthetic sequence

<400> SEQUENCE: 11

Pro Leu Gly Val Ile His Asn Ser Ala Leu Gln Val Ser Asp Val Asp
1               5                   10                  15
```

-continued

Lys Leu Val Cys Arg Asp Lys Leu Ser Ser Thr Asn Gln Leu Arg Ser
            20                  25                  30

Val Gly Leu Asn Leu Glu Gly Asn Gly Val Ala Thr Asp Val Pro Ser
                35                  40                  45

Ala Thr Lys Arg Trp Gly Phe Arg Ser Gly Val Pro Pro Lys Val Val
        50                  55                  60

Asn Tyr Glu Ala Gly Glu Trp Ala Glu Asn Cys Tyr Asn Leu Glu Ile
65                  70                  75                  80

Lys Lys Pro Asp Gly Ser Glu Cys Leu Pro Ala Ala Pro Asp Gly Ile
                85                  90                  95

Arg Gly Phe Pro Arg Cys Arg Tyr Val His Lys Val Ser Gly Thr Gly
            100                 105                 110

Pro Cys Ala Gly Asp Phe Ala Phe His Lys Glu Gly Ala Phe Phe Leu
        115                 120                 125

Tyr Asp Arg Leu Ala Ser Thr Val Ile Tyr Arg Gly Thr Thr Phe Ala
        130                 135                 140

Glu Gly Val Val Ala Phe Leu Ile Leu Pro Gln Ala Lys Lys Asp Phe
145                 150                 155                 160

Phe Ser Ser His Pro Leu Arg Glu Pro Val Asn Ala Thr Glu Asp Pro
                165                 170                 175

Ser Ser Gly Tyr Tyr Ser Thr Thr Ile Arg Tyr Gln Ala Thr Gly Phe
            180                 185                 190

Gly Thr Asn Glu Thr Glu Tyr Leu Phe Glu Val Asp Asn Leu Thr Tyr
        195                 200                 205

Val Gln Leu Glu Ser Arg Phe Thr Pro Gln Phe Leu Leu Gln Leu Asn
210                 215                 220

Glu Thr Ile Tyr Thr Ser Gly Lys Arg Ser Asn Thr Thr Gly Lys Leu
225                 230                 235                 240

Ile Trp Lys Val Asn Pro Glu Ile Asp Thr Thr Ile Gly Glu Trp Ala
                245                 250                 255

Phe Trp Glu Thr Lys Lys Asn Leu Thr Arg Lys Ile Arg Ser Glu Glu
            260                 265                 270

Leu Ser Phe Thr Val Val Ser Thr His His Gln Asp Thr Gly Glu Glu
        275                 280                 285

Ser Ala Ser Ser Gly Lys Leu Gly Leu Ile Thr Asn Thr Ile Ala Gly
        290                 295                 300

Val Ala Gly Leu Ile Thr Gly Gly Arg Arg Thr Arg Arg Glu Ala Ile
305                 310                 315                 320

Val Asn Ala Gln Pro Lys Cys Asn Pro Asn Leu His Tyr Trp Thr Thr
                325                 330                 335

Gln Asp Glu Gly Ala Ala Ile Gly Leu Ala Trp Ile Pro Tyr Phe Gly
            340                 345                 350

Pro Ala Ala Glu Gly Ile Tyr Ile Glu Gly Leu Met His Asn Gln Asp
        355                 360                 365

Gly Leu Ile Cys Gly Leu Arg Gln Leu Ala Asn Glu Thr Thr Gln Ala
        370                 375                 380

Leu Gln Leu Phe Leu Arg Ala Thr Thr Pro Leu Arg Thr Phe Ser Ile
385                 390                 395                 400

Leu Asn Arg Lys Ala Ile Asp Phe Leu Leu Gln Arg Trp Gly Gly Thr
                405                 410                 415

Cys His Ile Leu Gly Pro Asp Cys Cys Ile Glu Pro His Asp Leu Thr
            420                 425                 430

Lys Asn Ile Thr Asp Lys Ile Asp Gln Ile Ile His Asp Phe Val Asp

<210> SEQ ID NO 12
<211> LENGTH: 448
<212> TYPE: PRT
<213> ORGANISM: Artificial sequence
<220> FEATURE:
<223> OTHER INFORMATION: Synthetic sequence

<400> SEQUENCE: 12

```
Pro Leu Gly Val Ile His Asn Ser Ala Leu Gln Val Ser Asp Val Asp
1               5                   10                  15

Lys Leu Val Cys Arg Asp Lys Leu Ser Ser Thr Asn Gln Leu Arg Ser
            20                  25                  30

Val Gly Leu Asn Leu Glu Gly Asn Gly Val Ala Thr Asp Val Pro Ser
        35                  40                  45

Ala Thr Lys Arg Trp Gly Phe Arg Ser Gly Val Pro Pro Lys Val Val
    50                  55                  60

Asn Tyr Glu Ala Gly Glu Trp Ala Glu Asn Cys Tyr Asn Leu Glu Ile
65                  70                  75                  80

Lys Lys Pro Asp Gly Ser Glu Cys Leu Pro Ala Ala Pro Asp Gly Ile
                85                  90                  95

Arg Gly Phe Pro Arg Cys Arg Tyr Val His Lys Val Ser Gly Thr Gly
            100                 105                 110

Pro Cys Ala Gly Asp Phe Ala Phe His Lys Glu Gly Ala Phe Phe Leu
        115                 120                 125

Tyr Asp Arg Leu Ala Ser Thr Val Ile Tyr Arg Gly Thr Thr Phe Ala
    130                 135                 140

Glu Gly Val Val Ala Phe Leu Ile Leu Pro Gln Ala Lys Lys Asp Phe
145                 150                 155                 160

Phe Ser Ser His Pro Leu Arg Glu Pro Val Asn Ala Thr Glu Asp Pro
                165                 170                 175

Ser Ser Gly Tyr Tyr Ser Thr Thr Ile Arg Tyr Gln Ala Thr Gly Phe
            180                 185                 190

Gly Thr Asn Glu Thr Glu Tyr Leu Phe Glu Val Asp Asn Leu Thr Tyr
        195                 200                 205

Val Gln Leu Glu Ser Arg Phe Thr Pro Gln Phe Leu Leu Gln Leu Asn
    210                 215                 220

Glu Thr Ile Tyr Thr Ser Gly Lys Arg Ser Asn Thr Thr Gly Lys Leu
225                 230                 235                 240

Ile Trp Lys Val Asn Pro Glu Ile Asp Thr Thr Ile Gly Glu Trp Ala
                245                 250                 255

Phe Trp Glu Thr Lys Lys Asn Leu Thr Arg Lys Ile Arg Ser Glu Glu
            260                 265                 270

Leu Ser Phe Thr Val Val Ser Thr His His Gln Asp Thr Gly Glu Glu
        275                 280                 285

Ser Ala Ser Ser Gly Lys Leu Gly Leu Ile Thr Asn Thr Ile Ala Gly
    290                 295                 300

Val Ala Gly Leu Ile Thr Gly Gly Arg Arg Thr Arg Arg Glu Ala Ile
305                 310                 315                 320

Val Asn Ala Gln Pro Lys Cys Asn Pro Asn Leu His Tyr Trp Thr Thr
                325                 330                 335

Gln Asp Glu Gly Ala Ala Ile Gly Leu Ala Trp Ile Pro Tyr Phe Gly
            340                 345                 350

Pro Ala Ala Glu Gly Ile Tyr Ile Glu Gly Leu Met His Asn Gln Asp
```

|  |  |  | 355 |  |  |  | 360 |  |  |  | 365 |  |  |
|---|---|---|---|---|---|---|---|---|---|---|---|---|---|
| Gly | Leu | Ile | Cys | Gly | Leu | Arg | Gln | Leu | Ala | Asn | Glu | Thr | Thr | Gln | Ala |
|  |  |  | 370 |  |  |  | 375 |  |  |  | 380 |  |  |
| Leu | Gln | Leu | Phe | Leu | Arg | Ala | Thr | Thr | Glu | Pro | Arg | Thr | Phe | Ser | Ile |
| 385 |  |  |  |  | 390 |  |  |  |  | 395 |  |  |  |  | 400 |
| Leu | Asn | Arg | Lys | Ala | Ile | Asp | Phe | Leu | Leu | Gln | Arg | Trp | Gly | Gly | Thr |
|  |  |  |  | 405 |  |  |  |  | 410 |  |  |  |  | 415 |  |
| Cys | His | Ile | Leu | Gly | Pro | Asp | Cys | Cys | Ile | Glu | Pro | His | Asp | Leu | Thr |
|  |  |  | 420 |  |  |  | 425 |  |  |  | 430 |  |  |
| Lys | Asn | Ile | Thr | Asp | Lys | Ile | Asp | Gln | Ile | Ile | His | Asp | Phe | Val | Asp |
|  |  |  | 435 |  |  |  | 440 |  |  |  | 445 |  |  |

<210> SEQ ID NO 13
<211> LENGTH: 448
<212> TYPE: PRT
<213> ORGANISM: Artificial sequence
<220> FEATURE:
<223> OTHER INFORMATION: Synthetic sequence

<400> SEQUENCE: 13

|  |  |  |  |  |  |  |  |  |  |  |  |  |  |  |  |
|---|---|---|---|---|---|---|---|---|---|---|---|---|---|---|---|
| Pro | Leu | Gly | Val | Ile | His | Asn | Ser | Ala | Leu | Gln | Val | Ser | Asp | Val | Asp |
| 1 |  |  |  | 5 |  |  |  |  | 10 |  |  |  |  | 15 |  |
| Lys | Leu | Val | Cys | Arg | Asp | Lys | Leu | Ser | Ser | Thr | Asn | Gln | Leu | Arg | Ser |
|  |  |  | 20 |  |  |  | 25 |  |  |  | 30 |  |  |
| Val | Gly | Leu | Asn | Leu | Glu | Gly | Asn | Gly | Val | Ala | Thr | Asp | Val | Pro | Ser |
|  |  |  | 35 |  |  |  | 40 |  |  |  | 45 |  |  |
| Ala | Thr | Lys | Arg | Trp | Gly | Phe | Arg | Ser | Gly | Val | Pro | Pro | Lys | Val | Val |
|  | 50 |  |  |  |  | 55 |  |  |  |  | 60 |  |  |  |  |
| Asn | Tyr | Glu | Ala | Gly | Glu | Trp | Ala | Glu | Asn | Cys | Tyr | Asn | Leu | Glu | Ile |
| 65 |  |  |  |  | 70 |  |  |  |  | 75 |  |  |  |  | 80 |
| Lys | Lys | Pro | Asp | Gly | Ser | Glu | Cys | Leu | Pro | Ala | Ala | Pro | Asp | Gly | Ile |
|  |  |  | 85 |  |  |  | 90 |  |  |  | 95 |  |  |
| Arg | Gly | Phe | Pro | Arg | Cys | Arg | Tyr | Val | His | Lys | Val | Ser | Gly | Thr | Gly |
|  |  |  | 100 |  |  |  | 105 |  |  |  | 110 |  |  |
| Pro | Cys | Ala | Gly | Asp | Phe | Ala | Phe | His | Lys | Glu | Gly | Ala | Phe | Phe | Leu |
|  |  |  | 115 |  |  |  | 120 |  |  |  | 125 |  |  |
| Tyr | Asp | Arg | Leu | Ala | Ser | Thr | Val | Ile | Tyr | Arg | Gly | Thr | Thr | Phe | Ala |
|  |  |  | 130 |  |  |  | 135 |  |  |  | 140 |  |  |
| Glu | Gly | Val | Val | Ala | Phe | Leu | Ile | Leu | Pro | Gln | Ala | Lys | Lys | Asp | Phe |
| 145 |  |  |  |  | 150 |  |  |  |  | 155 |  |  |  |  | 160 |
| Phe | Ser | Ser | His | Pro | Leu | Arg | Glu | Pro | Val | Asn | Ala | Thr | Glu | Asp | Pro |
|  |  |  |  | 165 |  |  |  |  | 170 |  |  |  |  | 175 |  |
| Ser | Ser | Gly | Tyr | Tyr | Ser | Thr | Thr | Ile | Arg | Tyr | Gln | Ala | Thr | Gly | Phe |
|  |  |  | 180 |  |  |  | 185 |  |  |  | 190 |  |  |
| Gly | Thr | Asn | Glu | Thr | Glu | Tyr | Leu | Phe | Glu | Val | Asp | Asn | Leu | Thr | Tyr |
|  |  |  | 195 |  |  |  | 200 |  |  |  | 205 |  |  |
| Val | Gln | Leu | Glu | Ser | Arg | Phe | Thr | Pro | Gln | Phe | Leu | Leu | Gln | Leu | Asn |
|  |  |  | 210 |  |  |  | 215 |  |  |  | 220 |  |  |
| Glu | Thr | Ile | Tyr | Thr | Ser | Gly | Lys | Arg | Ser | Asn | Thr | Thr | Gly | Lys | Leu |
| 225 |  |  |  |  | 230 |  |  |  |  | 235 |  |  |  |  | 240 |
| Ile | Trp | Lys | Val | Asn | Pro | Glu | Ile | Asp | Thr | Thr | Ile | Gly | Glu | Trp | Ala |
|  |  |  |  | 245 |  |  |  |  | 250 |  |  |  |  | 255 |  |
| Phe | Trp | Glu | Thr | Lys | Lys | Asn | Leu | Thr | Arg | Lys | Ile | Arg | Ser | Glu | Glu |
|  |  |  | 260 |  |  |  | 265 |  |  |  | 270 |  |  |
| Leu | Ser | Phe | Thr | Val | Val | Ser | Thr | His | His | Gln | Asp | Thr | Gly | Glu | Glu |

```
                    275                 280                 285
Ser Ala Ser Ser Gly Lys Leu Gly Leu Ile Thr Asn Thr Ile Ala Gly
    290                 295                 300

Val Ala Gly Leu Ile Thr Gly Gly Arg Arg Thr Arg Arg Glu Ala Ile
305                 310                 315                 320

Val Asn Ala Gln Pro Lys Cys Asn Pro Asn Leu His Tyr Trp Thr Thr
                325                 330                 335

Gln Asp Glu Gly Ala Ala Ile Gly Leu Ala Trp Ile Pro Tyr Phe Gly
            340                 345                 350

Pro Ala Ala Glu Gly Ile Tyr Ile Glu Gly Leu Met His Asn Gln Asp
        355                 360                 365

Gly Leu Ile Cys Gly Leu Arg Gln Leu Ala Asn Glu Thr Thr Gln Ala
    370                 375                 380

Leu Gln Leu Phe Leu Arg Ala Thr Thr Glu Leu Pro Thr Phe Ser Ile
385                 390                 395                 400

Leu Asn Arg Lys Ala Ile Asp Phe Leu Leu Gln Arg Trp Gly Gly Thr
                405                 410                 415

Cys His Ile Leu Gly Pro Asp Cys Cys Ile Glu Pro His Asp Leu Thr
            420                 425                 430

Lys Asn Ile Thr Asp Lys Ile Asp Gln Ile Ile His Asp Phe Val Asp
        435                 440                 445

<210> SEQ ID NO 14
<211> LENGTH: 448
<212> TYPE: PRT
<213> ORGANISM: Artificial sequence
<220> FEATURE:
<223> OTHER INFORMATION: Synthetic sequence

<400> SEQUENCE: 14

Pro Leu Gly Val Ile His Asn Ser Ala Leu Gln Val Ser Asp Val Asp
1               5                   10                  15

Lys Leu Val Cys Arg Asp Lys Leu Ser Ser Thr Asn Gln Leu Arg Ser
            20                  25                  30

Val Gly Leu Asn Leu Glu Gly Asn Gly Val Ala Thr Asp Val Pro Ser
        35                  40                  45

Ala Thr Lys Arg Trp Gly Phe Arg Ser Gly Val Pro Pro Lys Val Val
    50                  55                  60

Asn Tyr Glu Ala Gly Glu Trp Ala Glu Asn Cys Tyr Asn Leu Glu Ile
65                  70                  75                  80

Lys Lys Pro Asp Gly Ser Glu Cys Leu Pro Ala Ala Pro Asp Gly Ile
                85                  90                  95

Arg Gly Phe Pro Arg Cys Arg Tyr Val His Lys Val Ser Gly Thr Gly
            100                 105                 110

Pro Cys Ala Gly Asp Phe Ala Phe His Lys Glu Gly Ala Phe Phe Leu
        115                 120                 125

Tyr Asp Arg Leu Ala Ser Thr Val Ile Tyr Arg Gly Thr Thr Phe Ala
    130                 135                 140

Glu Gly Val Val Ala Phe Leu Ile Leu Pro Gln Ala Lys Lys Asp Phe
145                 150                 155                 160

Phe Ser Ser His Pro Leu Arg Glu Pro Val Asn Ala Thr Glu Asp Pro
                165                 170                 175

Ser Ser Gly Tyr Tyr Ser Thr Thr Ile Arg Tyr Gln Ala Thr Gly Phe
            180                 185                 190

Gly Thr Asn Glu Thr Glu Tyr Leu Phe Glu Val Asp Asn Leu Thr Tyr
```

```
              195                 200                 205
Val Gln Leu Glu Ser Arg Phe Thr Pro Gln Phe Leu Gln Leu Asn
210                 215                 220

Glu Thr Ile Tyr Thr Ser Gly Lys Arg Ser Asn Thr Thr Gly Lys Leu
225                 230                 235                 240

Ile Trp Lys Val Asn Pro Glu Ile Asp Thr Thr Ile Gly Glu Trp Ala
                245                 250                 255

Phe Trp Glu Thr Lys Lys Asn Leu Thr Arg Lys Ile Arg Ser Glu Glu
                260                 265                 270

Leu Ser Phe Thr Val Val Ser Thr His His Gln Asp Thr Gly Glu Glu
            275                 280                 285

Ser Ala Ser Ser Gly Lys Leu Gly Leu Ile Thr Asn Thr Ile Ala Gly
            290                 295                 300

Val Ala Gly Leu Ile Thr Gly Gly Arg Arg Thr Arg Arg Glu Ala Ile
305                 310                 315                 320

Val Asn Ala Gln Pro Lys Cys Asn Pro Asn Leu His Tyr Trp Thr Thr
                325                 330                 335

Gln Asp Glu Gly Ala Ala Ile Gly Leu Ala Trp Ile Pro Tyr Phe Gly
                340                 345                 350

Pro Ala Ala Glu Gly Ile Tyr Ile Glu Gly Leu Met His Asn Gln Asp
                355                 360                 365

Gly Leu Ile Cys Gly Leu Arg Gln Leu Ala Asn Glu Thr Thr Gln Ala
370                 375                 380

Leu Gln Leu Phe Leu Arg Ala Thr Thr Glu Leu Arg Pro Phe Ser Ile
385                 390                 395                 400

Leu Asn Arg Lys Ala Ile Asp Phe Leu Leu Gln Arg Trp Gly Gly Thr
                405                 410                 415

Cys His Ile Leu Gly Pro Asp Cys Cys Ile Glu Pro His Asp Leu Thr
                420                 425                 430

Lys Asn Ile Thr Asp Lys Ile Asp Gln Ile Ile His Asp Phe Val Asp
                435                 440                 445

<210> SEQ ID NO 15
<211> LENGTH: 448
<212> TYPE: PRT
<213> ORGANISM: Artificial sequence
<220> FEATURE:
<223> OTHER INFORMATION: Synthetic sequence

<400> SEQUENCE: 15

Pro Leu Gly Val Ile His Asn Ser Ala Leu Gln Val Ser Asp Val Asp
1               5                   10                  15

Lys Leu Val Cys Arg Asp Lys Leu Ser Ser Thr Asn Gln Leu Arg Ser
                20                  25                  30

Val Gly Leu Asn Leu Glu Gly Asn Gly Val Ala Thr Asp Val Pro Ser
            35                  40                  45

Ala Thr Lys Arg Trp Gly Phe Arg Ser Gly Val Pro Pro Lys Val Val
        50                  55                  60

Asn Tyr Glu Ala Gly Glu Trp Ala Glu Asn Cys Tyr Asn Leu Glu Ile
65              70                  75                  80

Lys Lys Pro Asp Gly Ser Glu Cys Leu Pro Ala Ala Pro Asp Gly Ile
                85                  90                  95

Arg Gly Phe Pro Arg Cys Arg Tyr Val His Lys Val Ser Gly Thr Gly
                100                 105                 110

Pro Cys Ala Gly Asp Phe Ala Phe His Lys Glu Gly Ala Phe Phe Leu
```

```
            115                 120                 125
Tyr Asp Arg Leu Ala Ser Thr Val Ile Tyr Arg Gly Thr Thr Phe Ala
        130                 135                 140

Glu Gly Val Val Ala Phe Leu Ile Leu Pro Gln Ala Lys Lys Asp Phe
145                 150                 155                 160

Phe Ser Ser His Pro Leu Arg Glu Pro Val Asn Ala Thr Glu Asp Pro
                165                 170                 175

Ser Ser Gly Tyr Tyr Ser Thr Thr Ile Arg Tyr Gln Ala Thr Gly Phe
            180                 185                 190

Gly Thr Asn Glu Thr Glu Tyr Leu Phe Glu Val Asp Asn Leu Thr Tyr
        195                 200                 205

Val Gln Leu Glu Ser Arg Phe Thr Pro Gln Phe Leu Leu Gln Leu Asn
    210                 215                 220

Glu Thr Ile Tyr Thr Ser Gly Lys Arg Ser Asn Thr Thr Gly Lys Leu
225                 230                 235                 240

Ile Trp Lys Val Asn Pro Glu Ile Asp Thr Thr Ile Gly Glu Trp Ala
                245                 250                 255

Phe Trp Glu Thr Lys Lys Asn Leu Thr Arg Lys Ile Arg Ser Glu Glu
            260                 265                 270

Leu Ser Phe Thr Val Val Ser Thr His His Gln Asp Thr Gly Glu Glu
        275                 280                 285

Ser Ala Ser Ser Gly Lys Leu Gly Leu Ile Thr Asn Thr Ile Ala Gly
    290                 295                 300

Val Ala Gly Leu Ile Thr Gly Gly Arg Arg Thr Arg Arg Glu Ala Ile
305                 310                 315                 320

Val Asn Ala Gln Pro Lys Cys Asn Pro Asn Leu His Tyr Trp Thr Thr
                325                 330                 335

Gln Asp Glu Gly Ala Ala Ile Gly Leu Ala Trp Ile Pro Tyr Phe Gly
            340                 345                 350

Pro Ala Ala Glu Gly Ile Tyr Ile Glu Gly Leu Met His Asn Gln Asp
        355                 360                 365

Gly Leu Ile Cys Gly Leu Arg Gln Leu Ala Asn Glu Thr Thr Gln Ala
    370                 375                 380

Leu Gln Leu Phe Leu Arg Ala Thr Thr Glu Leu Arg Thr Pro Ser Ile
385                 390                 395                 400

Leu Asn Arg Lys Ala Ile Asp Phe Leu Leu Gln Arg Trp Gly Gly Thr
                405                 410                 415

Cys His Ile Leu Gly Pro Asp Cys Cys Ile Glu Pro His Asp Leu Thr
            420                 425                 430

Lys Asn Ile Thr Asp Lys Ile Asp Gln Ile Ile His Asp Phe Val Asp
        435                 440                 445

<210> SEQ ID NO 16
<211> LENGTH: 448
<212> TYPE: PRT
<213> ORGANISM: Artificial sequence
<220> FEATURE:
<223> OTHER INFORMATION: Synthetic sequence

<400> SEQUENCE: 16

Pro Leu Gly Val Ile His Asn Ser Ala Leu Gln Val Ser Asp Val Asp
1               5                   10                  15

Lys Leu Val Cys Arg Asp Lys Leu Ser Ser Thr Asn Gln Leu Arg Ser
            20                  25                  30

Val Gly Leu Asn Leu Glu Gly Asn Gly Val Ala Thr Asp Val Pro Ser
```

```
                35                  40                  45
Ala Thr Lys Arg Trp Gly Phe Arg Ser Gly Val Pro Pro Lys Val Val
 50                  55                  60

Asn Tyr Glu Ala Gly Glu Trp Ala Glu Asn Cys Tyr Asn Leu Glu Ile
 65                  70                  75                  80

Lys Lys Pro Asp Gly Ser Glu Cys Leu Pro Ala Ala Pro Asp Gly Ile
                 85                  90                  95

Arg Gly Phe Pro Arg Cys Arg Tyr Val His Lys Val Ser Gly Thr Gly
            100                 105                 110

Pro Cys Ala Gly Asp Phe Ala Phe His Lys Glu Gly Ala Phe Phe Leu
        115                 120                 125

Tyr Asp Arg Leu Ala Ser Thr Val Ile Tyr Arg Gly Thr Thr Phe Ala
130                 135                 140

Glu Gly Val Val Ala Phe Leu Ile Leu Pro Gln Ala Lys Lys Asp Phe
145                 150                 155                 160

Phe Ser Ser His Pro Leu Arg Glu Pro Val Asn Ala Thr Glu Asp Pro
                165                 170                 175

Ser Ser Gly Tyr Tyr Ser Thr Thr Ile Arg Tyr Gln Ala Thr Gly Phe
            180                 185                 190

Gly Thr Asn Glu Thr Glu Tyr Leu Phe Glu Val Asp Asn Leu Thr Tyr
        195                 200                 205

Val Gln Leu Glu Ser Arg Phe Thr Pro Gln Phe Leu Leu Gln Leu Asn
210                 215                 220

Glu Thr Ile Tyr Thr Ser Gly Lys Arg Ser Asn Thr Thr Gly Lys Leu
225                 230                 235                 240

Ile Trp Lys Val Asn Pro Glu Ile Asp Thr Thr Ile Gly Glu Trp Ala
                245                 250                 255

Phe Trp Glu Thr Lys Lys Asn Leu Thr Arg Lys Ile Arg Ser Glu Glu
            260                 265                 270

Leu Ser Phe Thr Val Val Ser Thr His His Gln Asp Thr Gly Glu Glu
        275                 280                 285

Ser Ala Ser Ser Gly Lys Leu Gly Leu Ile Thr Asn Thr Ile Ala Gly
290                 295                 300

Val Ala Gly Leu Ile Thr Gly Gly Arg Arg Thr Arg Arg Glu Ala Ile
305                 310                 315                 320

Val Asn Ala Gln Pro Lys Cys Asn Pro Asn Leu His Tyr Trp Thr Thr
                325                 330                 335

Gln Asp Glu Gly Ala Ala Ile Gly Leu Ala Trp Ile Pro Tyr Phe Gly
            340                 345                 350

Pro Ala Ala Glu Gly Ile Tyr Ile Glu Gly Leu Met His Asn Gln Asp
        355                 360                 365

Gly Leu Ile Cys Gly Leu Arg Gln Leu Ala Asn Glu Thr Thr Gln Ala
370                 375                 380

Leu Gln Leu Phe Leu Arg Ala Thr Thr Glu Leu Arg Thr Phe Pro Ile
385                 390                 395                 400

Leu Asn Arg Lys Ala Ile Asp Phe Leu Leu Gln Arg Trp Gly Gly Thr
                405                 410                 415

Cys His Ile Leu Gly Pro Asp Cys Cys Ile Glu Pro His Asp Leu Thr
            420                 425                 430

Lys Asn Ile Thr Asp Lys Ile Asp Gln Ile Ile His Asp Phe Val Asp
        435                 440                 445

<210> SEQ ID NO 17
```

```
<211> LENGTH: 453
<212> TYPE: PRT
<213> ORGANISM: Artificial sequence
<220> FEATURE:
<223> OTHER INFORMATION: Synthetic sequence

<400> SEQUENCE: 17

Pro Leu Gly Val Ile His Asn Ser Ala Leu Gln Val Ser Asp Val Asp
1               5                   10                  15

Lys Leu Val Cys Arg Asp Lys Leu Ser Ser Thr Asn Gln Leu Arg Ser
            20                  25                  30

Val Gly Leu Asn Leu Glu Gly Asn Gly Val Ala Thr Asp Val Pro Ser
        35                  40                  45

Ala Thr Lys Arg Trp Gly Phe Arg Ser Gly Val Pro Pro Lys Val Val
    50                  55                  60

Asn Tyr Glu Ala Gly Glu Trp Ala Glu Asn Cys Tyr Asn Leu Glu Ile
65                  70                  75                  80

Lys Lys Pro Asp Gly Ser Glu Cys Leu Pro Ala Ala Pro Asp Gly Ile
                85                  90                  95

Arg Gly Phe Pro Arg Cys Arg Tyr Val His Lys Val Ser Gly Thr Gly
            100                 105                 110

Pro Cys Ala Gly Asp Phe Ala Phe His Lys Glu Gly Ala Phe Phe Leu
        115                 120                 125

Tyr Asp Arg Leu Ala Ser Thr Val Ile Tyr Arg Gly Thr Thr Phe Ala
    130                 135                 140

Glu Gly Val Val Ala Phe Leu Ile Leu Pro Gln Ala Lys Lys Asp Phe
145                 150                 155                 160

Phe Ser Ser His Pro Leu Arg Glu Pro Val Asn Ala Thr Glu Asp Pro
                165                 170                 175

Ser Ser Gly Tyr Tyr Ser Thr Thr Ile Arg Tyr Gln Ala Thr Gly Phe
            180                 185                 190

Gly Thr Asn Glu Thr Glu Tyr Leu Phe Glu Val Asp Asn Leu Thr Tyr
        195                 200                 205

Val Gln Leu Glu Ser Arg Phe Thr Pro Gln Phe Leu Leu Gln Leu Asn
    210                 215                 220

Glu Thr Ile Tyr Thr Ser Gly Lys Arg Ser Asn Thr Thr Gly Lys Leu
225                 230                 235                 240

Ile Trp Lys Val Asn Pro Glu Ile Asp Thr Thr Ile Gly Glu Trp Ala
                245                 250                 255

Phe Trp Glu Thr Lys Lys Asn Leu Thr Arg Lys Ile Arg Ser Glu Glu
            260                 265                 270

Leu Ser Phe Thr Val Val Ser Thr His His Gln Asp Thr Gly Glu Glu
        275                 280                 285

Ser Ala Ser Ser Gly Lys Leu Gly Leu Ile Thr Asn Thr Ile Ala Gly
    290                 295                 300

Val Ala Gly Leu Ile Thr Gly Gly Arg Arg Thr Arg Arg Glu Ala Ile
305                 310                 315                 320

Val Asn Ala Gln Pro Lys Cys Asn Pro Asn Leu His Tyr Trp Thr Thr
                325                 330                 335

Gln Asp Glu Gly Ala Ala Ile Gly Leu Ala Trp Ile Pro Tyr Phe Gly
            340                 345                 350

Pro Ala Ala Glu Gly Ile Tyr Ile Glu Gly Leu Met His Asn Gln Asp
        355                 360                 365

Gly Leu Ile Cys Gly Leu Arg Gln Leu Ala Asn Glu Thr Thr Gln Ala
    370                 375                 380
```

Leu Gln Leu Phe Leu Arg Ala Thr Pro Glu Leu Arg Thr Phe Ser Ile
385                 390                 395                 400

Leu Asn Arg Lys Ala Ile Asp Phe Leu Leu Gln Arg Trp Gly Gly Thr
            405                 410                 415

Cys His Ile Leu Gly Pro Asp Cys Cys Ile Glu Pro His Asp Leu Thr
            420                 425                 430

Lys Asn Ile Thr Asp Lys Ile Asp Gln Ile Ile His Asp Phe Val Asp
            435                 440                 445

Lys Thr Leu Pro Asp
        450

<210> SEQ ID NO 18
<211> LENGTH: 482
<212> TYPE: PRT
<213> ORGANISM: Artificial sequence
<220> FEATURE:
<223> OTHER INFORMATION: Synthetic sequence

<400> SEQUENCE: 18

Pro Leu Gly Val Ile His Asn Ser Ala Leu Gln Val Ser Asp Val Asp
1               5                   10                  15

Lys Leu Val Cys Arg Asp Lys Leu Ser Ser Thr Asn Gln Leu Arg Ser
            20                  25                  30

Val Gly Leu Asn Leu Glu Gly Asn Gly Val Ala Thr Asp Val Pro Ser
            35                  40                  45

Ala Thr Lys Arg Trp Gly Phe Arg Ser Gly Val Pro Pro Lys Val Val
        50                  55                  60

Asn Tyr Glu Ala Gly Glu Trp Ala Glu Asn Cys Tyr Asn Leu Glu Ile
65              70                  75                  80

Lys Lys Pro Asp Gly Ser Glu Cys Leu Pro Ala Ala Pro Asp Gly Ile
            85                  90                  95

Arg Gly Phe Pro Arg Cys Arg Tyr Val His Lys Val Ser Gly Thr Gly
            100                 105                 110

Pro Cys Ala Gly Asp Phe Ala Phe His Lys Glu Gly Ala Phe Phe Leu
            115                 120                 125

Tyr Asp Arg Leu Ala Ser Thr Val Ile Tyr Arg Gly Thr Thr Phe Ala
            130                 135                 140

Glu Gly Val Val Ala Phe Leu Ile Leu Pro Gln Ala Lys Lys Asp Phe
145                 150                 155                 160

Phe Ser Ser His Pro Leu Arg Glu Pro Val Asn Ala Thr Glu Asp Pro
            165                 170                 175

Ser Ser Gly Tyr Tyr Ser Thr Thr Ile Arg Tyr Gln Ala Thr Gly Phe
            180                 185                 190

Gly Thr Asn Glu Thr Glu Tyr Leu Phe Glu Val Asp Asn Leu Thr Tyr
            195                 200                 205

Val Gln Leu Glu Ser Arg Phe Thr Pro Gln Phe Leu Leu Gln Leu Asn
            210                 215                 220

Glu Thr Ile Tyr Thr Ser Gly Lys Arg Ser Asn Thr Thr Gly Lys Leu
225                 230                 235                 240

Ile Trp Lys Val Asn Pro Glu Ile Asp Thr Thr Ile Gly Glu Trp Ala
            245                 250                 255

Phe Trp Glu Thr Lys Lys Asn Leu Thr Arg Lys Ile Arg Ser Glu Glu
            260                 265                 270

Leu Ser Phe Thr Val Val Ser Thr His His Gln Asp Thr Gly Glu Glu
            275                 280                 285

```
Ser Ala Ser Ser Gly Lys Leu Gly Leu Ile Thr Asn Thr Ile Ala Gly
    290                 295                 300

Val Ala Gly Leu Ile Thr Gly Gly Arg Arg Thr Arg Arg Glu Ala Ile
305                 310                 315                 320

Val Asn Ala Gln Pro Lys Cys Asn Pro Asn Leu His Tyr Trp Thr Thr
                325                 330                 335

Gln Asp Glu Gly Ala Ala Ile Gly Leu Ala Trp Ile Pro Tyr Phe Gly
                340                 345                 350

Pro Ala Ala Glu Gly Ile Tyr Ile Glu Gly Leu Met His Asn Gln Asp
            355                 360                 365

Gly Leu Ile Cys Gly Leu Arg Gln Leu Ala Asn Glu Thr Thr Gln Ala
        370                 375                 380

Leu Gln Leu Phe Leu Arg Ala Thr Pro Glu Leu Arg Thr Phe Ser Ile
385                 390                 395                 400

Leu Asn Arg Lys Ala Ile Asp Phe Leu Leu Gln Arg Trp Gly Gly Thr
                405                 410                 415

Cys His Ile Leu Gly Pro Asp Cys Cys Ile Glu Pro His Asp Leu Thr
                420                 425                 430

Lys Asn Ile Thr Asp Lys Ile Asp Gln Ile Ile His Asp Phe Val Asp
            435                 440                 445

Lys Thr Leu Pro Asp Ala Ser Gly Tyr Ile Pro Glu Ala Pro Arg Asp
    450                 455                 460

Gly Gln Ala Tyr Val Arg Lys Asp Gly Glu Trp Val Leu Leu Ser Thr
465                 470                 475                 480

Phe Leu

<210> SEQ ID NO 19
<211> LENGTH: 562
<212> TYPE: PRT
<213> ORGANISM: Artificial sequence
<220> FEATURE:
<223> OTHER INFORMATION: Synthetic sequence

<400> SEQUENCE: 19

Pro Leu Gly Val Ile His Asn Ser Ala Leu Gln Val Ser Asp Val Asp
1               5                   10                  15

Lys Leu Val Cys Arg Asp Lys Leu Ser Ser Thr Asn Gln Leu Arg Ser
            20                  25                  30

Val Gly Leu Asn Leu Glu Gly Asn Gly Val Ala Thr Asp Val Pro Ser
        35                  40                  45

Ala Thr Lys Arg Trp Gly Phe Arg Ser Gly Val Pro Pro Lys Val Val
    50                  55                  60

Asn Tyr Glu Ala Gly Glu Trp Ala Glu Asn Cys Tyr Asn Leu Glu Ile
65                  70                  75                  80

Lys Lys Pro Asp Gly Ser Glu Cys Leu Pro Ala Ala Pro Asp Gly Ile
                85                  90                  95

Arg Gly Phe Pro Arg Cys Arg Tyr Val His Lys Val Ser Gly Thr Gly
                100                 105                 110

Pro Cys Ala Gly Asp Phe Ala Phe His Lys Glu Gly Ala Phe Phe Leu
            115                 120                 125

Tyr Asp Arg Leu Ala Ser Thr Val Ile Tyr Arg Gly Thr Thr Phe Ala
        130                 135                 140

Glu Gly Val Val Ala Phe Leu Ile Leu Pro Gln Ala Lys Lys Asp Phe
145                 150                 155                 160
```

Phe Ser Ser His Pro Leu Arg Glu Pro Val Asn Ala Thr Glu Asp Pro
            165                 170                 175

Ser Ser Gly Tyr Tyr Ser Thr Thr Ile Arg Tyr Gln Ala Thr Gly Phe
            180                 185                 190

Gly Thr Asn Glu Thr Glu Tyr Leu Phe Glu Val Asp Asn Leu Thr Tyr
            195                 200                 205

Val Gln Leu Glu Ser Arg Phe Thr Pro Gln Phe Leu Leu Gln Leu Asn
210                 215                 220

Glu Thr Ile Tyr Thr Ser Gly Lys Arg Ser Asn Thr Thr Gly Lys Leu
225                 230                 235                 240

Ile Trp Lys Val Asn Pro Glu Ile Asp Thr Thr Ile Gly Glu Trp Ala
            245                 250                 255

Phe Trp Glu Thr Lys Lys Asn Leu Thr Arg Lys Ile Arg Ser Glu Glu
            260                 265                 270

Leu Ser Phe Thr Val Val Ser Thr His His Gln Asp Thr Gly Glu Glu
            275                 280                 285

Ser Ala Ser Ser Gly Lys Leu Gly Leu Ile Thr Asn Thr Ile Ala Gly
            290                 295                 300

Val Ala Gly Leu Ile Thr Gly Gly Arg Arg Thr Arg Arg Glu Ala Ile
305                 310                 315                 320

Val Asn Ala Gln Pro Lys Cys Asn Pro Asn Leu His Tyr Trp Thr Thr
            325                 330                 335

Gln Asp Glu Gly Ala Ala Ile Gly Leu Ala Trp Ile Pro Tyr Phe Gly
            340                 345                 350

Pro Ala Ala Glu Gly Ile Tyr Ile Glu Gly Leu Met His Asn Gln Asp
            355                 360                 365

Gly Leu Ile Cys Gly Leu Arg Gln Leu Ala Asn Glu Thr Thr Gln Ala
            370                 375                 380

Leu Gln Leu Phe Leu Arg Ala Thr Pro Glu Leu Arg Thr Phe Ser Ile
385                 390                 395                 400

Leu Asn Arg Lys Ala Ile Asp Phe Leu Leu Gln Arg Trp Gly Gly Thr
            405                 410                 415

Cys His Ile Leu Gly Pro Asp Cys Cys Ile Glu Pro His Asp Leu Thr
            420                 425                 430

Lys Asn Ile Thr Asp Lys Ile Asp Gln Ile Ile His Asp Phe Val Asp
            435                 440                 445

Lys Thr Leu Pro Asp Ala Ser Gly Gly Gly Ser Glu Val Arg Ile
            450                 455                 460

Phe Ala Gly Asn Asp Pro Ala His Thr Ala Thr Gly Ser Ser Gly Ile
465                 470                 475                 480

Ser Ser Pro Thr Pro Ala Leu Thr Pro Leu Met Leu Asp Glu Ala Thr
            485                 490                 495

Gly Lys Leu Val Val Trp Asp Gly Gln Lys Ala Gly Ser Ala Val Gly
            500                 505                 510

Ile Leu Val Leu Pro Leu Glu Gly Thr Glu Thr Ala Leu Thr Tyr Tyr
            515                 520                 525

Lys Ser Gly Thr Phe Ala Thr Glu Ala Ile His Trp Pro Glu Ser Val
            530                 535                 540

Asp Glu His Lys Lys Ala Asn Ala Phe Ala Gly Ser Ala Leu Ser His
545                 550                 555                 560

Ala Ala

<210> SEQ ID NO 20

```
<211> LENGTH: 453
<212> TYPE: PRT
<213> ORGANISM: Artificial sequence
<220> FEATURE:
<223> OTHER INFORMATION: Synthetic sequence

<400> SEQUENCE: 20

Pro Leu Gly Val Ile His Asn Ser Ala Leu Gln Val Ser Asp Val Asp
1               5                   10                  15

Lys Leu Val Cys Arg Asp Lys Leu Ser Ser Thr Asn Gln Leu Arg Ser
            20                  25                  30

Val Gly Leu Asn Leu Glu Gly Asn Gly Val Ala Thr Asp Val Pro Ser
        35                  40                  45

Ala Thr Lys Arg Trp Gly Phe Arg Ser Gly Val Pro Pro Lys Val Val
    50                  55                  60

Asn Tyr Glu Ala Gly Glu Trp Ala Glu Asn Cys Tyr Asn Leu Glu Ile
65                  70                  75                  80

Lys Lys Pro Asp Gly Ser Glu Cys Leu Pro Ala Ala Pro Asp Gly Ile
                85                  90                  95

Arg Gly Phe Pro Arg Cys Arg Tyr Val His Lys Val Ser Gly Thr Gly
            100                 105                 110

Pro Cys Ala Gly Asp Phe Ala Phe His Lys Glu Gly Ala Phe Phe Leu
        115                 120                 125

Tyr Asp Arg Leu Ala Ser Thr Val Ile Tyr Arg Gly Thr Thr Phe Ala
    130                 135                 140

Glu Gly Val Val Ala Phe Leu Ile Leu Pro Gln Ala Lys Lys Asp Phe
145                 150                 155                 160

Phe Ser Ser His Pro Leu Arg Glu Pro Val Asn Ala Thr Glu Asp Pro
                165                 170                 175

Ser Ser Gly Tyr Tyr Ser Thr Thr Ile Arg Tyr Gln Ala Thr Gly Phe
            180                 185                 190

Gly Thr Asn Glu Thr Glu Tyr Leu Phe Glu Val Asp Asn Leu Thr Tyr
        195                 200                 205

Val Gln Leu Glu Ser Arg Phe Thr Pro Gln Phe Leu Leu Gln Leu Asn
    210                 215                 220

Glu Thr Ile Tyr Thr Ser Gly Lys Arg Ser Asn Thr Thr Gly Lys Leu
225                 230                 235                 240

Ile Trp Lys Val Asn Pro Glu Ile Asp Thr Thr Ile Gly Glu Trp Ala
                245                 250                 255

Phe Trp Glu Thr Lys Lys Asn Leu Thr Arg Lys Ile Arg Ser Glu Glu
            260                 265                 270

Leu Ser Phe Thr Val Val Ser Thr His His Gln Asp Thr Gly Glu Glu
        275                 280                 285

Ser Ala Ser Ser Gly Lys Leu Gly Leu Ile Thr Asn Thr Ile Ala Gly
    290                 295                 300

Val Ala Gly Leu Ile Thr Gly Gly Arg Arg Thr Arg Arg Glu Ala Ile
305                 310                 315                 320

Val Asn Ala Gln Pro Lys Cys Asn Pro Asn Leu His Tyr Trp Thr Thr
                325                 330                 335

Gln Asp Glu Gly Ala Ala Ile Gly Leu Ala Trp Ile Pro Tyr Phe Gly
            340                 345                 350

Pro Ala Ala Glu Gly Ile Tyr Ile Glu Gly Leu Met His Asn Gln Asp
        355                 360                 365

Gly Leu Ile Cys Gly Leu Arg Gln Leu Ala Asn Glu Thr Thr Gln Ala
    370                 375                 380
```

```
Leu Gln Leu Phe Leu Arg Ala Thr Thr Glu Pro Arg Thr Phe Ser Ile
385                 390                 395                 400

Leu Asn Arg Lys Ala Ile Asp Phe Leu Leu Gln Arg Trp Gly Gly Thr
                405                 410                 415

Cys His Ile Leu Gly Pro Asp Cys Cys Ile Glu Pro His Asp Leu Thr
            420                 425                 430

Lys Asn Ile Thr Asp Lys Ile Asp Gln Ile Ile His Asp Phe Val Asp
        435                 440                 445

Lys Thr Leu Pro Asp
    450

<210> SEQ ID NO 21
<211> LENGTH: 482
<212> TYPE: PRT
<213> ORGANISM: Artificial sequence
<220> FEATURE:
<223> OTHER INFORMATION: Synthetic sequence

<400> SEQUENCE: 21

Pro Leu Gly Val Ile His Asn Ser Ala Leu Gln Val Ser Asp Val Asp
1               5                   10                  15

Lys Leu Val Cys Arg Asp Lys Leu Ser Ser Thr Asn Gln Leu Arg Ser
                20                  25                  30

Val Gly Leu Asn Leu Glu Gly Asn Gly Val Ala Thr Asp Val Pro Ser
            35                  40                  45

Ala Thr Lys Arg Trp Gly Phe Arg Ser Gly Val Pro Pro Lys Val Val
        50                  55                  60

Asn Tyr Glu Ala Gly Glu Trp Ala Glu Asn Cys Tyr Asn Leu Glu Ile
65                  70                  75                  80

Lys Lys Pro Asp Gly Ser Glu Cys Leu Pro Ala Ala Pro Asp Gly Ile
                85                  90                  95

Arg Gly Phe Pro Arg Cys Arg Tyr Val His Lys Val Ser Gly Thr Gly
                100                 105                 110

Pro Cys Ala Gly Asp Phe Ala Phe His Lys Glu Gly Ala Phe Phe Leu
            115                 120                 125

Tyr Asp Arg Leu Ala Ser Thr Val Ile Tyr Arg Gly Thr Thr Phe Ala
        130                 135                 140

Glu Gly Val Val Ala Phe Leu Ile Leu Pro Gln Ala Lys Lys Asp Phe
145                 150                 155                 160

Phe Ser Ser His Pro Leu Arg Glu Pro Val Asn Ala Thr Glu Asp Pro
                165                 170                 175

Ser Ser Gly Tyr Tyr Ser Thr Thr Ile Arg Tyr Gln Ala Thr Gly Phe
            180                 185                 190

Gly Thr Asn Glu Thr Glu Tyr Leu Phe Glu Val Asp Asn Leu Thr Tyr
        195                 200                 205

Val Gln Leu Glu Ser Arg Phe Thr Pro Gln Phe Leu Leu Gln Leu Asn
    210                 215                 220

Glu Thr Ile Tyr Thr Ser Gly Lys Arg Ser Asn Thr Thr Gly Lys Leu
225                 230                 235                 240

Ile Trp Lys Val Asn Pro Glu Ile Asp Thr Thr Ile Gly Glu Trp Ala
                245                 250                 255

Phe Trp Glu Thr Lys Lys Asn Leu Thr Arg Lys Ile Arg Ser Glu Glu
                260                 265                 270

Leu Ser Phe Thr Val Val Ser Thr His His Gln Asp Thr Gly Glu Glu
            275                 280                 285
```

```
Ser Ala Ser Ser Gly Lys Leu Gly Leu Ile Thr Asn Thr Ile Ala Gly
    290                 295                 300

Val Ala Gly Leu Ile Thr Gly Gly Arg Arg Thr Arg Glu Ala Ile
305                 310                 315                 320

Val Asn Ala Gln Pro Lys Cys Asn Pro Asn Leu His Tyr Trp Thr Thr
                325                 330                 335

Gln Asp Glu Gly Ala Ala Ile Gly Leu Ala Trp Ile Pro Tyr Phe Gly
                340                 345                 350

Pro Ala Ala Glu Gly Ile Tyr Ile Glu Gly Leu Met His Asn Gln Asp
                355                 360                 365

Gly Leu Ile Cys Gly Leu Arg Gln Leu Ala Asn Glu Thr Thr Gln Ala
    370                 375                 380

Leu Gln Leu Phe Leu Arg Ala Thr Thr Glu Pro Arg Thr Phe Ser Ile
385                 390                 395                 400

Leu Asn Arg Lys Ala Ile Asp Phe Leu Leu Gln Arg Trp Gly Gly Thr
                405                 410                 415

Cys His Ile Leu Gly Pro Asp Cys Cys Ile Glu Pro His Asp Leu Thr
                420                 425                 430

Lys Asn Ile Thr Asp Lys Ile Asp Gln Ile Ile His Asp Phe Val Asp
                435                 440                 445

Lys Thr Leu Pro Asp Ala Ser Gly Tyr Ile Pro Glu Ala Pro Arg Asp
    450                 455                 460

Gly Gln Ala Tyr Val Arg Lys Asp Gly Glu Trp Val Leu Leu Ser Thr
465                 470                 475                 480

Phe Leu

<210> SEQ ID NO 22
<211> LENGTH: 562
<212> TYPE: PRT
<213> ORGANISM: Artificial sequence
<220> FEATURE:
<223> OTHER INFORMATION: Synthetic sequence

<400> SEQUENCE: 22

Pro Leu Gly Val Ile His Asn Ser Ala Leu Gln Val Ser Asp Val Asp
1               5                   10                  15

Lys Leu Val Cys Arg Asp Lys Leu Ser Ser Thr Asn Gln Leu Arg Ser
                20                  25                  30

Val Gly Leu Asn Leu Glu Gly Asn Gly Val Ala Thr Asp Val Pro Ser
            35                  40                  45

Ala Thr Lys Arg Trp Gly Phe Arg Ser Gly Val Pro Pro Lys Val Val
50                  55                  60

Asn Tyr Glu Ala Gly Glu Trp Ala Glu Asn Cys Tyr Asn Leu Glu Ile
65                  70                  75                  80

Lys Lys Pro Asp Gly Ser Glu Cys Leu Pro Ala Ala Pro Asp Gly Ile
                85                  90                  95

Arg Gly Phe Pro Arg Cys Arg Tyr Val His Lys Val Ser Gly Thr Gly
                100                 105                 110

Pro Cys Ala Gly Asp Phe Ala Phe His Lys Glu Gly Ala Phe Phe Leu
            115                 120                 125

Tyr Asp Arg Leu Ala Ser Thr Val Ile Tyr Arg Gly Thr Thr Phe Ala
        130                 135                 140

Glu Gly Val Val Ala Phe Leu Ile Leu Pro Gln Ala Lys Lys Asp Phe
145                 150                 155                 160
```

Phe Ser Ser His Pro Leu Arg Glu Pro Val Asn Ala Thr Glu Asp Pro
                165                 170                 175

Ser Ser Gly Tyr Tyr Ser Thr Thr Ile Arg Tyr Gln Ala Thr Gly Phe
            180                 185                 190

Gly Thr Asn Glu Thr Glu Tyr Leu Phe Glu Val Asp Asn Leu Thr Tyr
            195                 200                 205

Val Gln Leu Glu Ser Arg Phe Thr Pro Gln Phe Leu Leu Gln Leu Asn
210                 215                 220

Glu Thr Ile Tyr Thr Ser Gly Lys Arg Ser Asn Thr Thr Gly Lys Leu
225                 230                 235                 240

Ile Trp Lys Val Asn Pro Glu Ile Asp Thr Thr Ile Gly Glu Trp Ala
                245                 250                 255

Phe Trp Glu Thr Lys Lys Asn Leu Thr Arg Lys Ile Arg Ser Glu Glu
            260                 265                 270

Leu Ser Phe Thr Val Val Ser Thr His His Gln Asp Thr Gly Glu Glu
            275                 280                 285

Ser Ala Ser Ser Gly Lys Leu Gly Leu Ile Thr Asn Thr Ile Ala Gly
            290                 295                 300

Val Ala Gly Leu Ile Thr Gly Gly Arg Arg Thr Arg Arg Glu Ala Ile
305                 310                 315                 320

Val Asn Ala Gln Pro Lys Cys Asn Pro Asn Leu His Tyr Trp Thr Thr
                325                 330                 335

Gln Asp Glu Gly Ala Ala Ile Gly Leu Ala Trp Ile Pro Tyr Phe Gly
            340                 345                 350

Pro Ala Ala Glu Gly Ile Tyr Ile Glu Gly Leu Met His Asn Gln Asp
            355                 360                 365

Gly Leu Ile Cys Gly Leu Arg Gln Leu Ala Asn Glu Thr Thr Gln Ala
370                 375                 380

Leu Gln Leu Phe Leu Arg Ala Thr Thr Glu Pro Arg Thr Phe Ser Ile
385                 390                 395                 400

Leu Asn Arg Lys Ala Ile Asp Phe Leu Leu Gln Arg Trp Gly Gly Thr
                405                 410                 415

Cys His Ile Leu Gly Pro Asp Cys Cys Ile Glu Pro His Asp Leu Thr
            420                 425                 430

Lys Asn Ile Thr Asp Lys Ile Asp Gln Ile Ile His Asp Phe Val Asp
            435                 440                 445

Lys Thr Leu Pro Asp Ala Ser Gly Gly Gly Ser Glu Val Arg Ile
450                 455                 460

Phe Ala Gly Asn Asp Pro Ala His Thr Ala Thr Gly Ser Ser Gly Ile
465                 470                 475                 480

Ser Ser Pro Thr Pro Ala Leu Thr Pro Leu Met Leu Asp Glu Ala Thr
                485                 490                 495

Gly Lys Leu Val Val Trp Asp Gly Gln Lys Ala Gly Ser Ala Val Gly
            500                 505                 510

Ile Leu Val Leu Pro Leu Glu Gly Thr Glu Thr Ala Leu Thr Tyr Tyr
            515                 520                 525

Lys Ser Gly Thr Phe Ala Thr Glu Ala Ile His Trp Pro Glu Ser Val
530                 535                 540

Asp Glu His Lys Lys Ala Asn Ala Phe Ala Gly Ser Ala Leu Ser His
545                 550                 555                 560

Ala Ala

<210> SEQ ID NO 23

<211> LENGTH: 448
<212> TYPE: PRT
<213> ORGANISM: Artificial sequence
<220> FEATURE:
<223> OTHER INFORMATION: Synthetic sequence

<400> SEQUENCE: 23

```
Pro Leu Gly Val Ile His Asn Ser Ala Leu Gln Val Ser Asp Val Asp
1               5                   10                  15

Lys Leu Val Cys Arg Asp Lys Leu Ser Ser Thr Asn Gln Leu Arg Ser
            20                  25                  30

Val Gly Leu Asn Leu Glu Gly Asn Gly Val Ala Thr Asp Val Pro Ser
        35                  40                  45

Ala Thr Lys Arg Trp Gly Phe Arg Ser Gly Val Pro Pro Lys Val Val
    50                  55                  60

Asn Tyr Glu Ala Gly Glu Trp Ala Glu Asn Cys Tyr Asn Leu Glu Ile
65                  70                  75                  80

Lys Lys Pro Asp Gly Ser Glu Cys Leu Pro Ala Ala Pro Asp Gly Ile
                85                  90                  95

Arg Gly Phe Pro Arg Cys Arg Tyr Val His Lys Val Ser Gly Thr Gly
            100                 105                 110

Pro Cys Ala Gly Asp Phe Ala Cys His Lys Glu Gly Ala Phe Phe Leu
        115                 120                 125

Tyr Asp Arg Leu Ala Ser Thr Val Ile Tyr Arg Gly Thr Thr Phe Ala
    130                 135                 140

Glu Gly Val Val Ala Phe Leu Ile Leu Pro Gln Ala Lys Lys Asp Phe
145                 150                 155                 160

Phe Ser Ser His Pro Leu Arg Glu Pro Val Asn Ala Thr Glu Asp Pro
                165                 170                 175

Ser Ser Gly Tyr Tyr Ser Thr Thr Ile Arg Tyr Gln Ala Thr Gly Phe
            180                 185                 190

Gly Thr Asn Glu Thr Glu Tyr Leu Phe Glu Val Asp Asn Leu Thr Tyr
        195                 200                 205

Val Gln Leu Glu Ser Arg Phe Thr Pro Gln Phe Leu Leu Gln Leu Asn
    210                 215                 220

Glu Thr Ile Tyr Thr Ser Gly Lys Arg Ser Asn Thr Thr Gly Lys Leu
225                 230                 235                 240

Ile Trp Lys Val Asn Pro Glu Ile Asp Thr Thr Ile Gly Glu Trp Ala
                245                 250                 255

Phe Trp Glu Thr Lys Lys Asn Leu Thr Arg Lys Ile Arg Ser Glu Glu
            260                 265                 270

Leu Ser Phe Thr Val Val Ser Thr His His Gln Asp Thr Gly Glu Glu
        275                 280                 285

Ser Ala Ser Ser Gly Lys Leu Gly Leu Ile Thr Asn Thr Ile Ala Gly
    290                 295                 300

Val Ala Gly Leu Ile Thr Gly Gly Arg Arg Thr Arg Arg Glu Ala Ile
305                 310                 315                 320

Val Asn Ala Gln Pro Lys Cys Asn Pro Asn Leu His Tyr Trp Thr Thr
                325                 330                 335

Gln Asp Glu Gly Ala Ala Ile Gly Leu Ala Trp Ile Pro Cys Phe Gly
            340                 345                 350

Pro Ala Ala Glu Gly Ile Tyr Ile Glu Gly Leu Met His Asn Gln Asp
        355                 360                 365

Gly Leu Ile Cys Gly Leu Arg Gln Leu Ala Asn Glu Thr Thr Gln Ala
    370                 375                 380
```

```
Leu Gln Leu Phe Leu Arg Ala Thr Thr Glu Leu Arg Thr Phe Ser Ile
385                 390                 395                 400

Leu Asn Arg Lys Ala Ile Asp Phe Leu Leu Gln Arg Trp Gly Gly Thr
            405                 410                 415

Cys His Ile Leu Gly Pro Asp Cys Cys Ile Glu Pro His Asp Trp Thr
            420                 425                 430

Lys Asn Ile Thr Asp Lys Ile Asp Gln Ile Ile His Asp Phe Val Asp
            435                 440                 445
```

<210> SEQ ID NO 24
<211> LENGTH: 448
<212> TYPE: PRT
<213> ORGANISM: Artificial sequence
<220> FEATURE:
<223> OTHER INFORMATION: Synthetic sequence

<400> SEQUENCE: 24

```
Pro Leu Gly Val Ile His Asn Ser Ala Leu Gln Val Ser Asp Val Asp
1               5                   10                  15

Lys Leu Val Cys Arg Asp Lys Leu Ser Ser Thr Asn Gln Leu Arg Ser
            20                  25                  30

Val Gly Leu Asn Leu Glu Gly Asn Gly Val Ala Thr Asp Val Pro Ser
            35                  40                  45

Ala Thr Lys Arg Trp Gly Phe Arg Ser Cys Val Pro Pro Lys Val Val
50                  55                  60

Asn Tyr Glu Ala Gly Glu Trp Ala Glu Asn Cys Tyr Asn Leu Glu Ile
65                  70                  75                  80

Lys Lys Pro Asp Gly Ser Glu Cys Leu Pro Ala Ala Pro Asp Gly Ile
            85                  90                  95

Arg Gly Phe Pro Arg Cys Arg Tyr Val His Lys Val Ser Gly Thr Gly
            100                 105                 110

Pro Cys Ala Gly Asp Phe Ala Phe His Lys Glu Gly Ala Phe Phe Leu
            115                 120                 125

Tyr Asp Arg Leu Ala Ser Thr Val Ile Tyr Arg Gly Thr Thr Phe Ala
            130                 135                 140

Glu Gly Val Val Ala Phe Leu Ile Leu Pro Gln Ala Lys Lys Asp Phe
145                 150                 155                 160

Phe Ser Ser His Pro Leu Arg Glu Pro Val Asn Ala Thr Glu Asp Pro
                165                 170                 175

Ser Ser Gly Tyr Tyr Ser Thr Thr Ile Arg Tyr Gln Ala Thr Gly Phe
            180                 185                 190

Gly Thr Asn Glu Thr Glu Tyr Leu Phe Glu Val Asp Asn Leu Thr Tyr
            195                 200                 205

Val Gln Leu Glu Ser Arg Phe Thr Pro Gln Phe Leu Leu Gln Leu Asn
            210                 215                 220

Glu Thr Ile Tyr Thr Ser Gly Lys Arg Ser Asn Thr Thr Gly Lys Leu
225                 230                 235                 240

Ile Trp Lys Val Asn Pro Glu Ile Asp Thr Thr Ile Gly Glu Trp Ala
                245                 250                 255

Phe Trp Glu Thr Lys Lys Asn Leu Thr Arg Lys Ile Arg Ser Glu Glu
            260                 265                 270

Leu Ser Phe Thr Val Val Ser Thr His His Gln Asp Thr Gly Glu Glu
            275                 280                 285

Ser Ala Ser Ser Gly Lys Leu Gly Leu Ile Thr Asn Thr Ile Ala Gly
            290                 295                 300
```

```
Val Ala Gly Leu Ile Thr Gly Gly Arg Arg Thr Arg Glu Ala Ile
305                 310                 315                 320

Val Asn Ala Gln Pro Lys Cys Asn Pro Asn Leu His Tyr Trp Thr Thr
                325                 330                 335

Gln Asp Glu Gly Ala Ala Ile Gly Leu Ala Trp Ile Pro Tyr Phe Gly
                340                 345                 350

Pro Cys Ala Glu Gly Ile Tyr Ile Glu Gly Leu Met His Asn Gln Asp
            355                 360                 365

Gly Leu Ile Cys Gly Leu Arg Gln Leu Ala Asn Glu Thr Thr Gln Ala
        370                 375                 380

Leu Gln Leu Phe Leu Arg Ala Thr Thr Glu Leu Arg Thr Phe Ser Ile
385                 390                 395                 400

Leu Asn Arg Lys Ala Ile Asp Phe Leu Leu Gln Arg Trp Gly Gly Thr
                405                 410                 415

Cys His Ile Leu Gly Pro Asp Cys Cys Ile Glu Pro His Asp Trp Thr
            420                 425                 430

Lys Asn Ile Thr Asp Lys Ile Asp Gln Ile Ile His Asp Phe Val Asp
        435                 440                 445

<210> SEQ ID NO 25
<211> LENGTH: 448
<212> TYPE: PRT
<213> ORGANISM: Artificial sequence
<220> FEATURE:
<223> OTHER INFORMATION: Synthetic sequence

<400> SEQUENCE: 25

Pro Leu Gly Val Ile His Asn Ser Ala Leu Gln Val Ser Asp Val Asp
1               5                   10                  15

Lys Leu Val Cys Arg Asp Lys Leu Ser Ser Thr Asn Gln Leu Arg Ser
                20                  25                  30

Val Gly Leu Asn Leu Glu Gly Asn Gly Val Ala Thr Asp Val Pro Ser
            35                  40                  45

Ala Thr Lys Arg Trp Gly Phe Arg Ser Gly Val Pro Pro Lys Val Val
        50                  55                  60

Asn Tyr Glu Ala Gly Glu Trp Ala Glu Asn Cys Tyr Asn Leu Glu Ile
65                  70                  75                  80

Lys Lys Pro Asp Gly Ser Glu Cys Leu Pro Ala Ala Pro Asp Gly Ile
                85                  90                  95

Arg Gly Phe Pro Arg Cys Arg Tyr Val His Lys Val Ser Gly Thr Gly
            100                 105                 110

Pro Cys Ala Gly Asp Phe Ala Phe His Lys Glu Gly Ala Phe Phe Leu
        115                 120                 125

Tyr Asp Arg Leu Ala Ser Thr Val Ile Tyr Arg Gly Thr Thr Phe Ala
    130                 135                 140

Glu Gly Val Val Ala Phe Leu Ile Leu Pro Gln Ala Lys Lys Asp Phe
145                 150                 155                 160

Phe Ser Ser His Pro Leu Arg Glu Pro Val Asn Ala Thr Glu Asp Pro
                165                 170                 175

Ser Ser Gly Tyr Tyr Ser Thr Thr Ile Arg Tyr Gln Ala Thr Gly Phe
            180                 185                 190

Gly Thr Asn Glu Thr Glu Tyr Leu Phe Glu Val Asp Asn Leu Thr Tyr
        195                 200                 205

Val Gln Leu Glu Ser Arg Phe Thr Pro Gln Phe Leu Leu Gln Leu Asn
    210                 215                 220
```

```
Glu Thr Ile Tyr Thr Ser Gly Lys Arg Ser Asn Thr Gly Lys Leu
225                 230                 235                 240

Ile Trp Lys Val Asn Pro Glu Ile Asp Thr Thr Ile Gly Glu Trp Ala
                245                 250                 255

Phe Trp Glu Thr Lys Lys Asn Leu Thr Arg Lys Ile Arg Ser Glu Glu
            260                 265                 270

Leu Ser Phe Thr Val Val Ser Thr His His Gln Asp Thr Gly Glu Glu
        275                 280                 285

Ser Ala Ser Ser Gly Lys Leu Gly Leu Ile Thr Asn Thr Ile Ala Gly
    290                 295                 300

Val Ala Gly Leu Ile Thr Gly Gly Arg Arg Thr Arg Glu Ala Ile
305                 310                 315                 320

Val Asn Ala Gln Pro Lys Cys Asn Pro Asn Leu His Tyr Trp Thr Cys
                325                 330                 335

Gln Asp Glu Gly Ala Ala Ile Gly Leu Ala Trp Ile Pro Tyr Phe Gly
            340                 345                 350

Pro Ala Ala Glu Gly Ile Tyr Ile Glu Gly Leu Met His Asn Gln Asp
        355                 360                 365

Gly Leu Ile Cys Gly Leu Arg Gln Leu Ala Asn Glu Thr Thr Gln Ala
    370                 375                 380

Leu Gln Leu Phe Leu Arg Cys Thr Thr Glu Leu Arg Thr Phe Ser Ile
385                 390                 395                 400

Leu Asn Arg Lys Ala Ile Asp Phe Leu Leu Gln Arg Trp Gly Gly Thr
                405                 410                 415

Cys His Ile Leu Gly Pro Asp Cys Cys Ile Glu Pro His Asp Trp Thr
            420                 425                 430

Lys Asn Ile Thr Asp Lys Ile Asp Gln Ile Ile His Asp Phe Val Asp
        435                 440                 445

<210> SEQ ID NO 26
<211> LENGTH: 448
<212> TYPE: PRT
<213> ORGANISM: Artificial sequence
<220> FEATURE:
<223> OTHER INFORMATION: Synthetic sequence

<400> SEQUENCE: 26

Pro Leu Gly Val Ile His Asn Ser Ala Leu Gln Val Ser Asp Val Asp
1               5                   10                  15

Lys Leu Val Cys Arg Asp Lys Leu Ser Ser Thr Asn Gln Leu Arg Ser
                20                  25                  30

Val Gly Leu Asn Leu Glu Gly Asn Gly Val Ala Thr Asp Val Pro Ser
            35                  40                  45

Ala Thr Lys Arg Trp Gly Phe Arg Ser Gly Val Pro Pro Lys Val Val
        50                  55                  60

Asn Tyr Glu Ala Gly Glu Trp Ala Glu Asn Cys Tyr Asn Leu Glu Ile
65                  70                  75                  80

Lys Lys Pro Asp Gly Ser Glu Cys Leu Pro Ala Ala Pro Asp Gly Ile
                85                  90                  95

Arg Gly Phe Pro Arg Cys Arg Tyr Val His Lys Val Ser Gly Thr Gly
            100                 105                 110

Pro Cys Ala Gly Asp Phe Ala Phe His Lys Glu Cys Ala Phe Phe Leu
        115                 120                 125

Tyr Asp Arg Leu Ala Ser Thr Val Ile Tyr Arg Gly Thr Thr Phe Ala
    130                 135                 140
```

```
Glu Gly Val Val Ala Phe Leu Ile Leu Pro Gln Ala Lys Lys Asp Phe
145                 150                 155                 160

Phe Ser Ser His Pro Leu Arg Glu Pro Val Asn Ala Thr Glu Asp Pro
                165                 170                 175

Ser Ser Gly Tyr Tyr Ser Thr Thr Ile Arg Tyr Gln Ala Thr Gly Phe
            180                 185                 190

Gly Thr Asn Glu Thr Glu Tyr Leu Phe Glu Val Asp Asn Leu Thr Tyr
            195                 200                 205

Val Gln Leu Glu Ser Arg Phe Thr Pro Gln Phe Leu Leu Gln Leu Asn
210                 215                 220

Glu Thr Ile Tyr Thr Ser Gly Lys Arg Ser Asn Thr Thr Gly Lys Leu
225                 230                 235                 240

Ile Trp Lys Val Asn Pro Glu Ile Asp Thr Thr Ile Gly Glu Trp Ala
                245                 250                 255

Phe Trp Glu Thr Lys Lys Asn Leu Thr Arg Lys Ile Arg Ser Glu Glu
                260                 265                 270

Leu Ser Phe Thr Val Val Ser Thr His His Gln Asp Thr Gly Glu Glu
            275                 280                 285

Ser Ala Ser Ser Gly Lys Leu Gly Leu Ile Thr Asn Thr Ile Ala Gly
290                 295                 300

Val Ala Gly Leu Ile Thr Gly Gly Arg Arg Thr Arg Arg Glu Ala Ile
305                 310                 315                 320

Val Asn Ala Gln Pro Lys Cys Asn Pro Asn Leu His Tyr Trp Thr Thr
                325                 330                 335

Gln Asp Glu Gly Ala Ala Ile Gly Leu Ala Trp Cys Pro Tyr Phe Gly
            340                 345                 350

Pro Ala Ala Glu Gly Ile Tyr Ile Glu Gly Leu Met His Asn Gln Asp
            355                 360                 365

Gly Leu Ile Cys Gly Leu Arg Gln Leu Ala Asn Glu Thr Thr Gln Ala
370                 375                 380

Leu Gln Leu Phe Leu Arg Ala Thr Thr Glu Leu Arg Thr Phe Ser Ile
385                 390                 395                 400

Leu Asn Arg Lys Ala Ile Asp Phe Leu Leu Gln Arg Trp Gly Gly Thr
                405                 410                 415

Cys His Ile Leu Gly Pro Asp Cys Cys Ile Glu Pro His Asp Trp Thr
                420                 425                 430

Lys Asn Ile Thr Asp Lys Ile Asp Gln Ile Ile His Asp Phe Val Asp
            435                 440                 445

<210> SEQ ID NO 27
<211> LENGTH: 448
<212> TYPE: PRT
<213> ORGANISM: Artificial sequence
<220> FEATURE:
<223> OTHER INFORMATION: Synthetic sequence

<400> SEQUENCE: 27

Pro Leu Gly Val Ile His Asn Ser Ala Leu Gln Val Ser Asp Val Asp
1               5                   10                  15

Lys Leu Val Cys Arg Asp Lys Leu Ser Ser Thr Asn Gln Leu Arg Ser
                20                  25                  30

Val Gly Leu Asn Leu Glu Gly Asn Gly Val Ala Thr Asp Val Pro Ser
            35                  40                  45

Ala Thr Lys Arg Trp Gly Phe Arg Ser Gly Val Pro Pro Lys Val Val
50                  55                  60
```

```
Asn Tyr Glu Ala Gly Glu Trp Ala Glu Asn Cys Tyr Asn Leu Glu Ile
 65                  70                  75                  80

Lys Lys Pro Asp Gly Ser Glu Cys Leu Pro Ala Ala Pro Asp Gly Ile
                 85                  90                  95

Arg Gly Phe Pro Arg Cys Arg Tyr Val His Lys Val Ser Gly Thr Gly
            100                 105                 110

Pro Cys Ala Gly Asp Phe Ala Phe His Lys Glu Gly Ala Phe Phe Leu
        115                 120                 125

Tyr Asp Arg Leu Ala Ser Thr Val Ile Tyr Arg Gly Thr Thr Phe Ala
130                 135                 140

Glu Gly Val Val Ala Phe Leu Ile Leu Pro Gln Ala Lys Lys Asp Phe
145                 150                 155                 160

Phe Ser Ser His Pro Leu Arg Glu Pro Val Asn Ala Thr Glu Asp Pro
                165                 170                 175

Ser Ser Gly Tyr Tyr Ser Thr Thr Ile Arg Tyr Gln Ala Thr Gly Phe
            180                 185                 190

Gly Thr Asn Glu Thr Glu Tyr Leu Phe Glu Val Asp Asn Leu Thr Tyr
        195                 200                 205

Val Gln Leu Glu Ser Arg Phe Thr Pro Gln Phe Leu Leu Gln Leu Asn
210                 215                 220

Glu Thr Ile Tyr Thr Ser Gly Lys Arg Ser Asn Thr Thr Gly Lys Leu
225                 230                 235                 240

Ile Trp Lys Val Asn Pro Glu Ile Asp Thr Thr Ile Gly Glu Trp Ala
                245                 250                 255

Phe Trp Glu Thr Lys Lys Asn Leu Thr Arg Lys Ile Arg Ser Glu Glu
            260                 265                 270

Leu Ser Phe Thr Val Val Ser Thr His His Gln Asp Thr Gly Glu Glu
        275                 280                 285

Ser Ala Ser Ser Gly Lys Leu Gly Leu Ile Thr Asn Thr Ile Ala Gly
290                 295                 300

Val Ala Gly Leu Ile Thr Gly Gly Arg Arg Thr Arg Arg Glu Ala Ile
305                 310                 315                 320

Val Asn Ala Gln Pro Lys Cys Asn Pro Asn Leu His Tyr Trp Thr Thr
                325                 330                 335

Gln Cys Glu Gly Ala Ala Ile Gly Leu Ala Trp Ile Pro Tyr Phe Gly
            340                 345                 350

Pro Ala Ala Glu Gly Ile Tyr Ile Glu Gly Leu Met His Asn Gln Asp
        355                 360                 365

Gly Leu Ile Cys Gly Leu Arg Gln Leu Ala Asn Glu Thr Thr Gln Ala
370                 375                 380

Leu Gln Leu Phe Leu Arg Cys Thr Thr Glu Leu Arg Thr Phe Ser Ile
385                 390                 395                 400

Leu Asn Arg Lys Ala Ile Asp Phe Leu Leu Gln Arg Trp Gly Gly Thr
                405                 410                 415

Cys His Ile Leu Gly Pro Asp Cys Cys Ile Glu Pro His Asp Trp Thr
            420                 425                 430

Lys Asn Ile Thr Asp Lys Ile Asp Gln Ile Ile His Asp Phe Val Asp
        435                 440                 445

<210> SEQ ID NO 28
<211> LENGTH: 448
<212> TYPE: PRT
<213> ORGANISM: Artificial sequence
<220> FEATURE:
```

<223> OTHER INFORMATION: Synthetic sequence

<400> SEQUENCE: 28

```
Pro Leu Gly Val Ile His Asn Ser Ala Leu Gln Val Ser Asp Val Asp
1               5                   10                  15
Cys Leu Val Cys Arg Asp Lys Leu Ser Ser Thr Asn Gln Leu Arg Ser
            20                  25                  30
Val Gly Leu Asn Leu Glu Gly Asn Gly Val Ala Thr Asp Val Pro Ser
        35                  40                  45
Ala Thr Lys Arg Trp Gly Phe Arg Ser Gly Val Pro Pro Lys Val Val
    50                  55                  60
Asn Tyr Glu Ala Gly Glu Trp Ala Glu Asn Cys Tyr Asn Leu Glu Ile
65                  70                  75                  80
Lys Lys Pro Asp Gly Ser Glu Cys Leu Pro Ala Ala Pro Asp Gly Ile
                85                  90                  95
Arg Gly Phe Pro Arg Cys Arg Tyr Val His Lys Val Ser Gly Thr Gly
            100                 105                 110
Pro Cys Ala Gly Asp Phe Ala Phe His Lys Glu Gly Ala Phe Phe Leu
        115                 120                 125
Tyr Asp Arg Leu Ala Ser Thr Val Ile Tyr Arg Gly Thr Thr Phe Ala
    130                 135                 140
Glu Gly Val Val Ala Phe Leu Ile Leu Pro Gln Ala Lys Lys Asp Phe
145                 150                 155                 160
Phe Ser Ser His Pro Leu Arg Glu Pro Val Asn Ala Thr Glu Asp Pro
                165                 170                 175
Ser Ser Gly Tyr Tyr Ser Thr Thr Ile Arg Tyr Gln Ala Thr Gly Phe
            180                 185                 190
Gly Thr Asn Glu Thr Glu Tyr Leu Phe Glu Val Asp Asn Leu Thr Tyr
        195                 200                 205
Val Gln Leu Glu Ser Arg Phe Thr Pro Gln Phe Leu Leu Gln Leu Asn
    210                 215                 220
Glu Thr Ile Tyr Thr Ser Gly Lys Arg Ser Asn Thr Thr Gly Lys Leu
225                 230                 235                 240
Ile Trp Lys Val Asn Pro Glu Ile Asp Thr Thr Ile Gly Glu Trp Ala
                245                 250                 255
Phe Trp Glu Thr Lys Lys Asn Leu Thr Arg Lys Ile Arg Ser Glu Glu
            260                 265                 270
Leu Ser Phe Thr Val Val Ser Thr His His Gln Asp Thr Gly Glu Glu
        275                 280                 285
Ser Ala Ser Ser Gly Lys Leu Gly Leu Ile Thr Asn Thr Ile Ala Gly
    290                 295                 300
Val Ala Gly Leu Ile Thr Gly Gly Arg Arg Thr Arg Arg Glu Ala Ile
305                 310                 315                 320
Val Asn Ala Gln Pro Lys Cys Asn Pro Asn Leu His Tyr Trp Thr Thr
                325                 330                 335
Gln Asp Glu Gly Ala Ala Ile Gly Leu Ala Trp Ile Pro Tyr Phe Gly
            340                 345                 350
Pro Ala Ala Glu Gly Ile Tyr Ile Glu Gly Leu Met His Asn Gln Asp
        355                 360                 365
Gly Leu Ile Cys Gly Leu Arg Gln Leu Ala Asn Glu Thr Thr Gln Ala
    370                 375                 380
Leu Gln Leu Phe Leu Arg Ala Thr Thr Glu Leu Arg Thr Phe Ser Ile
385                 390                 395                 400
```

```
Leu Asn Arg Lys Ala Ile Asp Phe Leu Leu Gln Arg Trp Gly Cys Thr
                405                 410                 415

Cys His Ile Leu Gly Pro Asp Cys Cys Ile Glu Pro His Asp Trp Thr
            420                 425                 430

Lys Asn Ile Thr Asp Lys Ile Asp Gln Ile Ile His Asp Phe Val Asp
        435                 440                 445
```

<210> SEQ ID NO 29
<211> LENGTH: 27
<212> TYPE: PRT
<213> ORGANISM: Artificial sequence
<220> FEATURE:
<223> OTHER INFORMATION: Synthetic sequence

<400> SEQUENCE: 29

```
Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25
```

<210> SEQ ID NO 30
<211> LENGTH: 102
<212> TYPE: PRT
<213> ORGANISM: Artificial sequence
<220> FEATURE:
<223> OTHER INFORMATION: Synthetic sequence

<400> SEQUENCE: 30

```
Glu Val Arg Ile Phe Ala Gly Asn Asp Pro Ala His Thr Ala Thr Gly
1               5                   10                  15

Ser Ser Gly Ile Ser Ser Pro Thr Pro Ala Leu Thr Pro Leu Met Leu
            20                  25                  30

Asp Glu Ala Thr Gly Lys Leu Val Val Trp Asp Gly Gln Lys Ala Gly
        35                  40                  45

Ser Ala Val Gly Ile Leu Val Leu Pro Leu Gly Thr Glu Thr Ala
    50                  55                  60

Leu Thr Tyr Tyr Lys Ser Gly Thr Phe Ala Thr Glu Ala Ile His Trp
65                  70                  75                  80

Pro Glu Ser Val Asp Glu His Lys Lys Ala Asn Ala Phe Ala Gly Ser
                85                  90                  95

Ala Leu Ser His Ala Ala
            100
```

<210> SEQ ID NO 31
<211> LENGTH: 13
<212> TYPE: PRT
<213> ORGANISM: Artificial sequence
<220> FEATURE:
<223> OTHER INFORMATION: Synthetic sequence

<400> SEQUENCE: 31

```
Ala Lys Phe Val Ala Ala Trp Thr Leu Lys Ala Ala Ala
1               5                   10
```

<210> SEQ ID NO 32
<211> LENGTH: 5
<212> TYPE: PRT
<213> ORGANISM: Artificial sequence
<220> FEATURE:
<223> OTHER INFORMATION: Synthetic sequence

<400> SEQUENCE: 32

```
Lys Thr Leu Pro Asp
1               5

<210> SEQ ID NO 33
<211> LENGTH: 11
<212> TYPE: PRT
<213> ORGANISM: Artificial sequence
<220> FEATURE:
<223> OTHER INFORMATION: Synthetic sequence

<400> SEQUENCE: 33

Lys Thr Leu Pro Asp Gln Gly Asp Asn Asp Asn
1               5                   10

<210> SEQ ID NO 34
<211> LENGTH: 31
<212> TYPE: PRT
<213> ORGANISM: Artificial sequence
<220> FEATURE:
<223> OTHER INFORMATION: Synthetic sequence

<400> SEQUENCE: 34

Lys Gln Leu Glu Asp Lys Val Glu Glu Asn Leu Ser Lys Val Tyr His
1               5                   10                  15

Asn Glu Asn Glu Val Ala Arg Leu Lys Lys Leu Val Gly Glu Arg
            20                  25                  30

<210> SEQ ID NO 35
<211> LENGTH: 8
<212> TYPE: PRT
<213> ORGANISM: Artificial sequence
<220> FEATURE:
<223> OTHER INFORMATION: Synthetic sequence

<400> SEQUENCE: 35

Thr Thr Glu Leu Arg Thr Phe Ser
1               5

<210> SEQ ID NO 36
<211> LENGTH: 242
<212> TYPE: PRT
<213> ORGANISM: Artificial sequence
<220> FEATURE:
<223> OTHER INFORMATION: Synthetic sequence

<400> SEQUENCE: 36

Ala Ala Ala Lys Pro Ala Thr Thr Glu Gly Glu Phe Pro Glu Thr Arg
1               5                   10                  15

Glu Lys Met Ser Gly Ile Arg Arg Ala Ile Ala Lys Ala Met Val His
            20                  25                  30

Ser Lys His Thr Ala Pro His Val Thr Leu Met Asp Glu Ala Asp Val
        35                  40                  45

Thr Lys Leu Val Ala His Arg Lys Lys Phe Lys Ala Ile Ala Ala Glu
    50                  55                  60

Lys Gly Ile Lys Leu Thr Phe Leu Pro Tyr Val Val Lys Ala Leu Val
65                  70                  75                  80

Ser Ala Leu Arg Glu Tyr Pro Val Leu Asn Thr Ala Ile Asp Asp Glu
                85                  90                  95

Thr Glu Glu Ile Ile Gln Lys His Tyr Tyr Asn Ile Gly Ile Ala Ala
            100                 105                 110

Asp Thr Asp Arg Gly Leu Leu Val Pro Val Ile Lys His Ala Asp Arg
        115                 120                 125
```

```
Lys Pro Ile Phe Ala Leu Ala Gln Glu Ile Asn Glu Leu Ala Glu Lys
            130                 135                 140

Ala Arg Asp Gly Lys Leu Thr Pro Gly Glu Met Lys Gly Ala Ser Cys
145                 150                 155                 160

Thr Ile Thr Asn Ile Gly Ser Ala Gly Gly Gln Trp Phe Thr Pro Val
                165                 170                 175

Ile Asn His Pro Glu Val Ala Ile Leu Gly Ile Gly Arg Ile Ala Glu
            180                 185                 190

Lys Pro Ile Val Arg Asp Gly Glu Ile Val Ala Ala Pro Met Leu Ala
            195                 200                 205

Leu Ser Leu Ser Phe Asp His Arg Met Ile Asp Gly Ala Thr Ala Gln
210                 215                 220

Lys Ala Leu Asn His Ile Lys Arg Leu Leu Ser Asp Pro Glu Leu Leu
225                 230                 235                 240

Leu Met

<210> SEQ ID NO 37
<211> LENGTH: 205
<212> TYPE: PRT
<213> ORGANISM: Artificial sequence
<220> FEATURE:
<223> OTHER INFORMATION: Synthetic sequence

<400> SEQUENCE: 37

Met Lys Met Glu Glu Leu Phe Lys Lys His Lys Ile Val Ala Val Leu
1               5                   10                  15

Arg Ala Asn Ser Val Glu Glu Ala Lys Met Lys Ala Leu Ala Val Phe
            20                  25                  30

Val Gly Gly Val His Leu Ile Glu Ile Thr Phe Thr Val Pro Asp Ala
        35                  40                  45

Asp Thr Val Ile Lys Glu Leu Ser Phe Leu Lys Glu Leu Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Thr Ile Leu
        115                 120                 125

Lys Leu Phe Pro Gly Glu Val Val Gly Pro Gln Phe Val Lys Ala Met
130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Ile Ala Glu Val Ala Ala Lys
            180                 185                 190

Ala Ala Ala Phe Val Glu Lys Ile Arg Gly Cys Thr Glu
        195                 200                 205

<210> SEQ ID NO 38
<211> LENGTH: 162
<212> TYPE: PRT
<213> ORGANISM: Artificial sequence
<220> FEATURE:
<223> OTHER INFORMATION: Synthetic sequence
```

<400> SEQUENCE: 38

Asp Ile Ile Lys Leu Leu Asn Glu Gln Val Asn Lys Glu Met Asn Ser
1               5                   10                  15

Ser Asn Leu Tyr Met Ser Met Ser Ser Trp Cys Tyr Thr His Ser Leu
                20                  25                  30

Asp Gly Ala Gly Leu Phe Leu Phe Asp His Ala Ala Glu Glu Tyr Glu
            35                  40                  45

His Ala Lys Lys Leu Ile Ile Phe Leu Asn Glu Asn Asn Val Pro Val
        50                  55                  60

Gln Leu Thr Ser Ile Ser Ala Pro Glu His Lys Phe Glu Gly Leu Thr
65                  70                  75                  80

Gln Ile Phe Gln Lys Ala Tyr Glu His Glu Gln His Ile Ser Glu Ser
                85                  90                  95

Ile Asn Asn Ile Val Asp His Ala Ile Lys Ser Lys Asp His Ala Thr
            100                 105                 110

Phe Asn Phe Leu Gln Trp Tyr Val Ala Glu Gln His Glu Glu Glu Val
        115                 120                 125

Leu Phe Lys Asp Ile Leu Asp Lys Ile Glu Leu Ile Gly Asn Glu Asn
130                 135                 140

His Gly Leu Tyr Leu Ala Asp Gln Tyr Val Lys Gly Ile Ala Lys Ser
145                 150                 155                 160

Arg Lys

<210> SEQ ID NO 39
<211> LENGTH: 58
<212> TYPE: PRT
<213> ORGANISM: Artificial sequence
<220> FEATURE:
<223> OTHER INFORMATION: Synthetic sequence

<400> SEQUENCE: 39

Phe Ser Glu Glu Gln Lys Lys Ala Leu Asp Leu Ala Phe Tyr Phe Asp
1               5                   10                  15

Arg Arg Leu Thr Pro Glu Trp Arg Arg Tyr Leu Ser Gln Arg Leu Gly
                20                  25                  30

Leu Asn Glu Glu Gln Ile Glu Arg Trp Phe Arg Arg Lys Glu Gln Gln
            35                  40                  45

Ile Gly Trp Ser His Pro Gln Phe Glu Lys
        50                  55

<210> SEQ ID NO 40
<211> LENGTH: 46
<212> TYPE: PRT
<213> ORGANISM: Artificial sequence
<220> FEATURE:
<223> OTHER INFORMATION: Synthetic sequence

<400> SEQUENCE: 40

Ser Pro Ala Val Asp Ile Gly Asp Arg Leu Asp Glu Leu Glu Lys Ala
1               5                   10                  15

Leu Glu Ala Leu Ser Ala Glu Asp Gly His Asp Asp Val Gly Gln Arg
                20                  25                  30

Leu Glu Ser Leu Leu Arg Arg Trp Asn Ser Arg Arg Ala Asp
            35                  40                  45

<210> SEQ ID NO 41
<211> LENGTH: 33

<212> TYPE: PRT
<213> ORGANISM: Ebola virus

<400> SEQUENCE: 41

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile

<210> SEQ ID NO 42
<211> LENGTH: 10
<212> TYPE: PRT
<213> ORGANISM: Artificial sequence
<220> FEATURE:
<223> OTHER INFORMATION: Synthetic sequence

<400> SEQUENCE: 42

Gly Gly Gly Gly Ser Gly Gly Gly Gly Ser
1               5                   10

<210> SEQ ID NO 43
<211> LENGTH: 5
<212> TYPE: PRT
<213> ORGANISM: Artificial sequence
<220> FEATURE:
<223> OTHER INFORMATION: Synthetic sequence

<400> SEQUENCE: 43

Gly Gly Gly Gly Ser
1               5

<210> SEQ ID NO 44
<211> LENGTH: 50
<212> TYPE: PRT
<213> ORGANISM: Ebola virus

<400> SEQUENCE: 44

Ile Met His Asn Gln Asn Gly Leu Ile Cys Gly Leu Arg Gln Leu Ala
1               5                   10                  15

Asn Glu Thr Thr Gln Ala Leu Gln Leu Phe Leu Arg Ala Thr Thr Glu
            20                  25                  30

Leu Arg Thr Phe Ser Ile Leu Asn Arg Lys Ala Ile Asp Phe Leu Leu
        35                  40                  45

Gln Arg
    50

<210> SEQ ID NO 45
<211> LENGTH: 50
<212> TYPE: PRT
<213> ORGANISM: Ebola virus

<400> SEQUENCE: 45

Ile Met Glu Asn Gln Asn Gly Leu Ile Cys Gly Leu Arg Gln Leu Ala
1               5                   10                  15

Asn Glu Thr Thr Gln Ala Leu Gln Leu Phe Leu Arg Ala Thr Thr Glu
            20                  25                  30

Leu Arg Thr Phe Ser Ile Leu Asn Arg Lys Ala Ile Asp Phe Leu Leu
        35                  40                  45

Gln Arg
    50

```
<210> SEQ ID NO 46
<211> LENGTH: 50
<212> TYPE: PRT
<213> ORGANISM: Ebola virus

<400> SEQUENCE: 46

Leu Met His Asn Gln Asp Gly Leu Ile Cys Gly Leu Arg Gln Leu Ala
1               5                   10                  15

Asn Glu Thr Thr Gln Ala Leu Gln Leu Phe Leu Arg Ala Thr Thr Glu
            20                  25                  30

Leu Arg Thr Phe Ser Ile Leu Asn Arg Lys Ala Ile Asp Phe Leu Leu
        35                  40                  45

Gln Arg
    50

<210> SEQ ID NO 47
<211> LENGTH: 50
<212> TYPE: PRT
<213> ORGANISM: Ebola virus

<400> SEQUENCE: 47

Val Met His Asn Gln Asn Gly Leu Ile Cys Gly Leu Arg Gln Leu Ala
1               5                   10                  15

Asn Glu Thr Thr Gln Ala Leu Gln Leu Phe Leu Arg Ala Thr Thr Glu
            20                  25                  30

Leu Arg Thr Tyr Ser Leu Leu Asn Arg Lys Ala Ile Asp Phe Leu Leu
        35                  40                  45

Gln Arg
    50

<210> SEQ ID NO 48
<211> LENGTH: 50
<212> TYPE: PRT
<213> ORGANISM: Ebola virus

<400> SEQUENCE: 48

Leu Met His Asn Gln Asn Ala Leu Val Cys Gly Leu Arg Gln Leu Ala
1               5                   10                  15

Asn Glu Thr Thr Gln Ala Leu Gln Leu Phe Leu Arg Ala Thr Thr Glu
            20                  25                  30

Leu Arg Thr Tyr Thr Ile Leu Asn Arg Lys Ala Ile Asp Phe Leu Leu
        35                  40                  45

Arg Arg
    50

<210> SEQ ID NO 49
<211> LENGTH: 50
<212> TYPE: PRT
<213> ORGANISM: Ebola virus

<400> SEQUENCE: 49

Trp Gly Gly Thr Cys His Ile Leu Gly Pro Asp Cys Cys Ile Glu Pro
1               5                   10                  15

His Asp Trp Thr Lys Asn Ile Thr Asp Lys Ile Asp Gln Ile Ile His
            20                  25                  30

Asp Phe Ile Asp Lys Pro Leu Pro Asp Gln Thr Asp Asn Asp Asn Trp
        35                  40                  45

Trp Thr
    50
```

<210> SEQ ID NO 50
<211> LENGTH: 50
<212> TYPE: PRT
<213> ORGANISM: Ebola virus

<400> SEQUENCE: 50

Trp Gly Gly Thr Cys His Ile Leu Gly Pro Asp Cys Cys Ile Glu Pro
1               5                   10                  15

Gln Asp Trp Thr Lys Asn Ile Thr Asp Lys Ile Asp Gln Ile Ile His
            20                  25                  30

Asp Phe Val Asp Asn Asn Leu Pro Asn Gln Asn Asp Gly Ser Asn Trp
        35                  40                  45

Trp Thr
    50

<210> SEQ ID NO 51
<211> LENGTH: 50
<212> TYPE: PRT
<213> ORGANISM: Ebola virus

<400> SEQUENCE: 51

Trp Gly Gly Thr Cys His Ile Leu Gly Pro Asp Cys Cys Ile Glu Pro
1               5                   10                  15

His Asp Trp Thr Lys Asn Ile Thr Asp Lys Ile Asp Gln Ile Ile His
            20                  25                  30

Asp Phe Val Asp Lys Thr Leu Pro Asp Gln Gly Asp Asn Asp Asn Trp
        35                  40                  45

Trp Thr
    50

<210> SEQ ID NO 52
<211> LENGTH: 50
<212> TYPE: PRT
<213> ORGANISM: Ebola virus

<400> SEQUENCE: 52

Trp Gly Gly Thr Cys Arg Ile Leu Gly Pro Ser Cys Cys Ile Glu Pro
1               5                   10                  15

His Asp Trp Thr Lys Asn Ile Thr Asp Glu Ile Asn Gln Ile Lys His
            20                  25                  30

Asp Phe Ile Asp Asn Pro Leu Pro Asp His Gly Asp Asp Leu Asn Leu
        35                  40                  45

Trp Thr
    50

<210> SEQ ID NO 53
<211> LENGTH: 50
<212> TYPE: PRT
<213> ORGANISM: Ebola virus

<400> SEQUENCE: 53

Trp Gly Gly Thr Cys Arg Ile Leu Gly Pro Asp Cys Cys Ile Glu Pro
1               5                   10                  15

His Asp Trp Thr Lys Asn Ile Thr Asp Lys Ile Asn Gln Ile Ile His
            20                  25                  30

Asp Phe Ile Asp Asn Pro Leu Pro Asn Gln Asp Asn Asp Asp Asn Trp
        35                  40                  45

Trp Thr

<210> SEQ ID NO 54
<211> LENGTH: 46
<212> TYPE: PRT
<213> ORGANISM: Artificial sequence
<220> FEATURE:
<223> OTHER INFORMATION: Synthetic sequence

<400> SEQUENCE: 54

Ser Glu Ala Leu Lys Ile Leu Asn Asn Ile Arg Thr Leu Arg Ala Gln
1               5                   10                  15

Ala Arg Glu Cys Thr Leu Glu Thr Leu Glu Glu Met Leu Glu Lys Leu
            20                  25                  30

Glu Val Val Val Asn Glu Arg Arg Glu Glu Glu Ser Ala Ala
        35                  40                  45

<210> SEQ ID NO 55
<211> LENGTH: 44
<212> TYPE: PRT
<213> ORGANISM: Artificial sequence
<220> FEATURE:
<223> OTHER INFORMATION: Synthetic sequence

<400> SEQUENCE: 55

Met Asn Asp Cys Tyr Ser Lys Leu Lys Glu Leu Val Pro Ser Ile Pro
1               5                   10                  15

Gln Asn Lys Lys Val Ser Lys Met Glu Ile Leu Gln His Val Ile Asp
            20                  25                  30

Tyr Ile Leu Asp Leu Gln Ile Ala Leu Asp Ser His
        35                  40

<210> SEQ ID NO 56
<211> LENGTH: 67
<212> TYPE: PRT
<213> ORGANISM: Artificial sequence
<220> FEATURE:
<223> OTHER INFORMATION: Synthetic sequence

<400> SEQUENCE: 56

Gly His His His His His His Thr Asp Lys Arg Lys Asp Gly Ser Gly
1               5                   10                  15

Lys Leu Leu Tyr Cys Ser Phe Cys Gly Lys Ser Gln His Glu Val Arg
            20                  25                  30

Lys Leu Ile Ala Gly Pro Ser Val Tyr Ile Cys Asp Glu Cys Val Asp
        35                  40                  45

Leu Cys Asn Asp Ile Ile Arg Glu Glu Ile Lys Glu Val Ala Pro His
    50                  55                  60

Arg Glu Arg
65

<210> SEQ ID NO 57
<211> LENGTH: 66
<212> TYPE: PRT
<213> ORGANISM: Artificial sequence
<220> FEATURE:
<223> OTHER INFORMATION: Synthetic sequence

<400> SEQUENCE: 57

Met Glu Lys Arg Pro Arg Thr Glu Phe Ser Glu Glu Gln Lys Lys Ala
1               5                   10                  15

Leu Asp Leu Ala Phe Tyr Phe Asp Arg Arg Leu Thr Pro Glu Trp Arg

```
                    20                  25                  30

Arg Tyr Leu Ser Gln Arg Leu Gly Leu Asn Glu Glu Gln Ile Glu Arg
             35                  40                  45

Trp Phe Arg Arg Lys Glu Gln Gln Ile Gly Trp Ser His Pro Gln Phe
         50                  55                  60

Glu Lys
65

<210> SEQ ID NO 58
<211> LENGTH: 78
<212> TYPE: PRT
<213> ORGANISM: Artificial sequence
<220> FEATURE:
<223> OTHER INFORMATION: Synthetic sequence

<400> SEQUENCE: 58

Asp Gln Pro Ser Val Gly Asp Ala Phe Asp Lys Tyr Asn Glu Ala Val
1               5                   10                  15

Arg Val Phe Thr Gln Leu Ser Ser Ala Ala Asn Cys Asp Trp Ala Ala
                20                  25                  30

Cys Leu Ser Ser Leu Ser Ala Ser Ser Ala Ala Cys Ile Ala Ala Val
             35                  40                  45

Gly Glu Leu Gly Leu Asp Val Pro Leu Asp Leu Ala Cys Ala Ala Thr
         50                  55                  60

Ala Thr Ser Ser Ala Thr Glu Ala Cys Lys Gly Cys Leu Trp
65                  70                  75

<210> SEQ ID NO 59
<211> LENGTH: 90
<212> TYPE: PRT
<213> ORGANISM: Artificial sequence
<220> FEATURE:
<223> OTHER INFORMATION: Synthetic sequence

<400> SEQUENCE: 59

Met Asn Lys Asn Ile Asp Thr Val Arg Glu Ile Ile Thr Val Ala Ser
1               5                   10                  15

Ile Leu Ile Lys Phe Ser Arg Glu Asp Ile Val Glu Asn Arg Ala Asn
                20                  25                  30

Phe Ile Ala Phe Leu Asn Glu Ile Gly Val Thr His Glu Gly Arg Lys
             35                  40                  45

Leu Asn Gln Asn Ser Phe Arg Lys Ile Val Ser Glu Leu Thr Gln Glu
         50                  55                  60

Asp Lys Lys Thr Leu Ile Asp Glu Phe Asn Glu Gly Phe Glu Gly Val
65                  70                  75                  80

Tyr Arg Tyr Leu Glu Met Tyr Thr Asn Lys
                85                  90

<210> SEQ ID NO 60
<211> LENGTH: 60
<212> TYPE: PRT
<213> ORGANISM: Artificial sequence
<220> FEATURE:
<223> OTHER INFORMATION: Synthetic sequence

<400> SEQUENCE: 60

Gly Ser Ala Ala Ser Pro Ala Val Asp Ile Gly Asp Arg Leu Asp Glu
1               5                   10                  15

Leu Glu Lys Ala Leu Glu Ala Leu Ser Ala Glu Asp Gly His Asp Asp
                20                  25                  30
```

```
Val Gly Gln Arg Leu Glu Ser Leu Leu Arg Arg Trp Asn Ser Arg Arg
        35                  40                  45

Ala Asp Ala Pro Ser Thr Ser Ala Ile Ser Glu Asp
    50                  55                  60

<210> SEQ ID NO 61
<211> LENGTH: 46
<212> TYPE: PRT
<213> ORGANISM: Artificial sequence
<220> FEATURE:
<223> OTHER INFORMATION: Synthetic sequence

<400> SEQUENCE: 61

His Met Gly His Ile Gln Ile Pro Pro Gly Leu Thr Glu Leu Leu Gln
1               5                   10                  15

Gly Tyr Thr Val Glu Val Leu Arg Gln Gln Pro Pro Asp Leu Val Asp
            20                  25                  30

Phe Ala Val Glu Tyr Phe Thr Arg Leu Arg Glu Ala Arg Arg
        35                  40                  45

<210> SEQ ID NO 62
<211> LENGTH: 83
<212> TYPE: PRT
<213> ORGANISM: Artificial sequence
<220> FEATURE:
<223> OTHER INFORMATION: Synthetic sequence

<400> SEQUENCE: 62

Met Pro Gln Ile Ser Arg Tyr Ser Asp Glu Gln Val Glu Gln Leu Leu
1               5                   10                  15

Ala Glu Leu Leu Asn Val Leu Glu Lys His Lys Ala Pro Thr Asp Leu
            20                  25                  30

Ser Leu Met Val Leu Gly Asn Met Val Thr Asn Leu Ile Asn Thr Ala
        35                  40                  45

Ile Ala Pro Ala Gln Arg Gln Ala Ile Ala Asn Ser Phe Ala Arg Ala
    50                  55                  60

Leu Gln Ser Ser Ile Asn Glu Asp Lys Ala His Leu Glu His His
65                  70                  75                  80

His His His
```

COMPOSITIONS AND METHODS RELATED TO EBOLAVIRUS VACCINES

CROSS-REFERENCE TO RELATED APPLICATIONS

The subject patent application claims the benefit of priority to U.S. Provisional Patent Application No. 63/063,530 (filed Aug. 10, 2020). The full disclosure of the priority application is incorporated herein by reference in its entirety and for all purposes.

STATEMENT OF GOVERNMENT SUPPORT

This invention was made with government support under AI129698 and AI123861 awarded by the National Institutes of Health. The government has certain rights in the invention.

BACKGROUND OF THE INVENTION

Filoviruses such as Zaire Ebola virus (EBOV) and Marburg virus can cause a lethal hemorrhagic fever in humans and nonhuman primates (NHPs). The virus glycoprotein, GP, mediates cell entry by initiating attachment and membrane fusion. Structures of GP-bound neutralizing antibodies (NAbs) from human survivors demonstrated that GP harbors all NAb epitopes known to date and is the sole target for vaccine design. Like HIV-1 envelope glycoprotein (Env), filovirus GP is metastable and produces non-functional forms when expressed in various cell lines.

A lasting campaign has been undertaken to identify and characterize NAbs for EBOV and other filoviruses such as Marburg virus (MARV). As a result, large panels of NAbs were isolated from human survivors, vaccinated humans, and immunized animals. Crystallography and electron microscopy (EM) have revealed multiple sites of vulnerability on EBOV GP. A recent study of 171 monoclonal antibodies (mAbs) defined eight epitope classes, of which six can be recognized by broadly neutralizing antibodies (bNAbs). While recombinant virus-like particles (VLPs) can protect against EBOV challenge in animals, the difficulties in manufacturing have hampered their further development as human vaccines.

Despite recent advances in the development of medical regimen against filoviruses, there is still a strong need in the art for more effective means for treating and preventing human infections and deaths caused by Ebolaviruses. The instant invention is directed to this and other unmet needs in the art.

SUMMARY OF THE INVENTION

In one aspect, the invention provides engineered or redesigned Ebolavirus glycoprotein (GP) sequences. Relative to a wildtype Ebolavirus GP sequence, the engineered sequences contain (a) a substitution of residue W615 in heptad repeat 2 (HR2) with a smaller hydrophobic residue, and (b) one or more proline substitutions in heptad repeat 1 C segment ($HR1_C$). The amino acid numbering is based on Zaire Ebolavirus GP sequence that has the ectodomain sequence identified by UniProt ID Q05320 (SEQ ID NO:1). In various embodiments, the engineered Ebolavirus GP sequences can be modified or derived from the wildtype GP sequence of a Zaire Ebolavirus (EBOV), a Sudan virus (SUDV), a Taï forest virus (TAFV), a Bundibugyo virus (BDBV), or a Reston Ebolavirus (RESTV).

In some embodiments, residue W615 in the engineered Ebolavirus GP sequences can be replaced with residue L, A, V, I or F. In some embodiments, the proline substitutions in $HR1_C$ include T577P and/or L579P. In some embodiments, the engineered Ebolavirus GP sequences additionally include a truncation at the C-terminus of the membrane proximal external region (MPER). In some of these embodiments, the engineered Ebolavirus GP sequences can further include (a) a deletion of the mucin-like domain (MLD) deleted from the GP1 subunit, and/or (b) a deletion of MPER from the GP2 subunit.

In another aspect, the invention provides engineered Ebolavirus GP sequences that contain (a) a truncated soluble GP of an Ebolavirus that has MLD deleted from the GP1 subunit and MPER deleted from the GP2 subunit, and (b) one or more modifications in the HR2 and HR1 regions. In various embodiments, the additional modifications in the HR2 and HR1 regions can be (i) substitution of W615 in heptad repeat 2 (HR2) with a smaller hydrophobic residue, (ii) an extension of HR2 at the C terminus, (iii) one or more proline substitutions in heptad repeat 1 C segment ($HR1_C$), and (iv) one or more engineered inter-GP disulfide bonds. Again, the amino acid numbering is based on the Zaire Ebolavirus GP sequence with UniProt ID Q05320 (SEQ ID NO:1). In various embodiments, these engineered Ebolavirus GP sequences can be derived from Zaire Ebolaviruses (EBOV), Sudan viruses (SUDV), Taï forest viruses (TAFV), Bundibugyo viruses (BDBV), or Reston Ebolaviruses (RESTV). Some engineered Ebolavirus GP sequences are based on the truncated soluble GP sequence shown in SEQ ID NO:2 or SEQ ID NO:3, or a conservatively modified or substantially identical variant thereof. In some embodiments, the engineered GP sequences can have a N-terminal leader sequence. As exemplification, the N-terminal leader sequence can contain SEQ ID NO:41 or a conservatively modified variant.

Some engineered soluble Ebolavirus GP sequences contain a substitution of residue W615. In some of these embodiments, residue W615 can be replaced with L, A, V, I or F. Some of these engineered Ebolavirus GP proteins contain the amino acid sequence shown in SEQ ID NOs:4, a conservatively modified variant or a substantially identical sequence thereof. In some embodiments, the engineered soluble Ebolavirus GP proteins can contain an extension of HR2 at the C-terminus. In some of these embodiments, the HR2 extension can be (a) extending HR2 C terminus with a N-terminal fragment of adjacent MPER of the Ebolavirus glycoprotein or (b) replacing a HR2 C-terminal fragment with a longer leucine zipper motif. As exemplification, HR2 extension in the engineered soluble Ebolavirus GP proteins can include (a) extension of the HR2 C terminus from residue 632 to residue 637 in MPER, i.e., addition of residues KTLPD (SEQ ID NO:32), (b) extension of the HR2 C terminus from residue 632 to residues 643 in MPER, i.e., addition of residues KTLPDQGDNDN (SEQ ID NO:33), or (c) replacement of residues 617-632 with a GCN4 leucine zipper sequence shown in SEQ ID NO:34.

Some engineered soluble Ebolavirus GP sequences of the invention contain both a HR2 extension noted above and a W615 substitution in HR2. In some of these embodiments, the W615 substitution can be W615L or P612G/W615F double mutation. In some embodiments, the engineered GP sequences contain (a) W615L substitution and (b) extension of the HR2 C terminus from residue 632 to residue 637 in MPER of the Ebolavirus GP. In some other embodiments, the engineered GP sequences contain (a) P612G/W615F double mutation in HR2 and (b) replacement of residues 617-632 with a GCN4 leucine zipper sequence shown in SEQ ID NO:34. Some specific engineered soluble Ebolavirus GP sequences contain an amino acid sequence shown in any one of SEQ ID NOs:5-8, a conservatively modified variant or a substantially identical sequence thereof.

In addition to the HR2 extension and/or the W612 substitution, the engineered GP sequences in some embodiments can also contain a C-terminal trimerization motif. In some of these embodiments, the C-terminal trimerization motif can contain SEQ ID NO:29 or SEQ ID NO:30, or a conservatively modified variant or a substantially identical sequence thereof. In addition to the W612 substitution, the engineered GP sequences in some embodiments can also contain one or more proline substitutions in the $HR1_C$ segment. Any residue in $HR1_C$ can be replaced with a proline residue. In some of these embodiments, the proline substitution comprises T577P or L579P. Some specific examples of engineered Ebolavirus GP sequences having a W612 substitution in HR2 and a proline substitution in $HR1_C$ contain an amino acid sequence as set forth in any one of SEQ ID NOs:9-16, a conservatively modified variant or a substantially identical sequence thereof.

Some engineered GP sequences of the invention contain a HR2 extension, a proline substitution in $HR1_C$, and a substitution at residue W615. In some of these embodiments, the W615 residue can be replaced with L, A, V, I or F. In some of the embodiments, the engineered Ebolavirus GP sequences contain an extension of HR2 C terminus from residue 632 to residue 637 in MPER. Some specific examples of such engineered Ebolavirus GP sequences contain an amino acid sequence as set forth in any one of SEQ ID NOs:17 and 20, a conservatively modified variant or a substantially identical sequence thereof. In some of the embodiments, the engineered Ebolavirus GP sequences can further include a C-terminal trimerization motif. For example, the engineered Ebolavirus GP proteins can include the C-terminal trimerization motif shown in SEQ ID NO:29 or SEQ ID NO:30, or a conservatively modified variant or a substantially identical sequence thereof.

Some engineered Ebolavirus GP sequences contain (a) W615L substitution, (b) proline substitution T577P or L579P, and (c) HR2 extension from residue 632 to residue 637 in MPER. Some specific examples of these engineered Ebolavirus GP sequences contain amino acid sequence as set forth in any one of SEQ ID NOs:18, 19, 21 and 22, a conservatively modified variant or a substantially identical sequence thereof.

Some engineered Ebolavirus GP sequences contain one or more engineered disulfide bonds between two neighboring GP protomers. In various embodiments, the engineered disulfide bonds scan be created by cysteine substitutions at residue pairs G91/A575 (SS2), F153/Y534 (SS1), T520/A575 (SS3), G157/I532 (SS4), D522/A575 (SS5), and/or K56/G599 (SS6). Some specific examples of these engineered Ebolavirus GP sequences have an amino acid sequence are shown in any one of SEQ ID NOs:23-28, a conservatively modified variant or a substantially identical sequence thereof.

In some related aspects, the invention provides nucleic acid or polynucleotide sequences that encode an engineered full length or truncated Ebolavirus GP protein sequence described herein. Some engineered Ebolavirus GP sequences also contain a leader peptide encoding sequence at the 5'. Also provided in the invention are pharmaceutical compositions that contain an engineered Ebolavirus GP protein or encoding polynucleotide sequence described herein, and a pharmaceutically acceptable carrier.

In another aspect, the invention provides vaccine compositions that contain an engineered Ebolavirus GP protein that is displayed on the surface of a self-assembling nanoparticle. In some embodiments, C-terminus of the engineered Ebolavirus GP protein is fused to the N-terminus of subunit of the self-assembling nanoparticle (NP). In some embodiments, C-terminus of the engineered Ebolavirus GP protein is fused to the subunit of the self-assembling nanoparticle via a linker sequence GGGGS (SEQ ID NO=76, #r $(GGGGS)_2$ (SEQ ID NO:42). In some embodiments, the engineered Ebolavirus GP proteins in the NP vaccine compositions contain an amino acid sequence as set forth in any one of SEQ ID NOs:4-28, a conservatively modified variant or a substantially identical sequence thereof. In some embodiments, subunit of the self-assembling nanoparticle contains the polypeptide sequence as shown in SEQ ID NO:36 (E2p), SEQ ID NO:37 (I3-01v9), or SEQ ID NO:38 (ferritin), a conservatively modified variant or a substantially identical sequence thereof.

Some NP scaffolded vaccine compositions of the invention can additionally contain a locking domain (LD) that is fused to the C terminus of the NP subunit sequence. In some of these embodiments, the employed LD contains the sequence shown in SEQ ID NO:39 or 40, a conservatively modified variant or a substantially identical sequence thereof. Some of the scaffolded vaccines can additionally contain a T-cell epitope that is fused to the C-terminus of the locking domain. In some of these embodiments, the employed T-cell epitope contains the sequence shown in SEQ ID NO:31, a conservatively modified variant or a substantially identical sequence thereof.

Some NP vaccine compositions of the invention contain (1) a polypeptide sequence containing from N terminus to C terminus (a) an engineered Ebolavirus GP protein, linker sequence $G_4S$ (SEQ ID NO:43), nanoparticle sequence ferritin, (b) an engineered Ebolavirus GP protein, linker sequence $G_4S$ (SEQ ID NO:43), nanoparticle sequence E2p, or (c) an engineered Ebolavirus GP protein, linker sequence $(G_4S)_2$ (SEQ ID NO:42), nanoparticle sequence I3-01v9; or (2) a conservatively modified variant of the polypeptide sequence of (1). In some of these embodiments, the engineered Ebolavirus GP sequences contain W615L substitution, proline substitution T577P, and HR2 extension from residue 632 to residue 637 in MPER. These engineered Ebolavirus GP sequences can additionally contain a locking domain and/or a T-cell epitope that is fused to the C-terminus of the nanoparticle subunit sequence. In some embodiments, the vaccine compositions contain (1) a polypeptide sequence containing from N-terminus to C-terminus (a) the engineered Ebolavirus GP protein shown in SEQ ID NO:17, nanoparticle subunit sequence shown in SEQ ID NO:36 (E2p), locking domain shown in SEQ ID NO:39 (LD4), and T cell epitope shown in SEQ ID NO:31 (PADRE) or (b) the engineered Ebolavirus GP protein shown in SEQ ID NO:17, nanoparticle sequence shown in SEQ ID NO:37 (I3-01v9), locking domain shown in SEQ ID NO:40 (LD7), or (2) a conservatively modified variant of the polypeptide sequence.

A further understanding of the nature and advantages of the present invention may be realized by reference to the remaining portions of the specification and claims.

DESCRIPTION OF THE DRAWINGS

FIG. 1 shows (A) a schematic structure of Ebolavirus glycoproteins (GPs) and (B) the general redesign strategy for generating engineered Ebolavirus GP vaccine immunogen proteins of the invention.

FIG. 2 shows sequence alignment of the H1 (SEQ ID NOs:44-48) and HR2 (SEQ ID NOs:49-53) regions of the glycoproteins (GPs) of randomly selected strains from all 5 Ebolavirus species, Bundibugyo Ebolavirus (AYI50316), Zaire Ebolavirus (AER59712), Reston Ebolavirus (ASU06443), Sudan Ebolavirus (ALH21228) and Tai Forest Ebolavirus (AWK96625).

FIG. 4 shows design and characterization of multilayered EBOV GPΔmuc-presenting NPs. (A) Locking domains (LD) identified from the Protein Data Bank (PDB) for stabilizing the NP-forming interface. Shown in the figure are the PDB IDs of the identified LDs and their full sequences (SEQ ID NOs:54-62). Residues deleted at the N- and/or C-termini of the original sequences for generating actual LDs used in the studies herein are noted in the sequences. (B)-(C) Antigenic evaluation by ELISA. Binding of FR and reengineered E2p (E2p-LD4-PADRE, or E2p-L4P) and I3-01 (I3-01-LD7-PADRE, I3-01-L7P) NPs that present a stabilized GPΔmuc-$WL^2P^2$ trimer to 10 antibodies with ELISA curves shown in (B) and $EC_{50}$ values summarized in (C). All GP-NPs were expressed transiently in ExpiCHO cells, purified by a mAb100 column, and further purified by SEC on a Superose 6 10/300 GL column. (D)-(G) Antigenic evaluation by BLI using Octet96. Binding kinetics of GPΔmuc-$WL^2P^2$-foldon (D) and GPΔmuc-$WL^2P^2$ on FR (E), E2p-L4P (F), and I3-01-L7P (G) NPs to 10 antibodies. BLI sensorgrams were obtained from an Octet RED96 instrument using a series of six concentrations (400-12.5 nM by twofold dilution for GPΔmuc; 25-0.78 nM and 10-0.31 nM by twofold dilution for FR and E2p-L4p/I3-01-L7P, respectively) and quantitation biosensors (see Materials and Methods). (H) SEC profile of GPΔmuc-$WL^2P^2$-10GS-I3-01v9-LD7. I3-01v9 is a variant of I3-01 with a redesigned NP-forming interface based on the PDB structure (1VLW). I3-01v9 was reported in our previous study with a construct name "1VLW-V9".

FIG. 5 shows immunogenicity assessment of EBOV GP/GPΔmuc trimers and GPΔmuc-presenting NPs in BALB/c mice. (A) ELISA binding curves of mouse serum from three trimer groups, in which mice were immunized with WT GP-foldon, GPΔMuc-foldon, and GPΔMuc-$WL^2P^2$-fold trimers, and three NP groups, in which mice were immunized with FR, E2p-L4P, and I3-01v9-L7P NPs presenting GPΔMuc-$WL^2P^2$, to GPΔMuc-$WL^2P^2$ at w2, w5, w8, and w11. (B) $EC_{50}$ titers measured for the three trimer groups. (C) $EC_{50}$ titers measured for the three NP groups. The $EC_{50}$ titer was measured in the unit of fold of dilution. Of note, serum binding at w2 did not reach the plateau (or saturation) to allow for accurate determination of $EC_{50}$ titers. Nonetheless, the $EC_{50}$ values calculated in Prism were used as a quantitative measure of binding antibody titers to facilitate the comparison of different vaccine groups at w2. (D) Ebolavirus-pp (Makona C15) neutralization by 10 Ebolavirus-specific antibodies in TZM-bl cells. (E) MLV-pp neutralization by 10 Ebolavirus-specific antibodies in 293 T cells. (F) MLV-pp neutralization by purified mouse serum IgGs in 293 T cells. Mouse IgGs were collected from all six vaccine groups at w11.

FIG. 6 shows immunogenicity assessment of EBOV GP/GPΔmuc trimers and GPΔmuc-presenting NPs in rabbits. (A) ELISA binding curves of rabbit serum from two trimer groups, in which rabbits were immunized with GPΔMuc-foldon and GPΔMuc-$WL^2P^2$-fold trimers, and three NP groups, in which rabbits were immunized with FR, E2p-L4P, and I3-01v9-L7P NPs presenting GPΔMuc-$WL^2P^2$, to GPΔMuc-$WL^2P^2$ at w0, w2, w5, w8, w11, and w13. (B) $EC_{50}$ titers measured for the two trimer groups and three NP groups. The $EC_{50}$ titer was measured in the unit of fold of dilution. Of note, serum binding at w2 did not reach the plateau (or saturation) but the $OD_{45}0$ values were approximately at the same level as those obtained at w5 (fully plateaued). Therefore, the $EC_{50}$ values calculated in Prism were considered sufficiently accurate to facilitate the comparison of different vaccine groups at w2. Ebolavirus-pp (EBOV-Makona and BDBV) and MLV-pp neutralization by purified rabbit IgGs from w2, w5, and w8 in 293 T cells is shown in (C), (D), (E) and (F). Data points that do not fit a sigmodal dose response model are shown as dashed lines. The signs of ADE for the two GPΔmuc trimer groups, the FR group, and the two multilayered 60-meric NP groups are w2, w5, and w8, respectively, which are highlighted in dashed rectangles.

DETAILED DESCRIPTION

I Overview

Figure 3:
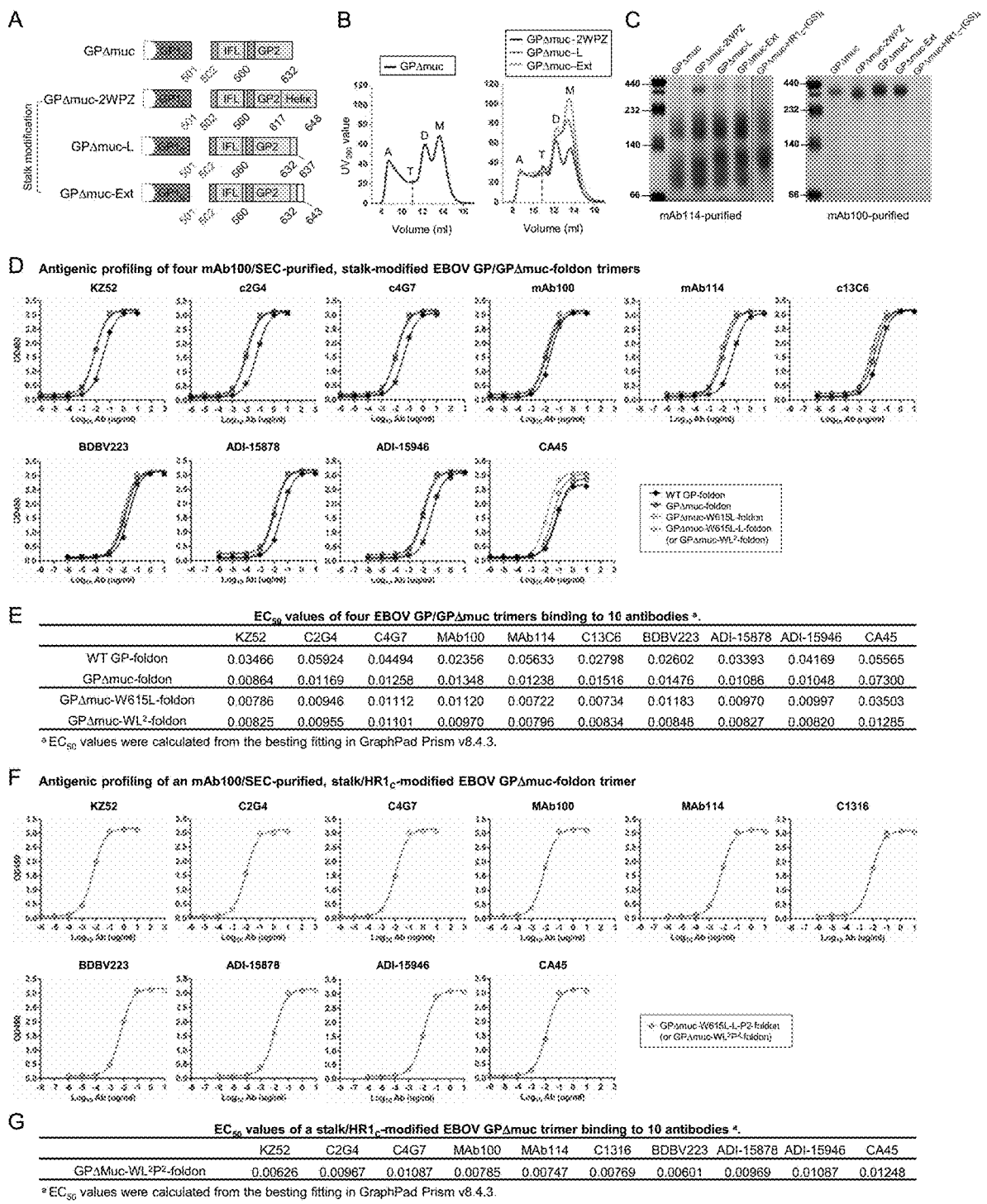
FIG. 3 shows design, screening, and antigenic characterization of EBOV GPΔmuc trimers with modified stalk and $HR1_C$. (A) Schematic representation of a mucin-deleted GP (GPΔmuc) and three stalk designs (GPΔmuc-2WPZ, GPΔmuc-L, and GPΔmuc-Ext). (B) SEC profiles of four GPΔmuc constructs obtained from a Superdex 200 10/300 column following transient expression in 250 ml HEK293 F cells and mAb114 purification. Left: the SEC curve of GPΔmuc shown in black line; Right: three stalk designs shown for GPΔmuc-2WPZ, -L, and -Ext, respectively. (C) BN-PAGE of GPΔmuc proteins purified by mAb114 (left) and mAb110 (right) columns. Of note, an additional GPΔmuc construct with the 8-aa $HR1_C$ replaced by a flexible $(GS)_4$ loop is included for comparison. (D) ELISA curves of four mAb100/SEC-purified, stalk-modified EBOV GP/GPΔmuc-foldon trimers binding to 10 antibodies. (E) Summary of $EC_{50}$ values (μg/ml) of EBOV GP/GPΔmuc-foldon trimers binding to 10 antibodies. (F) ELISA curves of an mAb100/SEC-purified, stalk/$HR1_C$-modified EBOV GPΔmuc-foldon trimer binding to 10 antibodies. (G) Summary of $EC_{50}$ values (μg/ml) of a stalk/$HR1_C$-modified EBOV GPΔmuc-foldon trimer binding to 10 antibodies. (H) Plot of $EC_{50}$ (μg/ml) values of five GP/GPΔmuc-foldon trimers binding to 10 antibodies. Four pan-Ebolavirus NAbs are indicated. In (E) and (G), $EC_{50}$ values were calculated for all ELISA data in Prism version 8.4.3.

Ebolaviruses can cause severe hemorrhagic fever. There are five virus species in the Ebolavirus genus, Ebola virus (aka Zaire Ebolavirus; EBOV), Sudan virus (SUDV), Taï forest virus (TAFV), Bundibugyo virus (BDBV), and Reston Ebolavirus (RESTV). Of these, EBOV, SUDV, TAFV and BDBV all have pandemic potential in humans. For example, EBOV was solely responsible for the largest filovirus outbreak in history during 2013-2016, which spread across nine African countries with 28,600 cases and 11,325 deaths. A previous EBOV outbreak led to 2103 deaths and was declared an international emergency on Jul. 17, 2019 by the World Health Organization (WHO). In recent years, significant progress has been made to counter this deadly virus. Neutralizing antibodies (NAbs) have now been established as effective therapeutics for EBOV infection. Vaccines based on diverse delivery systems have been tested in humans. rVSV-ZEBOV, a replication-competent recombinant vesicular stomatitis virus (VSV) expressing a Zaire EBOV glycoprotein (GP), is the most advanced vaccine candidate that was deployed during the 2018-2019 outbreak. However, GP-specific antibody titers were not noticeably increased seven days after vaccination with rVSV-ZEBOV in humans, contrasting prior findings in nonhuman primates (NHPs). In addition, a recent study reported the neurotropism of rVSV-ZEBOV which caused damage to the eye and brain in neonatal mice. Antibody-dependent enhancement (ADE) of infection was found for EBOV antibodies isolated from human survivors, suggesting that weak or non-NAbs induced by a suboptimal vaccine may cause adverse effects. Currently, no EBOV vaccine has been approved by the U.S. Food and Drug Administration (FDA) for use in humans.

The Ebola virus (EBOV) glycoprotein (GP) can be recognized by neutralizing antibodies (NAbs) and is the main target for vaccine design. The present invention is derived in part from the inventors' studies to rationally redesign the Ebola virus glycoprotein and engineer single-component multilayered nanoparticles as vaccine candidates. As detailed herein, the inventors explored the causes of EBOV GP metastability and designed multilayered NP vaccines for in vivo evaluation. To facilitate GP purification, the inventors developed an immunoaffinity column based on mAb100 that is specific for native-like, trimeric GP. The inventors first examined the contribution of two regions in GP2, namely, the HR2 (the "stalk") region and the heptad repeat 1 C ($HR1_C$) segment, to GP metastability in a mucin-deleted Zaire EBOV GP construct (GPΔmuc). The inventors extended the HR2 stalk to residue 637 and introduced a W615L mutation based on the comparison of EBOV and MARV GPs. The inventors assessed the ability of proline mutation in $HR1_C$ to prevent GP refolding from pre- to post-fusion conformational changes. While both stalk and $HR1_C$-proline mutations increased the trimer yield, the latter appeared to exhibit a complex effect on GP thermostability. Inter-GP molecule disulfide bonds (SS) were also found to increase the trimer stability. Crystal structures were determined for two redesigned GPΔmuc constructs to validate the stalk and $HR1_C$-proline mutations at the atomic level. The inventors then displayed a redesigned GPΔmuc trimer on ferritin, E2p, and I3-01 NPs. Locking domains (LD) and helper T-cell epitopes were incorporated into E2p and I3-01 60-mers to stabilize the NP shell from the inside and to create multilayered NP carriers.

In mice and rabbits, it was observed that the GP trimers and NPs can induce distinct antibody responses. Next-generation sequencing (NGS) of GP-specific B cells showed different profiles for NPs presenting large trimeric spikes versus presenting small antigens such as hepatitis C virus (HCV) E2 core. These studies demonstrate the critical factors of EBOV GP metastability, enable two single-component multilayered self-assembling NPs for designing VLP-type vaccines, and provide EBOV vaccine candidates that warrant further evaluation in NHPs and humans.

In accordance with these studies, the invention provides novel engineered Ebolavirus GP sequences that contain the various modifications disclosed herein. Some embodiments of the invention are directed to immunogen polypeptides and polynucleotide vaccines that are derived from the redesigned Ebolavirus GP sequences described herein. Also provided in the invention are Ebolavirus vaccine compositions containing a displaying platform, including a self-assembling nanoparticle, that displays one or more of the engineered Ebolavirus GP immunogens. Therapeutic applications of the engineered Ebolavirus GP immunogen polypeptides and the related nanoparticle vaccine compositions, e.g., treating or preventing Ebolavirus infections, are also provided in the invention.

Unless otherwise specified herein, the vaccine immunogens of the invention, the encoding polynucleotides, expression vectors and host cells, as well as the related therapeutic applications, can all be generated or performed in accordance with the procedures exemplified herein or routinely practiced methods well known in the art. See, e.g., Methods in Enzymology, Volume 289: Solid-Phase Peptide Synthesis, J. N. Abelson, M. I. Simon, G. B. Fields (Editors), Academic Press; 1st edition (1997) (ISBN-13: 978-0121821906); U.S. Pat. Nos. 4,965,343, and 5,849,954; Sambrook et al., Molecular Cloning: A Laboratory Manual, Cold Spring Harbor Press, N.Y., ($3^{rd}$ ed., 2000); Brent et al., Current Protocols in Molecular Biology, John Wiley & Sons, Inc. (ringbou ed., 2003); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998). The following sections provide additional guidance for practicing the compositions and methods of the present invention.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press ($1^{st}$ ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons ($3^{rd}$ ed., 2002); *Dictionary of Chemistry*, Hunt (Ed.), Routledge ($1^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology (Oxford Paperback Reference)*, Martin and Hine (Eds.), Oxford University Press (4$^{th}$ ed., 2000). Further clarifications of some of these terms as they apply specifically to this invention are provided herein.

As used herein, the singular forms "a," "an," and "the," refer to both the singular as well as plural, unless the context clearly indicates otherwise. For example, "an Env-derived trimer" can refer to both single or plural Env-derived trimer molecules, and can be considered equivalent to the phrase "at least one Env-derived trimer."

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein. Unless otherwise noted, the term "vaccine immunogen" is used interchangeably with "protein antigen" or "immunogen polypeptide".

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For polypeptide sequences, "conservatively modified variants" refer to a variant which has conservative amino acid substitutions, amino acid residues replaced with other amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Epitope refers to an antigenic determinant. These are particular chemical groups or peptide sequences on a molecule that are antigenic, such that they elicit a specific immune response, for example, an epitope is the region of an antigen to which B and/or T cells respond. Epitopes can be formed both from contiguous amino acids or noncontiguous amino acids juxtaposed by tertiary folding of a protein.

Effective amount of a vaccine or other agent that is sufficient to generate a desired response, such as reduce or eliminate a sign or symptom of a condition or disease, such as a viral infection. For instance, this can be the amount necessary to inhibit viral replication or to measurably alter outward symptoms of the viral infection. In general, this amount will be sufficient to measurably inhibit virus (for example, an Ebolavirus) replication or infectivity. When administered to a subject, a dosage will generally be used that will achieve a target concentration that has been shown to be sufficient for in vitro inhibition of viral replication. In some embodiments, an "effective amount" is one that treats (including prophylaxis) one or more symptoms and/or underlying causes of any of a disorder or disease, for example to treat Ebolavirus infection. In some embodiments, an effective amount is a therapeutically effective amount. In some embodiments, an effective amount is an amount that prevents one or more signs or symptoms of a particular disease or condition from developing, such as one or more signs or symptoms associated with an Ebolavirus infection.

As used herein, a fusion protein is a recombinant protein containing amino acid sequence from at least two unrelated proteins that have been joined together, via a peptide bond, to make a single protein. The unrelated amino acid sequences can be joined directly to each other or they can be joined using a linker sequence. As used herein, proteins are unrelated, if their amino acid sequences are not normally found joined together via a peptide bond in their natural environment(s) (e.g., inside a cell). For example, the amino acid sequences of bacterial enzymes such as *B. stearothermophilus* dihydrolipoyl acyltransferase (E2p) and the amino acid sequences of Ebolavirus GP are not normally found joined together via a peptide bond.

The term "Ebolavirus", refers to members of the family Filoviridae, which are associated with outbreaks of highly lethal hemorrhagic fever in humans and nonhuman primates. Human Ebolavirus pathogens include Ebola virus (EBOV), Sudan virus (SUDV), Bundibugyo virus (BDBV), and Taï Forest virus (TAFV). Reston virus (RESTV) is a monkey pathogen and is not currently considered a human pathogen. The natural reservoir of the Ebolaviruses is unknown, and there are currently no available vaccines or effective therapeutic treatments for Ebolavirus infections. The Ebolavirus genome consists of a single strand of negative sense RNA that is approximately 19 kb in length. This RNA contains seven sequentially arranged genes that produce 8 mRNAs upon infection. Ebola virions contain seven proteins: a surface glycoprotein (GP), a nucleoprotein (NP), four virion structural proteins (VP40, VP35, VP30, and VP24), and an RNA-dependent RNA polymerase (L) (Feldmann et al. (1992) Virus Res. 24, 1-19; Sanchez et al., (1993) Virus Res. 29, 215-240; reviewed in Peters et al. (1996) In Fields Virology, Third ed. pp. 1161-1176. Fields, B. N., Knipe, D. M., Howley, P. M., et al. eds. Lippincott-Raven Publishers, Philadelphia).

The term "Ebolavirus glycoprotein (GP)" refers to the only surface antigen of Ebolaviruses that is expressed as a trimer on the viral surface. It is unusual in that it is encoded in two open reading frames. Transcriptional editing is needed to express the transmembrane form that is incorporated into the virion (Sanchez et al. (1996) Proc. Natl. Acad. Sci. USA 93, 3602-3607; Volchkov et al, (1995) Virology 214, 421-430). The unedited form produces a nonstructural secreted glycoprotein (sGP) that is synthesized in large amounts early during the course of infection. The GP of Ebolaviruses is a transmembrane glycoprotein (GP) that is responsible for both receptor binding and membrane fusion. During assembly of the virus, the glycoprotein undergoes proteolytic cleavage by host proteases such as furin, resulting in the two subunits, GP1 and GP2, which are linked by a disulfide bond. The GP1 subunit (amino acids 33-501) contains the core of the glycoprotein, receptor binding domain (RBD), a glycan cap, and a large mucin-like domain (MLD) which extends around the RBD. The GP2 (amino acids 502-676) subunit contains the internal fusion loop (IFL), heptad repeats 1 and 2 (HR1 and HR2), the membrane-proximal external region (MPER), the transmembrane region (TM), and the cytoplasmic tail (CT). During the transport of Ebolavirus particles to late endosomes, low pH leads to proteolytic processing of GPs by host cysteine proteases such as cathepsins, and the exposed receptor binding site of the proteolytically digested GP is thought to interact with a host receptor, Niemann Pick C1, followed by membrane fusion. Unless otherwise noted, amino acid residue numbering of the GP from Zaire Ebolavirus strain Mayinga-76 is used herein as the reference, which has a complete genome sequence identified by GenBank ID of AF272001. Its GP ectodomain sequence (UniProt ID Q05320; GenBank ID AAG40168.1) is shown in SEQ ID NO:1 herein.

As used herein, corresponding residues refers to residues that occur at aligned loci. Related or variant polypeptides are aligned by any method known to those of skill in the art. Such methods typically maximize matches, and include methods such as using manual alignments and by using the numerous alignment programs available (for example, BLASTP) and others known to those of skill in the art. By aligning the sequences of polypeptides, one skilled in the art can identify corresponding residues, using conserved and identical amino acid residues as guides. For example, by aligning the sequences of GP polypeptides from different Ebolavirus species or different isolates of the same species, one of skill in the art can identify corresponding residues, using conserved and identical amino acid residues as guides. Corresponding positions also can be based on structural alignments, for example by using computer simulated alignments of protein structure.

Immunogen as used herein refers to a protein or a portion thereof that is capable of inducing an immune response in a mammal, such as a mammal infected or at risk of infection with a pathogen. Administration of an immunogen can lead to protective immunity and/or proactive immunity against a pathogen of interest.

Immune response refers to a response of a cell of the immune system, such as a B cell, T cell, or monocyte, to a stimulus. In some embodiment, the response is specific for a particular antigen (an "antigen-specific response"). In some embodiments, an immune response is a T cell response, such as a CD4+ response or a CD8+ response. In some other embodiments, the response is a B cell response, and results in the production of specific antibodies.

Immunogenic composition refers to a composition comprising an immunogenic polypeptide that induces a measurable CTL response against virus expressing the immunogenic polypeptide, or induces a measurable B cell response (such as production of antibodies) against the immunogenic polypeptide.

Sequence identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

Homologs or orthologs of nucleic acid or amino acid sequences possess a relatively high degree of sequence identity/similarity when aligned using standard methods. Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The term "subject" refers to any animal classified as a mammal, e.g., human and non-human mammals. Examples of non-human animals include dogs, cats, cattle, horses, sheep, pigs, goats, rabbits, and etc. Unless otherwise noted, the terms "patient" or "subject" are used herein interchangeably. Preferably, the subject is human.

The term "treating" or "alleviating" includes the administration of compounds or agents to a subject to prevent or delay the onset of the symptoms, complications, or biochemical indicia of a disease (e.g., an Ebolavirus infection), alleviating the symptoms or arresting or inhibiting further development of the disease, condition, or disorder. Subjects in need of treatment include those already suffering from the disease or disorder as well as those being at risk of developing the disorder. Treatment may be prophylactic (to prevent or delay the onset of the disease, or to prevent the manifestation of clinical or subclinical symptoms thereof) or therapeutic suppression or alleviation of symptoms after the manifestation of the disease.

Vaccine refers to a pharmaceutical composition that elicits a prophylactic or therapeutic immune response in a subject. In some cases, the immune response is a protective immune response. Typically, a vaccine elicits an antigen-specific immune response to an antigen of a pathogen, for example a viral pathogen, or to a cellular constituent correlated with a pathological condition. A vaccine may include a polynucleotide (such as a nucleic acid encoding an Ebolavirus GP polypeptide disclosed herein), a peptide or polypeptide (such as an Ebolavirus GP polypeptide disclosed antigen), a virus, a cell or one or more cellular constituents. In some embodiments of the invention, vaccines or vaccine immunogens or vaccine compositions are expressed from fusion constructs and self-assemble into nanoparticles displaying an immunogen polypeptide or protein on the surface.

Virus-like particle (VLP) refers to a non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. See, for example, Baker et al. (1991) Biophys. J. 60:1445-1456; and Hagensee et al. (1994) J. Virol. 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

A self-assembling nanoparticle refers to a ball-shape protein shell with a diameter of tens of nanometers and well-defined surface geometry that is formed by identical copies of a non-viral protein capable of automatically assembling into a nanoparticle with a similar appearance to VLPs. Known examples include ferritin (FR), which is conserved across species and forms a 24-mer, as well as *B. stearothermophilus* dihydrolipoyl acyltransferase (E2p), *Aquifex aeolicus* lumazine synthase (LS), and *Thermotoga maritima* encapsulin, which all form 60-mers. Self-assembling nanoparticles can form spontaneously upon recombinant expression of the protein in an appropriate expression system. Methods for nanoparticle production, detection, and characterization can be conducted using the same techniques developed for VLPs.

III. Engineered Ebolavirus GP Sequences

Figure 1:
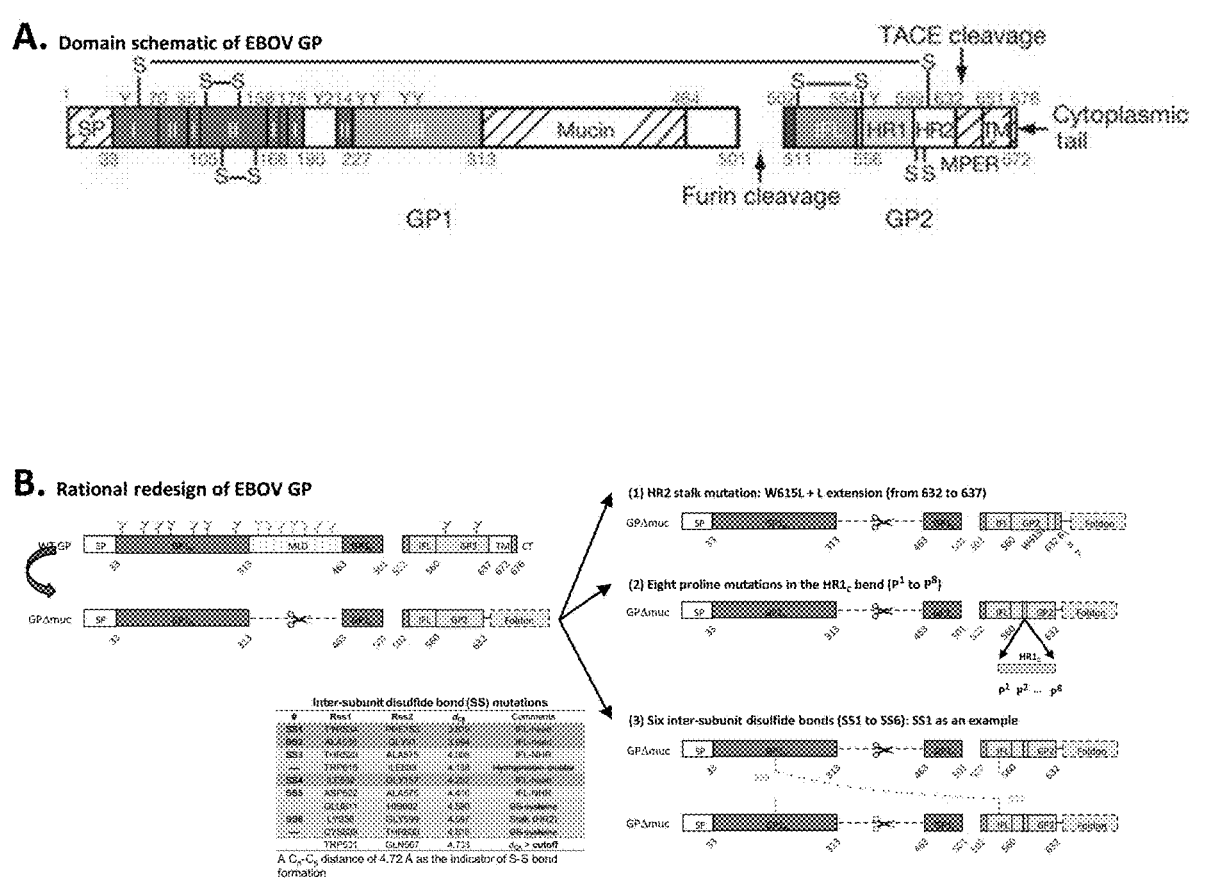

The invention provides engineered or redesigned Ebolavirus glycoprotein (GP) sequences (polypeptides or polynucleotide sequences) for producing Ebolavirus vaccines. Relative to the wildtype GP sequences, these engineered GP polypeptides can contain various modifications, esp. in the GP2 subunit. The GP2 subunit of Ebolavirus GPs contains the N-terminal peptide, the internal fusion loop, two consecutive two heptad repeat regions (HR1 and HR2), the membrane proximal external region (MPER), and the C-terminal transmembrane domain (see FIG. 1A). HR1 is in turn structurally divided into 4 segments, $HR1_A$, $HR1_B$, $HR1_C$ and $HR1_D$. The first two segments, $HR1_A$ and $HR1_B$ (residues 554-575), form an α-helix with an approximately 40° kink at Thr565, which delineates $HR1_A$ from $HR1_B$. $HR1_C$ forms an extended coil linker between $HR1_B$ and the $HR1_D$ segment. $HR1_D$ forms an amphipathic helix, the hydrophobic faces of the three helices in the trimer pack together to form the interface of the peplomer. $HR1_C$ and $HR1_D$ were first defined to correspond to residues 576-582 and residues 583-598, respectively (Lee et al., Future Virol. 2009; 4: 621-635). Based on a higher-resolution and more complete crystal structure of GP reported in Zhao et al. Nature 535, 169-172, 2016, $HR1_C$ is redefined herein to encompass aa576-583, and $HR1_D$ refers to aa 584-598. HR2 is a largely alpha-helical section of protein, also termed the "HR2 stalk", that connects the GP core to the viral membrane. In the EBOV sequence, the HR2 stalk encompasses amino acid residues 599-632.

As detailed herein, the engineered Ebolavirus GP polypeptides contain various mutations or modifications primarily in and around the $HR1_C$ and HR2 motifs (FIG. 1B). Unless otherwise noted, the organization and amino acid numbering with regard to various domains or regions of Ebolavirus GP is based on GP sequence of Zaire Ebolavirus strain Mayinga-76, which has ectodomain sequence described by GenBank ID AAG40168.1 (SEQ ID NO:1). Due to substantial sequence conservation in the structural motifs among the different Ebolaviruses and different strains of the same Ebolavirus species, corresponding amino acid residues bordering the various domains, regions and loops of an Ebolavirus GP from any other Ebolavirus and strains can be readily determined (e.g., by sequence alignment) or otherwise known in the art. As exemplification, a sequence alignment of the HR1 and HR2 regions of EBOV with other Ebolaviruses are shown in FIG. 2. Sequences of the whole HR1+HR2 region are about 84.8% identical across the 5 different species of Ebolaviruses, EBOV, SUDV, TAFV, BDBV and RESTV. As indicated in the figure, residues in the $HR1_C$ segment are highly conserved among the different Ebolaviruses. The first few N-terminal residues in the MPER motif for HR2 extension as described herein are also highly conserved among the different Ebolavirus species. The W615 residue exemplified herein for substitution is conserved in all Ebolavirus species. Moreover, logo analysis of sequence conservation for HR2 stalk described in the Examples below showed that W615 is 100% conserved across all strains of all six species in the Ebolavirus genus. Thus, it is apparent that the Ebolavirus GP sequence modification exemplified with EBOV can be readily applied to other Ebolavirus species and different strains of the same virus species.

Compared to a full length wildtype Ebolavirus GP (see, e.g., FIG. 1A), the engineered Ebolavirus GP sequences of the invention typically contain, in addition to the mutations or modifications described herein, structural motifs that correspond to the GP ectodomain without the N-terminal leader, MLD and MPER (see, e.g., SEQ ID NO:2). In various embodiments, the engineered Ebolavirus GP sequences of the invention can include additional structural motifs or domains of the full length GP beyond the structural components present in SEQ ID NO:2. Thus, some engineered Ebolavirus GP sequences of the invention can additionally contain one or more of (1) a leader sequence, (2) part or all of MLD, (3) part of all of MPER, (4) part or all of the transmembrane domain, and (5) part or all of the cytoplasmic tail.

Some embodiments of the invention are directed to the engineered Ebolavirus GP sequences that correspond to full length Ebolavirus GPs with one or more stabilizing modifications or mutations in the HR2 and HR1 regions described herein. In some embodiments, the engineered Ebolavirus GP sequences can contain substitution at residue W615 in HR2 of a wildtype GP sequence. In some of these embodiments, the W615 residue can be replaced with a small hydrophobic residue, e.g., L, A, V, I or F. Additionally or alternatively, the engineered Ebolavirus GP sequences can have one or more proline substitutions in the $HR1_C$ segment. As exemplified herein, any residue in the $HR1_C$ segment, T576, T577, E578, L579, R580, T581, F582 and S583, can be substituted with proline. In some of these embodiments, the engineered Ebolavirus GP sequences contain T577P and/or L579P substitutions in $HR1_C$. In some embodiments, further cysteine substitutions can be introduced into the GP sequence to generate inter-GP disulfide bonds as exemplified herein. In various embodiments, the leader peptide sequence at the N-terminus of the GP sequences can be removed. In some other embodiments directed to polynucleotide sequences or vectors that express the engineered Ebolavirus GP proteins, a sequence that encodes the leader peptide (e.g., SEQ ID NO:41) is included at the 5'-end of the engineered Ebolavirus GP polynucleotide sequence.

In some embodiments, the engineered Ebolavirus GP sequences of the invention contain only the ectodomain (i.e., MPER at the C-terminus) or otherwise a soluble portion of Ebolavirus GP proteins along with the alterations in the HR1 and HR2 regions described herein. In some of these embodiments, the truncated or altered soluble Ebolavirus GP sequence also has MLD deleted. In some embodiments, the shortened soluble GP sequence additionally has MPER at the C-terminus of the GP ectodomain removed. In various embodiments, the expressed and assembled trimer protein also does not contain the leader peptide sequence (SEQ ID NO:41). An example of such a shortened GP soluble sequence based on a Zaire Ebolavirus (EBOV) GP ectodomain sequence (SEQ ID NO:1) is shown in SEQ ID NO:2, which has the leader, MLD and MPER sequences deleted from the wildtype ectodomain sequence. In some of embodiments, the shortened soluble GP sequence further contains a T42A mutation in the GP1 base motif (GPΔmuc; SEQ ID NO:3).

In addition to the truncation at the C-terminus, engineered soluble Ebolavirus GP sequences of the invention typically contain additional sequence modifications in the HR1 and HR2 regions of a soluble GP sequence (e.g., SEQ ID NO:2 or 3). In various embodiments, the additional sequence modifications include substitution of residue W615 in HR2, extension of HR2 by (1) adding one or more adjacent residues in the MPER or (2) replacing some C-terminal HR2 residues with a longer heterologous sequence, substitutions of one or more residues in the $HR1_C$ segment with proline, and introduction of one or more disulfide bonds. As described herein, these additional sequence modifications, alone or in any combination, can promote GP trimer formation, reduce metastability, and stabilize Ebolavirus GP in a native-like trimer conformation.

In some embodiments, the engineered Ebolavirus GP sequences of the invention contain a truncated or shortened soluble GP sequence (e.g., SEQ ID NO:2 or SEQ ID NO:3, or a conservatively modified or substantially identical variant thereof) with additional modifications in HR2. In the exemplified EBOV ectodomain GP sequence (SEQ ID NO:1), the HR2 motif encompasses residues 599-632. In some of these embodiments, the inward-facing residue in the 3-dimensional structure W615 is replaced with an amino acid residue that is smaller and more hydrophobic. In various embodiments, the W615 residue can be replaced with Leu, Phe, Ala, Val, or Ile so as to improve the HR2 stalk packing. These substitutions are intended to stabilize the Ebolavirus GP trimer. In some exemplified embodiments, the sequence substitution is W615L. In some other embodiments, the HR2 can contain a further substitution at residue 612 in additional to W615 substitution. In some of these embodiments, the amino acid substitutions are P612G/W615F. Some specific examples of engineered Ebolavirus GP sequences containing W615 substitution are shown in SEQ ID NOs:4 and 5.

In addition to the substitutions in HR2, the engineered soluble Ebolavirus GP sequences can alternatively or additionally contain an extension of the HR2 motif. In some these embodiments, extension of the HR2 motif (ending at residue 632) involves adding one or more adjacent residues in the MPER motif (starting at residue 633) that are naturally present in the Ebolavirus GP sequence. In various embodiments, the HR2 extension can be addition of its C-terminal adjacent residues in MPER up to residue 635, 636, 637, 638, 639, 640, 641, 642, 643, 644, 645, 646 or beyond. In some exemplified embodiments, the HR2 extension include extension to the TACE cleavage site (residue 637) in MPER, i.e., having MPER N-terminal residues KTLPD (SEQ ID NO:32). The TACE cleavage site is responsible for GP shedding from the virion surface after the host TACE cleavage. In some other embodiments, the HR2 extension can include 6 additional adjacent residues in the MPER motif, i.e., having MPER N-terminal residues KTLPDQGDNDN (SEQ ID NO:33). In some embodiments, extension of the HR2 motif involves substitution of some of the HR2 C-terminal residues with a longer heterologous sequence. In some of these embodiments, some of the HR2 C-terminal residues can be replaced with a longer GCN4 leucine zipper sequence. For example, HR2 can be extended by replacing residues 617-632 in HR2 with a 31 aa sequence (SEQ ID NO:34) from a GCN4 leucine zipper with PDB ID 2WPZ as exemplified herein. Some specific embodiments of engineered Ebolavirus GP proteins containing an HR2 extension are shown in SEQ ID NOs:5-7. Specific embodiments of engineered Ebolavirus GP proteins containing both an HR2 extension and a residue W615 substitution are shown in SEQ ID NOs:6 and 8.

Additionally or alternatively to the above-noted modifications in the HR2 region, the engineered Ebolavirus GP proteins of the invention can also contain mutations in the C segment of the HR1 region ($HR1_C$). Typically, the mutations in $HR1_C$ contain one or more proline substitutions that can stabilize the GP trimer and reduce metastability. In various embodiments, the proline substitution can be present at each position of $HR1_C$. As exemplified herein with EBOV GP sequence (SEQ ID NO:1), proline substitution can be introduced at each of residues 576-583 (TTELRTFS; SEQ ID NO:35). Thus, in various embodiments, engineered Ebolavirus GP proteins of the invention can contain one or more $HR1_C$ mutations among T576P, T577P, E578P, L579P, R580P, T581P, F582P, and S583P. In some exemplified embodiments, the engineered Ebolavirus GP proteins of the invention contain T577P ($P^2$) or L579P ($P^4$) mutations in $HR1_C$. Specific embodiments of engineered Ebolavirus GP sequences containing one or more proline substitutions in the $HR1_C$ segment are shown in SEQ ID NOs:9-16.

In some embodiments, the engineered Ebolavirus GP sequences of the invention contain both proline substitution in $HR1_C$ and modifications in HR2 noted above. For example, the engineered GP proteins can contain a proline substitution, and a W615 substitution and/or a further HR2 extension into MPER. The proline substitution can be at any residue in $HR1_C$ (e.g., at residue 577 or 579). W615 substitution can be any of W615L, W615F, W615A, W615V, or W615I. HR2 extension in these in these engineered GP proteins can be, e.g., extension to residue 637 (i.e., the TACE cleavage site) in MPER. Specific embodiments of engineered Ebolavirus GP sequences containing both a proline substitution in $HR1_C$ and also HR2 modifications are shown in SEQ ID NOs:17-22.

Other than the modifications in the heptad regions noted above, some engineered Ebolavirus GP sequences of the invention can alternatively or additionally contain one or more engineered cysteine residues for forming inter-GP disulfide bonds. By forming disulfide bonds between neighboring protomers of the GP trimer, these Cys substitutions and resulting engineered disulfide bonds can similarly function to promote trimer formation and to stabilize the GP in a native-like trimer conformation. Depending on the specific GP sequence to be used, one can readily determine the appropriate positions for introducing one or more inter-GP disulfide bonds. This can be performed, e.g., via analyzing potential amino acid pairs in the 3-dimension structure of the GP and subsequent biochemical and immunological characterizations as described herein. As exemplified with EBOV GP sequence (SEQ ID NO:1) herein, the engineered GP trimer protein can contain one or more engineered inter-protomer SS bonds among G91/A575 (SS2), F153/Y534 (SS1), T520/A575 (SS3), G157/I532 (SS4), D522/A575 (SS5) and K56/G599 (SS6). In some embodiments, the engineered GP trimer proteins of the invention contains engineered disulfide bond at G91/A575. Specific embodiments of engineered Ebolavirus GP proteins containing such engineered disulfide bonds are shown in SEQ ID NOs:23-28.

In some embodiments, the engineered Ebolavirus GP sequences of the invention can contain a C-terminal trimerization motif. This motif functions to further stabilize the trimer and also to increase the trimer ratio within the total protein yield. Suitable trimerization motifs for the invention include, e.g., T4 fibritin foldon (PDB ID: 4NCV) and viral capsid protein SHP (PDB: 1TD0). T4 fibritin (foldon) is well known in the art, and constitutes the C-terminal 30 amino acid residues of the trimeric protein fibritin from bacteriophage T4, and functions in promoting folding and trimerization of fibritin. See, e.g., Papanikolopoulou et al., J. Biol. Chem. 279: 8991-8998, 2004; and Guthe et al., J. Mol. Biol. 337: 905-915, 2004. Similarly, the SHP protein and its used as a functional trimerization motis are also well known in the art. See, e.g., Dreier et al., Proc Natl Acad Sci USA 110: E869-E877, 2013; and Hanzelmann et al., Structure 24: 140-147, 2016. In some exemplified embodiments, the trimerization motif in the engineered GP proteins comprise a foldon sequence shown in SEQ ID NO:29 or the 1TD0 protein sequence shown in SEQ ID NO:30. In some other embodiments, the employed trimerization motif can contain a sequence that is a conservatively modified variant or substantially identical (e.g., at least 90%, 95% or 99% identical) sequence of the exemplified sequence. In some embodiments, the trimerization motif can be inserted with a short GS linker. In various embodiments, the linker can contain 1-6 tandem repeats of GS. In some embodiments, an His6-tag can be added to the C-terminus of the trimerization motif to facilitate protein purification, e.g., by using a Nickel column.

In addition to the specific examples of GP polypeptides set forth in SEQ ID NOs:4-28, engineered Ebolavirus GP sequences of the invention also encompass sequences having an amino acid sequence that is substantially identical to one of these sequences, including conservatively modified variant sequences. In various embodiments, the engineered Ebolavirus GP proteins of the invention of the invention can have an amino acid sequence that is identical to any of SEQ ID NOs:4-28, except for one or more amino acid residue substitutions of non-conserved residues in HR1 and HR2 among different Ebolavirus species or strains, or substitutions in the non-conserved region or motif of the GP sequence of different Ebolavirus species or strains.

As exemplified herein with EBOV strain Mayinga-76 (SEQ ID NO:1), GP sequences from different Ebolavirus species and strains can all be readily employed to generate engineered Ebolavirus GP sequences in accordance with the strategy described herein. Ebolaviruses suitable for the invention include any of EBOV, SUDV, TAFV, BDBV and RESTV, as well as any strain of a given Ebolavirus species. In some embodiments of the invention, the engineering Ebolavirus GP proteins are chimeric. These chimeric Ebolavirus GP proteins or immunogen polypeptides can contain a chimeric GP sequence with different subunits or domains derived from multiple Ebolavirus species or from multiple strains of the same Ebolavirus species. For example, the GP1 and GP2 subunit sequences in the chimeric engineered Ebolavirus GP sequences can be derived from two different Ebolavirus species (e.g., GP2 from EBOV and GP1 from SUDV or TAFV) or from two different strains of the same Ebolavirus species (e.g., two different EBOV strains).

Many GP sequences of the five different Ebolavirus species and a great number of different strains of a given Ebolavirus species are known in the art. For example, such sequence information can be readily obtained from the Ebola Database maintained by the Los Alamos National Laboratory (LANL) and other Ebolavirus related databases such as the Virus Pathogen Resource (ViPR). See, e.g., Kuiken et al., Nucleic Acids Res. 40: D587-92, 2012; Pickett et al., Nucleic Acids Res. 40: D593-98, 2012; and Swetha et al., Adv Bioinformatics. 2016: 1673284. Admittedly, there is a considerable degree of variability among GP sequences of different Ebolavirus species and different strains of the same Ebolavirus species. However, as noted above, a certain number of conserved residues and motifs are present in HR1 and HR2 in all Ebolavirus species, which are the locations where mutations or modifications are introduced in the engineered GP proteins of the invention. In the engineering Ebolavirus GP proteins of the invention, one can readily determine the appropriate residues for modifications via sequence alignment and also considering conserved Ebolavirus GP motifs and residues known in the art. See, e.g., Leroy et al., J. General Virol. 83: 67-73, 2002; Arslan et al., Bioinformatics. 32: 151-154, 2017; Wec et al., Cell 169: 878-890, 2017; Jun et al., FEMS Microbiol Rev. 39: 764-778, 2015; Pappalardo et al., Sci. Rep. 6: 23743, 2016; and Ruedas et al., J. Virol. 91: e00392-17, 2017. Engineered Ebolavirus GP sequences based on any of the other Ebolavirus species and strains, or a combination of different strains or species, can all be generated using the same strategy exemplified herein for the EBOV GP sequence (SEQ ID NO:1).

As detailed below, the engineering Ebolavirus GP proteins may be conjugated to a presenting platform (e.g., nanoparticles or VLPs) via various means. Preferably, the conjugation is achieved via covalent linkage, e.g., protein fusions or insertions. In some preferred embodiments, the protein sequence is fused with the presenting platform sequence via a linker sequence. In various embodiments, other modifications can also be made to the engineering Ebolavirus GP proteins or the conjugating partner in order to improve stability or antigenicity.

The various engineered Ebolavirus GP molecules of the invention can be obtained or generated in accordance with the protocols exemplified herein or methods well known in the art. See, e.g., Sambrook et al., Molecular Cloning: A Laboratory Manual, Cold Spring Harbor Press, N.Y., ($3^{rd}$ ed. 2000); and Brent et al., Current Protocols in Molecular Biology, John Wiley & Sons, Inc. (ringbou ed., 2003). Upon recombinant expression (e.g., in HEK293 F cells as detailed herein), the proteins can be purified by any of the routinely practiced procedures. See, e.g., *Guide to Protein Purification*, Ed. Deutscher, Meth. Enzymol. 185, Academic Press, San Diego, 1990; and Scopes, *Protein Purification: Principles and Practice*, Springer Verlag, New York, 1982. Substantial purification denotes purification from other proteins or cellular components. A substantially purified protein is at least 60%, 70%, 80%, 90%, 95% or 98% pure. Once purified, antigenicity and other properties of the engineered Ebolavirus GP proteins can also be readily examined with standard methods, e.g., antigenic profiling using known bNAbs and non-NAbs, differential scanning calorimetry (DSC), electron microscopy, binding analysis via ELISA, Biolayer Interferometry (BLI), Surface Plasmon Resonance (SPR), and co-crystallography analysis as exemplified herein.

IV. Scaffolded Ebolavirus GP Vaccine Compositions

The invention provides Ebolavirus GP based vaccine compositions that contain a heterologous scaffold presenting or incorporating an engineered Ebolavirus GP protein described herein. Any heterologous scaffold can be used to present the engineered Ebolavirus GP protein in the construction of the vaccines of the invention. These include nanoparticles, virus-like particles, protein carriers (e.g., immunoglobulin chains or domains such as Fc, KLH, BSA, tetanus toxoid, and diphtheria toxoid), as well as various chemical scaffolds. In some embodiments, a virus-like particle (VLP) such as bacteriophage Qβ VLP and nanoparticles can be used. In some preferred embodiments, the heterologous scaffold for presenting or displaying the engineered Ebolavirus GP protein is a nanoparticle. Various nanoparticle platforms can be employed in generating the vaccine compositions of the invention. In general, the nanoparticles employed in the invention need to be formed by multiple copies of a single subunit. The nanoparticles are typically ball-like shaped, and/or have rotational symmetry (e.g., with 3-fold and 5-fold axes), e.g., with an icosahedral structure exemplified herein. Additionally or alternatively, the amino-terminus of the particle subunit has to be exposed and in close proximity to the 3-fold axis, and the spacing of three amino-termini has to closely match the spacing of the carboxyl-termini of the Ebolavirus GP protein. In some preferred embodiments, the immunogens comprise self-assembling naoparticles with a diameter of about 20 nm or less (usually assembled from 12, 24, or 60 sububits) and 3-fold axes on the particle surface.

In some preferred embodiments, the engineered Ebolavirus GP protein is presented on self-assembling nanoparticles such as self-assembling nanoparticles derived from E2p, I3-01v9 and ferritin (FR) as exemplified herein. E2p is a redesigned variant of dihydrolipoyl acyltransferase from *Bacillus stearothermophilus* that has been shown to self-assemble into thermostable 60-meric nanoparticle. See, e.g., He et al., *Nat. Commun.* 7:12041, 2016. Similarly, I3-01 is an engineered protein that can self-assemble into hyperstable nanoparticles. See, e.g., Hsia et al., Nature 535, 136-139, 2016. A modified version of I3-01, I3-01v9 is used here as exemplification. Ferritin is a globular protein found in all animals, bacteria, and plants. The globular form of ferritin is made up of monomeric subunit proteins (also referred to as monomeric ferritin subunits), which are polypeptides having a molecule weight of approximately 17-20 kDa. Amino acid sequences of E2p, I3-01v9 and ferritin nanoparticle subunits as exemplified herein are shown in SEQ ID NOs:36-38, respectively. Relative to the original sequence, E2p sequence shown in SEQ ID NO:36 contains an Ala substitution at residue 92 as underscored in the sequence below. Sequences of some other suitable nanoparticle sequences are also known in the art. See, e.g., WO2017/192434, WO2019/089817 and WO19/241483. In various embodiments, the Ebolavirus nanoparticle vaccines of the invention can employ any of these known nanoparticles, as well as their conservatively modified variants or variants with substantially identical (e.g., at least 90%, 95% or 99% identical) sequences.

E2p subunit sequence
(SEQ ID NO: 36)
AAAKPATTEGEFPETREKMSGIRRAIAKAMVHSKHTAPHVTLMDEADVT

KLVAHRKKFKAIAAEKGIKLTFLPYVVKALVSALREYPVLNTAIDDETE

EIIQKHYYNIGIAADTDRGLLVPVIKHADRKPIFALAQEINELAEKARD

GKLTPGEMKGASCTITNIGSAGGQWFTPVINHPEVAILGIGRIAEKPIV

RDGEIVAAPMLALSLSFDHRMIDGATAQKALNHIKRLLSDPELLLM

I3-01v9 subunit sequence
(SEQ ID NO: 37)
MKMEELFKKHKIVAVLRANSVEEAKMKALAVFVGGVHLIEITFTVPDAD

TVIKELSFLKELGAIIGAGTVTSVEQCRKAVESGAEFIVSPHLDEEISQ

FCKEKGVFYMPGVMTPTELVKAMKLGHTILKLFPGEVVGPQFVKAMKGP

FPNVKFVPTGGVNLDNVCEWFKAGVLAVGVGSALVKGTIAEVAAKAAAF

VEKIRGCTE

Ferritin sequence
(SEQ ID NO: 38)
DIIKLLNEQVNKEMNSSNLYMSMSSWCYTHSLDGAGLFLFDHAAEEYEH

AKKLIIFLNENNVPVQLTSISAPEHKFEGLTQIFQKAYEHEQHISESIN

NIVDHAIKSKDHATFNFLQWYVAEQHEEEVLFKDILDKIELIGNENHGL

YLADQYVKGIAKSRK

In addition to these exemplified nanoparticle sequences, many other nanoparticles or VLPs known in the art may also be used in the practice of the invention. These include, e.g., *Aquifex aeolicus* lumazine synthase, *Thermotoga Maritima* encapsulin, *Myxococcus xanthus* encapsulin, bacteriophage Qbeta virus particle, Flock House Virus (FHV) particle, ORSAY virus particle, and infectious bursal disease virus (IBDV) particle. Other molecules that may be used as the presenting platform of the nanoparticle vaccines of the invention include, e.g., molecules with the following PDB IDs: 1JIG (12-mer Dlp-2 from *Bacillus anthracis*), 1UVH (12-mer DPS from *Mycrobacteriurn smegmatis*), 2YGD (24-mer eye lens chaperone αB-crystallin), 3CS0 (24-mer DegP24), 3MH6 and 3MH7 (24-mer HtrA proteases), 3PV2 (12-mer HtrA homolog DegQ WT), 4A8C (12-mer DegQ from *E. Coli.*), 4A9G (24-mer DegQ from *E. Coli.*), 4EVE (12-mer HP-NAP from *Helicobacter pylori* strain YS29), and 4GQU (24-mer HisB from *Mycobacterium tuberculosis*).

In various embodiments, the Ebolavirus GP protein to be displayed on a nanoparticle platform may optionally contain a trimerization motif described above, e.g., foldon or SHP. Some Ebolavirus nanoparticle vaccine compositions can additionally contain other structural components that function to further enhance stability and antigenicity of the displayed immunogen. In some embodiments, a locking protein domain can be inserted into the nanoparticle construct, e.g., by covalently fused to the C-terminus of the nanoparticle subunit. The locking domain can be any dimeric protein that is capable of forming an interface through specific interactions such as hydrophobic (van der Waals) contacts, hydrogen bonds, and/or salt bridges. General guidance on selecting locking domains and specific examples are described in the art, e.g., PCT2019/036917. In some exemplified embodiments, the locking domain used in the Ebolavirus nanoparticle vaccines of the invention can contain locking domain LD4 or LD7 exemplified herein.

In some embodiments, Ebolavirus nanoparticle vaccines of the invention can also contain a T-cell epitope to promote robust T-cell responses and to steer B cell development towards bNAbs. The T-cell epitope can be located at any position in relation to the other structural components as long as it does not impact presentation of the immunogen polypeptides on the nanoparticle surface. Any T-cell epitope sequences or peptides known in the art may be employed in the practice of the present invention. They include any polypeptide sequence that contain MHC class-II epitopes and can effectively activate CD4+ and CD8+ T cells upon immunization, e.g., T-helper epitope that activates CD4+ T helper cells. See, e.g., Alexander et al., Immunity 1, 751-761,1994; Ahlers et al., J. Clin. Invest. 108:1677-1685, 2001; Fraser et al., Vaccine 32, 2896-2903, 2014; De Groot et al., Immunol. Cell Biol. 8:255-269, 2002; and Gene Ther. 21: 225-232, 2014. In some embodiments, the T cell epitope inserted into the Ebolavirus nanoparticle vaccine construct is a universal pan DR epitope peptide (PADRE). See, e.g., Hung et al., J. Mole. Ther. 15: 1211-19, 2007; Wu et al., J. Biomed. Sci. 17: 88, 2010; and Bissati et al., npj Vaccines 2: 24, 2017. Other examples of suitable T-cell epitope are also described in the art, e.g., the D and TpD epitope (Fraser et al., Vaccine 32, 2896-2903, 2014). In some embodiments, the employed PADRE peptide contains a sequence AKFVAAWTLKAAA (SEQ ID NO:31), a conservatively modified variant or substantially identical (e.g., at least 90%, 95% or 99% identical) sequence thereof. In some of these embodiments, the PADRE epitope is inserted at the C-terminus of a locking domain, e.g., LD4 or LD7 as exemplified herein. In some of these embodiments, a GS restriction site can be added between the LD and the PADRE epitope.

The scaffolded Ebolavirus vaccine compositions of the invention can be constructed in accordance with standard recombinant techniques and the methods described herein (see, e.g., the Examples herein) and/or other methods that have been described in the art, e.g., He et al., Nat. Comm. 7, 12041, 2016; Kong et al., Nat. Comm. 7, 12040, 2016; He et al., Sci Adv. 4(11):eaau6769, 2018; and PCT publications WO2017/192434, WO2019/089817 and WO19/241483. In various embodiments, nanoparticle displaying any of the engineered Ebolavirus GP proteins can be constructed by fusing the Ebolavirus GP polypeptide to the subunit of the nanoparticle (e.g., E2p subunit). Preferably, C-terminus of the Ebolavirus GP polypeptide is fused to the N-terminus of the nanoparticle subunit. In some embodiments, a short peptide spacer can be used to connect the Ebolavirus GP polypeptide and the nanoparticle. For example, the spacer can contain a GS restriction site and/or a longer $G_4S$ (SEQ ID NO:43) or $(G_4S)_2$ (SEQ ID NO:42) linker as exemplified herein. Some embodiments of the invention are directed to nanoparticles displaying engineered Ebolavirus GP protein GPΔmuc-WL$^2$P$^2$ protein (SEQ ID NO:17) with different combination of nanoparticle subunit sequence, locking domain sequence and/or T-cell epitope. Some specific examples of such nanoparticle vaccine compositions have a sequence structure of GPΔmuc-WL$^2$P$^2$-AS-G$_4$S-ferritin, GPΔmuc-WL$^2$P$^2$-AS-E2p-LD4-PADRE, or GPΔmuc-WL$^2$P$^2$-AS-(G$_4$S)$_2$-I3-01v9-LD7-PADRE.

Once constructed, the antigeniciy and structural integrity of the nanoparticle displayed Ebolavirus GP polypeptides can be readily analyzed via standard assays, e.g., antibody binding assays, biolayer interferometry, and negative-stain electron microscopy (EM). As exemplified herein, the various fusion molecules can all self-assemble into nanoparticles that display immunogenic epitopes of the Ebolavirus GP proteins. By eliciting a robust neutralizing antibody response, these nanoparticles are useful for vaccinating individuals against a broad range of Ebolavirus infections.

V. Polynucleotides and Expression Constructs

The engineered Ebolavirus GP proteins and the nanoparticle vaccine compositions of the invention are typically produced by first generating expression constructs (i.e., expression vectors) that contain operably linked coding sequences of the various structural components described herein. Accordingly, in some related aspects, the invention provides polynucleotides (DNA or RNA) that encode the engineered Ebolavirus GP proteins or polypeptides, and that encode the subunit of nanoparticles displayed the engineered Ebolavirus GP polypeptides as described herein, as well as expression vectors that harbor such polynucleotides and host cells for producing the Ebolavirus GP immunogen polypeptides and the vaccine compositions (e.g., HEK293 F cells and ExpiCHO cells exemplified herein). The fusion polypeptides encoded by the polynucleotides or expressed from the vectors are also included in the invention.

The polynucleotides and related vectors can be readily generated with standard molecular biology techniques or the protocols exemplified herein. For example, general protocols for cloning, transfecting, transient gene expression and obtaining stable transfected cell lines are described in the art, e.g., Sambrook et al., Molecular Cloning: A Laboratory Manual, Cold Spring Harbor Press, N.Y., (3$^{rd}$ ed., 2000); and Brent et al., Current Protocols in Molecular Biology, John Wiley & Sons, Inc. (ringbou edition, 2003). Introducing mutations to a polynucleotide sequence by PCR can be performed as described in, e.g., *PCR Technology: Principles and Applications for DNA Amplification*, H. A. Erlich (Ed.), Freeman Press, NY, N.Y., 1992; *PCR Protocols: A Guide to Methods and Applications*, Innis et al. (Ed.), Academic Press, San Diego, Calif., 1990; Manila et al., Nucleic Acids Res. 19:967, 1991; and Eckert et al., PCR Methods and Applications 1:17, 1991.

The selection of a particular vector depends upon the intended use of the fusion polypeptides. For example, the selected vector must be capable of driving expression of the fusion polypeptide in the desired cell type, whether that cell type be prokaryotic or eukaryotic. Many vectors contain sequences allowing both prokaryotic vector replication and eukaryotic expression of operably linked gene sequences. Vectors useful for the invention may be autonomously replicating, that is, the vector exists extrachromosomally and its replication is not necessarily directly linked to the replication of the host cell's genome. Alternatively, the replication of the vector may be linked to the replication of the host's chromosomal DNA, for example, the vector may be integrated into the chromosome of the host cell as achieved by retroviral vectors and in stably transfected cell lines. Both viral-based and nonviral expression vectors can be used to produce the immunogens in a mammalian host cell. Nonviral vectors and systems include plasmids, episomal vectors, typically with an expression cassette for expressing a protein or RNA, and human artificial chromosomes (see, e.g., Harrington et al., Nat. Genet. 15:345, 1997). Useful viral vectors include vectors based on lentiviruses or other retroviruses, adenoviruses, adeno-associated viruses, cytomegalovirus, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

Depending on the specific vector used for expressing the fusion polypeptide, various known cells or cell lines can be employed in the practice of the invention. The host cell can be any cell into which recombinant vectors carrying a fusion of the invention may be introduced and wherein the vectors are permitted to drive the expression of the fusion polypeptide is useful for the invention. It may be prokaryotic, such as any of a number of bacterial strains, or may be eukaryotic, such as yeast or other fungal cells, insect or amphibian cells, or mammalian cells including, for example, rodent, simian or human cells. Cells expressing the fusion polypeptides of the invention may be primary cultured cells or may be an established cell line. Thus, in addition to the cell lines exemplified herein (e.g., CHO cells), a number of other host cell lines capable well known in the art may also be used in the practice of the invention. These include, e.g., various Cos cell lines, HeLa cells, HEK293, AtT20, BV2, and N18 cells, myeloma cell lines, transformed B-cells and hybridomas.

The use of mammalian tissue cell culture to express polypeptides is discussed generally in, e.g., Winnacker, *From Genes to Clones*, VCH Publishers, N.Y., N.Y., 1987. The fusion polypeptide-expressing vectors may be introduced to the selected host cells by any of a number of suitable methods known to those skilled in the art. For the introduction of fusion polypeptide-encoding vectors to mammalian cells, the method used will depend upon the form of the vector. For plasmid vectors, DNA encoding the fusion polypeptide sequences may be introduced by any of a number of transfection methods, including, for example, lipid-mediated transfection ("lipofection"), DEAE-dextran-mediated transfection, electroporation or calcium phosphate precipitation. These methods are detailed, for example, in Brent et al., supra. Lipofection reagents and methods suitable for transient transfection of a wide variety of transformed and non-transformed or primary cells are widely available, making lipofection an attractive method of introducing constructs to eukaryotic, and particularly mammalian cells in culture. For example, LipofectAMINE™ (Life Technologies) or LipoTaxi™ (Stratagene) kits are available. Other companies offering reagents and methods for lipofection include Bio-Rad Laboratories, Clontech, Glen Research, Life Technologies, JBL Scientific, MBI Fermentas, PanVera, Promega, Quantum Biotechnologies, Sigma-Aldrich, and Wako Chemicals USA.

For long-term, high-yield production of recombinant fusion polypeptides, stable expression is preferred. Rather than using expression vectors which contain viral origins of replication, host cells can be transformed with the fusion polypeptide-encoding sequences controlled by appropriate expression control elements (e.g., promoter, enhancer, sequences, transcription terminators, polyadenylation sites, etc.), and selectable markers. The selectable marker in the recombinant vector confers resistance to the selection and allows cells to stably integrate the vector into their chromosomes. Commonly used selectable markers include neo, which confers resistance to the aminoglycoside G-418 (Colberre-Garapin, et al., J. Mol. Biol., 150:1, 1981); and hygro, which confers resistance to hygromycin (Santerre et al., Gene, 30: 147, 1984). Through appropriate selections, the transfected cells can contain integrated copies of the fusion polypeptide encoding sequence.

VI. Pharmaceutical Compositions and Therapeutic Applications

The invention provides pharmaceutical or immunogenic compositions and related methods of using the engineered Ebolavirus GP sequences and nanoparticles displaying the GP proteins as described herein for preventing and treating Ebolavirus infections. In some embodiments, an engineered Ebolavirus GP sequence (a polypeptide or a polynucleotide sequence) or a nanoparticle displaying an engineered protein is included in a pharmaceutical composition. The pharmaceutical composition can be either a therapeutic formulation or a prophylactic formulation. Typically, the composition additionally includes one or more pharmaceutically acceptable vehicles and, optionally, other therapeutic ingredients (for example, antibiotics or antiviral drugs). Various pharmaceutically acceptable additives can also be used in the compositions.

Some of the pharmaceutical compositions of the invention are vaccines. For vaccine compositions, appropriate adjuvants can be additionally included. Examples of suitable adjuvants include, e.g., aluminum hydroxide, lecithin, Freund's adjuvant, MPL™ and IL-12. In some embodiments, the engineered Ebolavirus GP sequences and related vaccines as disclosed herein can be formulated as a controlled-release or time-release formulation. This can be achieved in a composition that contains a slow release polymer or via a microencapsulated delivery system or bioadhesive gel. The various pharmaceutical compositions can be prepared in accordance with standard procedures well known in the art. See, e.g., Remington's Pharmaceutical Sciences, 19.sup.th Ed., Mack Publishing Company, Easton, Pa., 1995; Sustained and Controlled Release Drug Delivery Systems, J. R. Robinson, ed., Marcel Dekker, Inc., New York, 1978); U.S. Pat. Nos. 4,652,441 and 4,917,893; 4,677,191 and 4,728,721; and 4,675,189.

Therapeutic methods of the invention involve administering an engineered Ebolavirus GP sequence of the invention or a pharmaceutical composition containing the polypeptide to a subject having or at risk of developing an Ebolavirus infection (e.g., EBOV infection). In some embodiments, a pharmaceutical composition of the invention is employed in therapeutic or prophylactic applications for treating Ebolavirus infections or eliciting an protective immune response against an Ebolavirus species or strain in a subject. For example, the composition can be administered to a subject to induce an immune response to an Ebolavirus species, e.g., to induce production of broadly neutralizing antibodies to the Ebolavirus species. For subjects at risk of developing an Ebolavirus infection, a vaccine composition of the invention can be administered to provide prophylactic protection against viral infection. Depending on the specific subject and conditions, the pharmaceutical compositions of the invention can be administered to subjects by a variety of administration modes known to the person of ordinary skill in the art, for example, intramuscular, subcutaneous, intravenous, intra-arterial, intra-articular, intraperitoneal, or parenteral routes. In general, the pharmaceutical composition is administered to a subject in need of such treatment for a time and under conditions sufficient to prevent, inhibit, and/or ameliorate a selected disease or condition or one or more symptom(s) thereof. Symptoms of Ebolavirus exposure or infection include, e.g., inflammation of the liver, decreased appetite, fatigue, abdominal pain, jaundice, flu-like symptoms, itching, muscle pain, joint pain, intermittent low-grade fevers, sleep disturbances, nausea, dyspepsia, cognitive changes, depression headaches and mood changes.

Typically, the immunogenic composition of the invention is administered in an amount sufficient to induce an immune response against an Ebolavirus. For therapeutic applications, the compositions should contain a therapeutically effective amount of an engineered Ebolavirus GP sequence or nanoparticle vaccine composition described herein. For prophylactic applications, the compositions should contain a prophylactically effective amount of the engineered Ebolavirus GP sequence or a nanoparticle displaying a GP protein. The appropriate amount of the polypeptide immunogen or the nanoparticle composition can be determined based on the specific disease or condition to be treated or prevented, severity, age of the subject, and other personal attributes of the specific subject (e.g., the general state of the subject's health and the robustness of the subject's immune system). Determination of effective dosages is additionally guided with animal model studies followed up by human clinical trials and is guided by administration protocols that significantly reduce the occurrence or severity of targeted disease symptoms or conditions in the subject.

For prophylactic applications, the immunogenic composition is provided in advance of any symptom, for example in advance of infection. The prophylactic administration of the immunogenic compositions serves to prevent or ameliorate any subsequent infection. Thus, in some embodiments, a subject to be treated is one who has, or is at risk for developing, an Ebolavirus infection, for example because of exposure or the possibility of exposure to the Ebolavirus. Following administration of a therapeutically effective amount of the disclosed therapeutic compositions, the subject can be monitored for Ebolavirus infection, symptoms associated with Ebolavirus infection, or both.

For therapeutic applications, the immunogenic composition is provided at or after the onset of a symptom of disease or infection, for example after development of a symptom of an Ebolavirus infection, or after diagnosis of an Ebolavirus infection. The immunogenic composition can thus be provided prior to the anticipated exposure to Ebolaviruses in order to attenuate the anticipated severity, duration or extent of an infection and/or associated disease symptoms, after exposure or suspected exposure to the virus, or after the actual initiation of an infection.

The pharmaceutical composition of the invention can be combined with other agents known in the art for treating or preventing Ebolavirus infections. Administration of the pharmaceutical compositions and the known anti-viral agents can be either concurrently or sequentially.

Pharmaceutical compositions containing an engineered Ebolavirus GP protein or nanoparticle vaccine of the invention can be provided as components of a kit. Optionally, such a kit includes additional components including packaging, instructions and various other reagents, such as buffers, substrates, antibodies or ligands, such as control antibodies or ligands, and detection reagents. An optional instruction sheet can be additionally provided in the kits.

VII. Sequences of Some Engineered Ebolavirus GP Polypeptides or Structural Motifs

```
EBOV GP ectodomain sequence (GenBank AAG40168.1) (SEQ ID NO: 1):
MGVTGILQLP RDRFKRTSFFLWVIILFQRTFSI-PLGVIHN STLQVSDVDK

LVCRDKLSST NQLRSVGLNL EGNGVATDVP SATKRWGFRS GVPPKVVNYE

AGEWAENCYN LEIKKPDGSE CLPAAPDGIR GFPRCRYVHK VSGTGPCAGD

FAFHKEGAFF LYDRLASTVI YRGTTFAEGV VAFLILPQAK KDFFSSHPLR

EPVNATEDPS SGYYSTTIRY QATGFGTNET EYLFEVDNLT YVQLESRFTP

QFLLQLNETI YTSGKRSNTT GKLIWKVNPE IDTTIGEWAF WETKKNLTRK

IRSEELSFTV VSNGAKNISG QSPARTSSDP GTNTTTEDHK IMASENSSAM

VQVHSQGREA AVSHLTTLAT ISTSPQSLTT KPGPDNSTHN TPVYKLDISE

ATQVEQHHRR TDNDSTASDT PSATTAAGPP KAENTNTSKS TDFLDPATTT

SPQNHSETAG NNNTHHQDTG EESASSGKLG LITNTIAGVA GLITGGRRTR

REAIVNAQPK CNPNLHYWTT QDEGAAIGLA WIPYFGPAAE GIYIEGLMHN

QDGLICGLRQ LANETTQALQ LFLRATTELR TFSILNRKAI DFLLQRWGGT

CHILGPDCCI EPHDWTKNIT DKIDQIIHDFVD-KTLPDQGD NDNWWTGWRQ

WIPAGIGVTG VIIAVIALFC ICKFVF

Truncated EBOV GP_ECTO sequence (with leader/MLD/MPER deleted) (SEQ ID NO: 2):
PLGVIHNSTLQVSDVDKLVCRDKLSSTNQLRSVGLNLEGNGVATDVPSATKRW

GFRSGVPPKVVNYEAGEWAENCYNLEIKKPDGSECLPAAPDGIRGFPRCRYVH

KVSGTGPCAGDFAFHKEGAFFLYDRLASTVIYRGTTFAEGVVAFLILPQAKKDF

FSSHPLREPVNATEDPSSGYYSTTIRYQATGFGTNETEYLFEVDNLTYVQLESRF

TPQFLLQLNETIYTSGKRSNTTGKLIWKVNPEIDTTIGEWAFWETKKNLTRKIRS

EELSFTVVSTRHQDTGEESASSGKLGLITNTIAGVAGLITGGRRTRREAIVNAQP

KCNPNLHYWTTQDEGAAIGLAWIPYFGPAAEGIYIEGLMHNQDGLICGLRQLA

NETTQALQLFLRATTELRTFSILNRKAIDFLLQRWGGTCHILGPDCCIEPHDWTK

NITDKIDQIIHDFVD

Leaderless GPΔmuc (GP_ECTO with leader/MLD/MPER deleted + T42A)
                                                              (SEQ ID NO: 3)
PLGVIHNSALQVSDVDKLVCRDKLSSTNQLRSVGLNLEGNGVATDVPSATKR

WGFRSGVPPKVVNYEAGEWAENCYNLEIKKPDGSECLPAAPDGIRGFPRCRYV

HKVSGTGPCAGDFAFHKEGAFFLYDRLASTVIYRGTTFAEGVVAFLILPQAKK
```

-continued

DFFSSHPLREPVNATEDPSSGYYSTTIRYQATGFGTNETEYLFEVDNLTYVQLES

RFTPQFLLQLNETIYTSGKRSNTTGKLIWKVNPEIDTTIGEWAFWETKKNLTRKI

RSEELSFTVVSTHHQDTGEESASSGKLGLITNTIAGVAGLITGGRRTRREAIVNA

QPKCNPNLHYWTTQDEGAAIGLAWIPYFGPAAEGIYIEGLMHNQDGLICGLRQ

LANETTQALQLFLRATTELRTFSILNRKAIDFLLQRWGGTCHILGPDCCIEPHDW

TKNITDKIDQIIHDFVD

Leaderless GPΔmuc-W615L (SEQ ID NO: 4)

PLGVIHNSALQVSDVDKLVCRDKLSSTNQLRSVGLNLEGNGVATDVPSATKR

WGFRSGVPPKVVNYEAGEWAENCYNLEIKKPDGSECLPAAPDGIRGFPRCRYV

HKVSGTGPCAGDFAFHKEGAFFLYDRLASTVIYRGTTFAEGVVAFLILPQAKK

DFFSSHPLREPVNATEDPSSGYYSTTIRYQATGFGTNETEYLFEVDNLTYVQLES

RFTPQFLLQLNETIYTSGKRSNTTGKLIWKVNPEIDTTIGEWAFWETKKNLTRKI

RSEELSFTVVSTHHQDTGEESASSGKLGLITNTIAGVAGLITGGRRTRREAIVNA

QPKCNPNLHYWTTQDEGAAIGLAWIPYFGPAAEGIYIEGLMHNQDGLICGLRQ

LANETTQALQLFLRATTELRTFSILNRKAIDFLLQRWGGTCHILGPDCCIEPHDL

TKNITDKIDQIIHDFVD

Leaderless GPΔmuc-2WPZ (612/615 double mutation + 2WPZ extension)

(SEQ ID NO: 5)

PLGVIHNSALQVSDVDKLVCRDKLSSTNQLRSVGLNLEGNGVATDVPSATKR

WGFRSGVPPKVVNYEAGEWAENCYNLEIKKPDGSECLPAAPDGIRGFPRCRYV

HKVSGTGPCAGDFAFHKEGAFFLYDRLASTVIYRGTTFAEGVVAFLILPQAKK

DFFSSHPLREPVNATEDPSSGYYSTTIRYQATGFGTNETEYLFEVDNLTYVQLES

RFTPQFLLQLNETIYTSGKRSNTTGKLIWKVNPEIDTTIGEWAFWETKKNLTRKI

RSEELSFTVVSTHHQDTGEESASSGKLGLITNTIAGVAGLITGGRRTRREAIVNA

QPKCNPNLHYWTTQDEGAAIGLAWIPYFGPAAEGIYIEGLMHNQDGLICGLRQ

LANETTQALQLFLRATTELRTFSILNRKAIDFLLQRWGGTCHILGPDCCIEGHDF

TKQLEDKVEENLSKVYHNENEVARLKKLVGER

Leaderless GPΔmuc-L (C-terminal extension to residue 637)

(SEQ ID NO: 6)

PLGVIHNSALQVSDVDKLVCRDKLSSTNQLRSVGLNLEGNGVATDVPSATKR

WGFRSGVPPKVVNYEAGEWAENCYNLEIKKPDGSECLPAAPDGIRGFPRCRYV

HKVSGTGPCAGDFAFHKEGAFFLYDRLASTVIYRGTTFAEGVVAFLILPQAKK

DFFSSHPLREPVNATEDPSSGYYSTTIRYQATGFGTNETEYLFEVDNLTYVQLES

RFTPQFLLQLNETIYTSGKRSNTTGKLIWKVNPEIDTTIGEWAFWETKKNLTRKI

RSEELSFTVVSTHHQDTGEESASSGKLGLITNTIAGVAGLITGGRRTRREAIVNA

QPKCNPNLHYWTTQDEGAAIGLAWIPYFGPAAEGIYIEGLMHNQDGLICGLRQ

LANETTQALQLFLRATTELRTFSILNRKAIDFLLQRWGGTCHILGPDCCIEPHDW

TKNITDKIDQIIHDFVDKTLPD

Leaderless GPΔmuc-Ext (C-terminal extension to residue 643)

(SEQ ID NO: 7)

PLGVIHNSALQVSDVDKLVCRDKLSSTNQLRSVGLNLEGNGVATDVPSATKR

WGFRSGVPPKVVNYEAGEWAENCYNLEIKKPDGSECLPAAPDGIRGFPRCRYV

HKVSGTGPCAGDFAFHKEGAFFLYDRLASTVIYRGTTFAEGVVAFLILPQAKK

-continued

DFFSSHPLREPVNATEDPSSGYYSTTIRYQATGFGTNETEYLFEVDNLTYVQLES

RFTPQFLLQLNETIYTSGKRSNTTGKLIWKVNPEIDTTIGEWAFWETKKNLTRKI

RSEELSFTVVSTHHQDTGEESASSGKLGLITNTIAGVAGLITGGRRTRREAIVNA

QPKCNPNLHYWTTQDEGAAIGLAWIPYFGPAAEGIYIEGLMHNQDGLICGLRQ

LANETTQALQLFLRATTELRTFSILNRKAIDFLLQRWGGTCHILGPDCCIEPHDW

TKNITDKIDQIIHDFVDKTLPDQGDNDN

Leaderless GPΔmuc-W615L-L-foldon (or termed GPΔmuc-$WL^2$-foldon)

(SEQ ID NO: 8)

PLGVIHNSALQVSDVDKLVCRDKLSSTNQLRSVGLNLEGNGVATDVPSATKR

WGFRSGVPPKVVNYEAGEWAENCYNLEIKKPDGSECLPAAPDGIRGFPRCRYV

HKVSGTGPCAGDFAFHKEGAFFLYDRLASTVIYRGTTFAEGVVAFLILPQAKK

DFFSSHPLREPVNATEDPSSGYYSTTIRYQATGFGTNETEYLFEVDNLTYVQLES

RFTPQFLLQLNETIYTSGKRSNTTGKLIWKVNPEIDTTIGEWAFWETKKNLTRKI

RSEELSFTVVSTHHQDTGEESASSGKLGLITNTIAGVAGLITGGRRTRREAIVNA

QPKCNPNLHYWTTQDEGAAIGLAWIPYFGPAAEGIYIEGLMHNQDGLICGLRQ

LANETTQALQLFLRATTELRTFSILNRKAIDFLLQRWGGTCHILGPDCCIEPHDL

TKNITDKIDQIIHDFVDKTLPDASGYIPEAPRDGQAYVRKDGEWVLLSTFL

Leaderless GPΔmuc-W615L-P1 (T576P)

(SEQ ID NO: 9)

PLGVIHNSALQVSDVDKLVCRDKLSSTNQLRSVGLNLEGNGVATDVPSATKR

WGFRSGVPPKVVNYEAGEWAENCYNLEIKKPDGSECLPAAPDGIRGFPRCRYV

HKVSGTGPCAGDFAFHKEGAFFLYDRLASTVIYRGTTFAEGVVAFLILPQAKK

DFFSSHPLREPVNATEDPSSGYYSTTIRYQATGFGTNETEYLFEVDNLTYVQLES

RFTPQFLLQLNETIYTSGKRSNTTGKLIWKVNPEIDTTIGEWAFWETKKNLTRKI

RSEELSFTVVSTHHQDTGEESASSGKLGLITNTIAGVAGLITGGRRTRREAIVNA

QPKCNPNLHYWTTQDEGAAIGLAWIPYFGPAAEGIYIEGLMHNQDGLICGLRQ

LANETTQALQLFLRAPTELRTFSILNRKAIDFLLQRWGGTCHILGPDCCIEPHDL

TKNITDKIDQIIHDFVD

Leaderless GPΔmuc-W615L-P2 (T577P)

(SEQ ID NO: 10)

PLGVIHNSALQVSDVDKLVCRDKLSSTNQLRSVGLNLEGNGVATDVPSATKR

WGFRSGVPPKVVNYEAGEWAENCYNLEIKKPDGSECLPAAPDGIRGFPRCRYV

HKVSGTGPCAGDFAFHKEGAFFLYDRLASTVIYRGTTFAEGVVAFLILPQAKK

DFFSSHPLREPVNATEDPSSGYYSTTIRYQATGFGTNETEYLFEVDNLTYVQLES

RFTPQFLLQLNETIYTSGKRSNTTGKLIWKVNPEIDTTIGEWAFWETKKNLTRKI

RSEELSFTVVSTHHQDTGEESASSGKLGLITNTIAGVAGLITGGRRTRREAIVNA

QPKCNPNLHYWTTQDEGAAIGLAWIPYFGPAAEGIYIEGLMHNQDGLICGLRQ

LANETTQALQLFLRATPELRTFSILNRKAIDFLLQRWGGTCHILGPDCCIEPHDL

TKNITDKIDQIIHDFVD

Leaderless GPΔmuc-W615L-P3 (E578P)

(SEQ ID NO: 11)

PLGVIHNSALQVSDVDKLVCRDKLSSTNQLRSVGLNLEGNGVATDVPSATKR

WGFRSGVPPKVVNYEAGEWAENCYNLEIKKPDGSECLPAAPDGIRGFPRCRYV

HKVSGTGPCAGDFAFHKEGAFFLYDRLASTVIYRGTTFAEGVVAFLILPQAKK

DFFSSHPLREPVNATEDPSSGYYSTTIRYQATGFGTNETEYLFEVDNLTYVQLES

-continued

RFTPQFLLQLNETIYTSGKRSNTTGKLIWKVNPEIDTTIGEWAFWETKKNLTRKI

RSEELSFTVVSTHHQDTGEESASSGKLGLITNTIAGVAGLITGGRRTRREAIVNA

QPKCNPNLHYWTTQDEGAAIGLAWIPYFGPAAEGIYIEGLMHNQDGLICGLRQ

LANETTQALQLFLRATTPLRTFSILNRKAIDFLLQRWGGTCHILGPDCCIEPHDL

TKNITDKIDQIIHDFVD

Leaderless GPΔmuc-W615L-P4 (L579P)

(SEQ ID NO: 12)

PLGVIHNSALQVSDVDKLVCRDKLSSTNQLRSVGLNLEGNGVATDVPSATKR
WGFRSGVPPKVVNYEAGEWAENCYNLEIKKPDGSECLPAAPDGIRGFPRCRYV
HKVSGTGPCAGDFAFHKEGAFFLYDRLASTVIYRGTTFAEGVVAFLILPQAKK
DFFSSHPLREPVNATEDPSSGYYSTTIRYQATGFGTNETEYLFEVDNLTYVQLES
RFTPQFLLQLNETIYTSGKRSNTTGKLIWKVNPEIDTTIGEWAFWETKKNLTRKI
RSEELSFTVVSTHHQDTGEESASSGKLGLITNTIAGVAGLITGGRRTRREAIVNA
QPKCNPNLHYWTTQDEGAAIGLAWIPYFGPAAEGIYIEGLMHNQDGLICGLRQ
LANETTQALQLFLRATTEPRTFSILNRKAIDFLLQRWGGTCHILGPDCCIEPHDL
TKNITDKIDQIIHDFVD

Leaderless GPΔmuc-W615L-P5 (R580P)

(SEQ ID NO: 13)

PLGVIHNSALQVSDVDKLVCRDKLSSTNQLRSVGLNLEGNGVATDVPSATKR
WGFRSGVPPKVVNYEAGEWAENCYNLEIKKPDGSECLPAAPDGIRGFPRCRYV
HKVSGTGPCAGDFAFHKEGAFFLYDRLASTVIYRGTTFAEGVVAFLILPQAKK
DFFSSHPLREPVNATEDPSSGYYSTTIRYQATGFGTNETEYLFEVDNLTYVQLES
RFTPQFLLQLNETIYTSGKRSNTTGKLIWKVNPEIDTTIGEWAFWETKKNLTRKI
RSEELSFTVVSTHHQDTGEESASSGKLGLITNTIAGVAGLITGGRRTRREAIVNA
QPKCNPNLHYWTTQDEGAAIGLAWIPYFGPAAEGIYIEGLMHNQDGLICGLRQ
LANETTQALQLFLRATTELPTFSILNRKAIDFLLQRWGGTCHILGPDCCIEPHDL
TKNITDKIDQIIHDFVD

Leaderless GPΔmuc-W615L-P6 (T581P)

(SEQ ID NO: 14)

PLGVIHNSALQVSDVDKLVCRDKLSSTNQLRSVGLNLEGNGVATDVPSATKR
WGFRSGVPPKVVNYEAGEWAENCYNLEIKKPDGSECLPAAPDGIRGFPRCRYV
HKVSGTGPCAGDFAFHKEGAFFLYDRLASTVIYRGTTFAEGVVAFLILPQAKK
DFFSSHPLREPVNATEDPSSGYYSTTIRYQATGFGTNETEYLFEVDNLTYVQLES
RFTPQFLLQLNETIYTSGKRSNTTGKLIWKVNPEIDTTIGEWAFWETKKNLTRKI
RSEELSFTVVSTHHQDTGEESASSGKLGLITNTIAGVAGLITGGRRTRREAIVNA
QPKCNPNLHYWTTQDEGAAIGLAWIPYFGPAAEGIYIEGLMHNQDGLICGLRQ
LANETTQALQLFLRATTELRPFSILNRKAIDFLLQRWGGTCHILGPDCCIEPHDL
TKNITDKIDQIIHDFVD

Leaderless GPΔmuc-W615L-P7 (F582P)

(SEQ ID NO: 15)

PLGVIHNSALQVSDVDKLVCRDKLSSTNQLRSVGLNLEGNGVATDVPSATKR
WGFRSGVPPKVVNYEAGEWAENCYNLEIKKPDGSECLPAAPDGIRGFPRCRYV
HKVSGTGPCAGDFAFHKEGAFFLYDRLASTVIYRGTTFAEGVVAFLILPQAKK
DFFSSHPLREPVNATEDPSSGYYSTTIRYQATGFGTNETEYLFEVDNLTYVQLES

-continued

RFTPQFLLQLNETIYTSGKRSNTTGKLIWKVNPEIDTTIGEWAFWETKKNLTRKI

RSEELSFTVVSTHHQDTGEESASSGKLGLITNTIAGVAGLITGGRRTRREAIVNA

QPKCNPNLHYWTTQDEGAAIGLAWIPYFGPAAEGIYIEGLMHNQDGLICGLRQ

LANETTQALQLFLRATTELRTPSILNRKAIDFLLQRWGGTCHILGPDCCIEPHDL

TKNITDKIDQIIHDFVD

Leaderless GPΔmuc-W615L-P8 (S583P) (SEQ ID NO: 16)

PLGVIHNSALQVSDVDKLVCRDKLSSTNQLRSVGLNLEGNGVATDVPSATKR

WGFRSGVPPKVVNYEAGEWAENCYNLEIKKPDGSECLPAAPDGIRGFPRCRYV

HKVSGTGPCAGDFAFHKEGAFFLYDRLASTVIYRGTTFAEGVVAFLILPQAKK

DFFSSHPLREPVNATEDPSSGYYSTTIRYQATGFGTNETEYLFEVDNLTYVQLES

RFTPQFLLQLNETIYTSGKRSNTTGKLIWKVNPEIDTTIGEWAFWETKKNLTRKI

RSEELSFTVVSTHHQDTGEESASSGKLGLITNTIAGVAGLITGGRRTRREAIVNA

QPKCNPNLHYWTTQDEGAAIGLAWIPYFGPAAEGIYIEGLMHNQDGLICGLRQ

LANETTQALQLFLRATTELRTFPILNRKAIDFLLQRWGGTCHILGPDCCIEPHDL

TKNITDKIDQIIHDFVD

Leaderless GPΔmuc-W615L-L-P2

(SEQ ID NO: 17)

PLGVIHNSALQVSDVDKLVCRDKLSSTNQLRSVGLNLEGNGVATDVPSATKR

WGFRSGVPPKVVNYEAGEWAENCYNLEIKKPDGSECLPAAPDGIRGFPRCRYV

HKVSGTGPCAGDFAFHKEGAFFLYDRLASTVIYRGTTFAEGVVAFLILPQAKK

DFFSSHPLREPVNATEDPSSGYYSTTIRYQATGFGTNETEYLFEVDNLTYVQLES

RFTPQFLLQLNETIYTSGKRSNTTGKLIWKVNPEIDTTIGEWAFWETKKNLTRKI

RSEELSFTVVSTHHQDTGEESASSGKLGLITNTIAGVAGLITGGRRTRREAIVNA

QPKCNPNLHYWTTQDEGAAIGLAWIPYFGPAAEGIYIEGLMHNQDGLICGLRQ

LANETTQALQLFLRATPELRTFSILNRKAIDFLLQRWGGTCHILGPDCCIEPHDL

TKNITDKIDQIIHDFVDKTLPD

Leaderless GPΔmuc-W615L-L-P2 + restriction site "AS" and foldon (SEQ ID NO: 18)

PLGVIHNSALQVSDVDKLVCRDKLSSTNQLRSVGLNLEGNGVATDVPSATKR

WGFRSGVPPKVVNYEAGEWAENCYNLEIKKPDGSECLPAAPDGIRGFPRCRYV

HKVSGTGPCAGDFAFHKEGAFFLYDRLASTVIYRGTTFAEGVVAFLILPQAKK

DFFSSHPLREPVNATEDPSSGYYSTTIRYQATGFGTNETEYLFEVDNLTYVQLES

RFTPQFLLQLNETIYTSGKRSNTTGKLIWKVNPEIDTTIGEWAFWETKKNLTRKI

RSEELSFTVVSTHHQDTGEESASSGKLGLITNTIAGVAGLITGGRRTRREAIVNA

QPKCNPNLHYWTTQDEGAAIGLAWIPYFGPAAEGIYIEGLMHNQDGLICGLRQ

LANETTQALQLFLRATPELRTFSILNRKAIDFLLQRWGGTCHILGPDCCIEPHDL

TKNITDKIDQIIHDFVDKTLPDASGYIPEAPRDGQAYVRKDGEWVLLSTFL

Leaderless GPΔmuc-W615L-L-P2 + restriction site "AS" + $G_4S$ linker + 1TD0

(SEQ ID NO: 19)

PLGVIHNSALQVSDVDKLVCRDKLSSTNQLRSVGLNLEGNGVATDVPSATKR

WGFRSGVPPKVVNYEAGEWAENCYNLEIKKPDGSECLPAAPDGIRGFPRCRYV

HKVSGTGPCAGDFAFHKEGAFFLYDRLASTVIYRGTTFAEGVVAFLILPQAKK

DFFSSHPLREPVNATEDPSSGYYSTTIRYQATGFGTNETEYLFEVDNLTYVQLES

RFTPQFLLQLNETIYTSGKRSNTTGKLIWKVNPEIDTTIGEWAFWETKKNLTRKI

RSEELSFTVVSTHHQDTGEESASSGKLGLITNTIAGVAGLITGGRRTRREAIVNA

QPKCNPNLHYWTTQDEGAAIGLAWIPYFGPAAEGIYIEGLMHNQDGLICGLRQ

LANETTQALQLFLRATPELRTFSILNRKAIDFLLQRWGGTCHILGPDCCIEPHDL

TKNITDKIDQIIHDFVDKTLPDASGGGGSEVRIFAGNDPAHTATGSSGISSPTPAL

TPLMLDEATGKLVVWDGQKAGSAVGILVLPLEGTETALTYYKSGTFATEAIHW

PESVDEHKKANAFAGSALSHAA

Leaderless GPΔmuc-W615L-L-P4 (or termed GPΔmuc-WL$^2$P$^4$)
(SEQ ID NO: 20)
PLGVIHNSALQVSDVDKLVCRDKLSSTNQLRSVGLNLEGNGVATDVPSATKR

WGFRSGVPPKVVNYEAGEWAENCYNLEIKKPDGSECLPAAPDGIRGFPRCRYV

HKVSGTGPCAGDFAFHKEGAFFLYDRLASTVIYRGTTFAEGVVAFLILPQAKK

DFFSSHPLREPVNATEDPSSGYYSTTIRYQATGFGTNETEYLFEVDNLTYVQLES

RFTPQFLLQLNETIYTSGKRSNTTGKLIWKVNPEIDTTIGEWAFWETKKNLTRKI

RSEELSFTVVSTHHQDTGEESASSGKLGLITNTIAGVAGLITGGRRTRREAIVNA

QPKCNPNLHYWTTQDEGAAIGLAWIPYFGPAAEGIYIEGLMHNQDGLICGLRQ

LANETTQALQLFLRATTEPRTFSILNRKAIDFLLQRWGGTCHILGPDCCIEPHDL

TKNITDKIDQIIHDFVDKTLPD

Leaderless GPΔmuc-W615L-L-P4 + restriction site "AS" and foldon
(SEQ ID NO: 21)
PLGVIHNSALQVSDVDKLVCRDKLSSTNQLRSVGLNLEGNGVATDVPSATKR

WGFRSGVPPKVVNYEAGEWAENCYNLEIKKPDGSECLPAAPDGIRGFPRCRYV

HKVSGTGPCAGDFAFHKEGAFFLYDRLASTVIYRGTTFAEGVVAFLILPQAKK

DFFSSHPLREPVNATEDPSSGYYSTTIRYQATGFGTNETEYLFEVDNLTYVQLES

RFTPQFLLQLNETIYTSGKRSNTTGKLIWKVNPEIDTTIGEWAFWETKKNLTRKI

RSEELSFTVVSTHHQDTGEESASSGKLGLITNTIAGVAGLITGGRRTRREAIVNA

QPKCNPNLHYWTTQDEGAAIGLAWIPYFGPAAEGIYIEGLMHNQDGLICGLRQ

LANETTQALQLFLRATTEPRTFSILNRKAIDFLLQRWGGTCHILGPDCCIEPHDL

TKNITDKIDQIIHDFVDKTLPDASGYIPEAPRDGQAYVRKDGEWVLLSTFL

Leaderless GPΔmuc-W615L-L-P4 + restriction site "AS" + G$_4$S linker + 1TD0
(SEQ ID NO: 22)
PLGVIHNSALQVSDVDKLVCRDKLSSTNQLRSVGLNLEGNGVATDVPSATKR

WGFRSGVPPKVVNYEAGEWAENCYNLEIKKPDGSECLPAAPDGIRGFPRCRYV

HKVSGTGPCAGDFAFHKEGAFFLYDRLASTVIYRGTTFAEGVVAFLILPQAKK

DFFSSHPLREPVNATEDPSSGYYSTTIRYQATGFGTNETEYLFEVDNLTYVQLES

RFTPQFLLQLNETIYTSGKRSNTTGKLIWKVNPEIDTTIGEWAFWETKKNLTRKI

RSEELSFTVVSTHHQDTGEESASSGKLGLITNTIAGVAGLITGGRRTRREAIVNA

QPKCNPNLHYWTTQDEGAAIGLAWIPYFGPAAEGIYIEGLMHNQDGLICGLRQ

LANETTQALQLFLRATTEPRTFSILNRKAIDFLLQRWGGTCHILGPDCCIEPHDL

TKNITDKIDQIIHDFVDKTLPDASGGGGSEVRIFAGNDPAHTATGSSGISSPTPAL

TPLMLDEATGKLVVWDGQKAGSAVGILVLPLEGTETALTYYKSGTFATEAIHW

PESVDEHKKANAFAGSALSHAA

-continued

Leaderless GPΔmuc-SS1 (Y534C/F153C, rC_β-C_β = 3.819A)  (SEQ ID NO: 23)
PLGVIHNSALQVSDVDKLVCRDKLSSTNQLRSVGLNLEGNGVATDVPSATKR
WGFRSGVPPKVVNYEAGEWAENCYNLEIKKPDGSECLPAAPDGIRGFPRCRYV
HKVSGTGPCAGDFACHKEGAFFLYDRLASTVIYRGTTFAEGVVAFLILPQAKK
DFFSSHPLREPVNATEDPSSGYYSTTIRYQATGFGTNETEYLFEVDNLTYVQLES
RFTPQFLLQLNETIYTSGKRSNTTGKLIWKVNPEIDTTIGEWAFWETKKNLTRKI
RSEELSFTVVSTHHQDTGEESASSGKLGLITNTIAGVAGLITGGRRTRREAIVNA
QPKCNPNLHYWTTQDEGAAIGLAWIPCFGPAAEGIYIEGLMHNQDGLICGLRQ
LANETTQALQLFLRATTELRTFSILNRKAIDFLLQRWGGTCHILGPDCCIEPHDW
TKNITDKIDQIIHDFVD Leaderless GPΔmuc-SS2 (A538C/G91C, rC_β-C_α = 3.994A)  (SEQ ID NO: 24)
PLGVIHNSALQVSDVDKLVCRDKLSSTNQLRSVGLNLEGNGVATDVPSATKR
WGFRSCVPPKVVNYEAGEWAENCYNLEIKKPDGSECLPAAPDGIRGFPRCRYV
HKVSGTGPCAGDFAFHKEGAFFLYDRLASTVIYRGTTFAEGVVAFLILPQAKK
DFFSSHPLREPVNATEDPSSGYYSTTIRYQATGFGTNETEYLFEVDNLTYVQLES
RFTPQFLLQLNETIYTSGKRSNTTGKLIWKVNPEIDTTIGEWAFWETKKNLTRKI
RSEELSFTVVSTHHQDTGEESASSGKLGLITNTIAGVAGLITGGRRTRREAIVNA
QPKCNPNLHYWTTQDEGAAIGLAWIPYFGPCAEGIYIEGLMHNQDGLICGLRQ
LANETTQALQLFLRATTELRTFSILNRKAIDFLLQRWGGTCHILGPDCCIEPHDW
TKNITDKIDQIIHDFVD Leaderless GPΔmuc-SS3 (T520C/A575C, rC_β-C_β = 4.008A)  (SEQ ID NO: 25)
PLGVIHNSALQVSDVDKLVCRDKLSSTNQLRSVGLNLEGNGVATDVPSATKR
WGFRSGVPPKVVNYEAGEWAENCYNLEIKKPDGSECLPAAPDGIRGFPRCRYV
HKVSGTGPCAGDFAFHKEGAFFLYDRLASTVIYRGTTFAEGVVAFLILPQAKK
DFFSSHPLREPVNATEDPSSGYYSTTIRYQATGFGTNETEYLFEVDNLTYVQLES
RFTPQFLLQLNETIYTSGKRSNTTGKLIWKVNPEIDTTIGEWAFWETKKNLTRKI
RSEELSFTVVSTHHQDTGEESASSGKLGLITNTIAGVAGLITGGRRTRREAIVNA
QPKCNPNLHYVVTCQDEGAAIGLAWIPYFGPAAEGIYIEGLMHNQDGLICGLRQ
LANETTQALQLFLRCTTELRTFSILNRKAIDFLLQRWGGTCHILGPDCCIEPHDW
TKNITDKIDQIIHDFVD Leaderless GPΔmuc-554 (I532C/G157C, rC_β-C_α = 4.202A)  (SEQ ID NO: 26)
PLGVIHNSALQVSDVDKLVCRDKLSSTNQLRSVGLNLEGNGVATDVPSATKR
WGFRSGVPPKVVNYEAGEWAENCYNLEIKKPDGSECLPAAPDGIRGFPRCRYV
HKVSGTGPCAGDFAFHKECAFFLYDRLASTVIYRGTTFAEGVVAFLILPQAKKD
FFSSHPLREPVNATEDPSSGYYSTTIRYQATGFGTNETEYLFEVDNLTYVQLESR
FTPQFLLQLNETIYTSGKRSNTTGKLIWKVNPEIDTTIGEWAFWETKKNLTRKIR
SEELSFTVVSTHHQDTGEESASSGKLGLITNTIAGVAGLITGGRRTRREAIVNAQ
PKCNPNLHYWTTQDEGAAIGLAWCPYFGPAAEGIYIEGLMHNQDGLICGLRQL
ANETTQALQLFLRATTELRTFSILNRKAIDFLLQRWGGTCHILGPDCCIEPHDWT
KNITDKIDQIIHDFVD Leaderless GPΔmuc-SS5 (D522C/A575C, rC$_\beta$-C$_\beta$ = 4.410A) (SEQ ID NO: 27)

PLGVIHNSALQVSDVDKLVCRDKLSSTNQLRSVGLNLEGNGVATDVPSATKR
WGFRSGVPPKVVNYEAGEWAENCYNLEIKKPDGSECLPAAPDGIRGFPRCRYV
HKVSGTGPCAGDFAFHKEGAFFLYDRLASTVIYRGTTFAEGVVAFLILPQAKK
DFFSSHPLREPVNATEDPSSGYYSTTIRYQATGFGTNETEYLFEVDNLTYVQLES
RFTPQFLLQLNETIYTSGKRSNTTGKLIWKVNPEIDTTIGEWAFWETKKNLTRKI
RSEELSFTVVSTHHQDTGEESASSGKLGLITNTIAGVAGLITGGRRTRREAIVNA
QPKCNPNLHYWTTQCEGAAIGLAWIPYFGPAAEGIYIEGLMHNQDGLICGLRQ
LANETTQALQLFLRCTTELRTFSILNRKAIDFLLQRWGGTCHILGPDCCIEPHDW
TKNITDKIDQIIHDFVD

Leaderless GPΔmuc-SS6 (K56C/G599C, rC$_\beta$-C$_\alpha$ = 4.597A) (SEQ ID NO: 28)

PLGVIHNSALQVSDVDCLVCRDKLSSTNQLRSVGLNLEGNGVATDVPSATKRW
GFRSGVPPKVVNYEAGEWAENCYNLEIKKPDGSECLPAAPDGIRGFPRCRYVH
KVSGTGPCAGDFAFHKEGAFFLYDRLASTVIYRGTTFAEGVVAFLILPQAKKDF
FSSHPLREPVNATEDPSSGYYSTTIRYQATGFGTNETEYLFEVDNLTYVQLESRF
TPQFLLQLNETIYTSGKRSNTTGKLIWKVNPEIDTTIGEWAFWETKKNLTRKIRS
EELSFTVVSTRHQDTGEESASSGKLGLITNTIAGVAGLITGGRRTRREAIVNAQP
KCNPNLHYWTTQDEGAAIGLAWIPYFGPAAEGIYIEGLMHNQDGLICGLRQLA
NETTQALQLFLRATTELRTFSILNRKAIDFLLQRWGCTCHILGPDCCIEPHDWTK
NITDKIDQIIHDFVD

Foldon (SEQ ID NO: 29)
GYIPEAPRDGQAYVRKDGEWVLLSTFL:

1TD0 (SEQ ID NO: 30)
EVRIFAGNDPAHTATGSSGISSPTPALTPLMLDEATGKLVVWDGQKAGSAVGIL
VLPLEGTETALTYYKSGTFATEAIHWPESVDEHKKANAFAGSALSHAA:

GCN leucine zipper motif (SEQ ID NO: 34)
KQLEDKVEENLSKVYHNENEVARLKKLVGER

Locking domain LD4 (SEQ ID NO: 39):
FSEEQKKALDLAFYFDRRLTPEWRRYLSQRLGLNEEQIERWFRRKEQQIGWSH
PQFEK Locking domain LD7 (SEQ ID NO: 40):
SPAVDIGDRLDELEKALEALSAEDGHDDVGQRLESLLRRWNSRRAD Leader sequence of EBOV GP (SEQ ID NO: 41)
MGVTGILQLPRDRFKRTSFFLWVIILFQRTFSI

EXAMPLES

The following examples are offered to illustrate, but not to limit the present invention.

Example 1 Tag-Free Immunoaffinity Purification of EBOV GP Trimers

EBOV GP contains a heavily glycosylated mucin-like domain (MLD), which shields the glycan cap and neutralizing epitopes in GP1 and GP2. A soluble, mucin-deleted form of Zaire EBOV GP (GPΔmuc) that produced a high-resolution crystal structures (Zhao et al., Nature 535: 169-172, 2016) was used as a basic construct to investigate GP metastability. In HIV-1 vaccine research, immunoaffinity chromatography (IAC) columns based on bNAbs 2G12 and PGT145 (67, 68) have been widely used for the purification of native-like Env trimers. While 2G12 targets a glycan patch on a single gp120, PGT145 binds the trimer apex and can separate closed trimers from partially open and misfolded Envs. These two bNAb columns have also been used to purify HIV-1 gp140-presenting NPs. Such GP-specific antibody columns have not been reported In EBOV vaccine research. Recently, Corti et al. identified two potent NAbs, mAb114 and mAb100, from a human survivor (*Science* 351, 1339-1342, 2016). Misasi et al. elucidated the structural basis for neutralization by mAb114, which targets the receptor binding site (RBS), and mAb100, which interacts with the GP1/GP2 interface and internal fusion loop (IFL) of two GP subunits (*Science* 351, 1343-1346, 2016).

Here, we examined the utility of mAb114 and mAb100 as IAC columns. The GPΔmuc constructs with and without a C-terminal trimerization motif, foldon, were transiently expressed in 250 ml HEK293 F cells and purified on an antibody column prior to size-exclusion chromatography (SEC) using a Superdex 200 10/300 GL column and blue native polyacrylamide gel electrophoresis (BN-PAGE). With mAb114, both GPΔmuc samples showed aggregate (~9 ml), dimer (~12 ml), and monomer (~13.5-14 ml) peaks in the SEC profiles, but only GPΔmuc-foldon showed a visible trimer peak (~10.5-11 ml) in SEC and a faint band of slightly less than 440 kD on the BN gel. Following mAb100 purification, GPΔmuc showed overall low yield, whereas GPΔmuc-foldon demonstrated high trimer purity with no dimer and monomer peaks. Consistently, GPΔmuc-foldon registered a single trimer band on the BN gel. Taken together, while both mAb114 and mAb100 columns can be used for GP purification, mAb100 offers an effective IAC method for purifying native-like GP trimers due to its recognition of a quaternary GP epitope. The stark difference in trimer yield between the two soluble GPΔmuc constructs suggests a strong tendency for trimer dissociation.

Example 2 Effect of the HR2 Stalk on EBOV GP Metastability

EBOV GP possesses a long, extended HR2 stalk. Even in the high-resolution GPΔmuc structures, the HR2 stalk still contains less helical content than most coiled-coils in the database, ~15 aa vs ~30 aa, and becomes unwounded towards the C terminus, suggesting an inherent instability in HR2. Recently, King et al. solved a 3.17 Å-resolution structure for the MARV GPΔmuc trimer in complex with a therapeutic human mAb, MR191 (*Cell Host Microbe* 23, 101-109.e104, 2018). Surprisingly, the MARV HR2 stalk adopted a well-formed coiled-coil with canonical sidechain packing along the three-fold axis. To identify the cause of this difference, we obtained EBOV and MARV GP sequences from the Virus Pathogen Database and Analysis Resource (ViPR). A total of 274 EBOV GPs and 87 MARV GPs were used for sequence conservation analysis of the region spanning the $CX_6CC$ motif and the HR2 stalk, aa 601-632 for EBOV and aa 602-633 for MARV, respectively. Most inward-facing amino acids were conserved except for W615 in EBOV, or L616 in MARV. Indeed, structural analysis revealed a critical difference at this position: three $W615_S$ in EBOV GP (PDB: 5JQ3) formed a wide triangle at the neck of the coiled-coil with a Cα distance of 11.1 Å and a Cβ distance of 9.0 Å; in contrast, with a smaller and more hydrophobic L616, a Cα distance of 10.5 Å and a Cβ distance of 8.3 Å were observed in MARV GP (PDB: 6BP2).

Based on this finding, we hypothesized that a W615L mutation may stabilize the EBOV GP trimer. To further examine the effect of the stalk, we created three GPΔmuc constructs by replacing aa 617-632 with a GCN4 leucine zipper (PDB: 2WPZ, aa 3-33) and by extending the C terminus to 637 and 643 to include a newly identified bNAb epitope (King et al., Nat Commun 10, 1788, 2019) that spans HR2 and the membrane-proximal external region (MPER), termed "L" and "Ext", respectively (FIG. 3A). Double mutation P612G/W615F was introduced to the GPΔmuc-2WPZ construct between the $CX_6CC$ motif and the coiled-coil to reduce any structural strain in this region. These constructs were characterized by SEC and BN-PAGE following transient expression in 250-ml 293 F cells and mAb114 purification. Indeed, all three designs increased trimer yield with GPΔmuc-2WPZ showing the most visible trimer peak in SEC (FIG. 3B). Consistently, trimer bands were observed for all three constructs on the BN gel, albeit with less intensity for GPΔmuc-L and -Ext (FIG. 3C, left). Upon mAb100 purification, all three GPΔmuc variants showed more visible trimer bands than wildtype GPΔmuc (FIG. 3C, right), supporting the notion that the HR2 stalk is critical to GP trimer stability.

We next combined the W615L mutation and the "L" extension in a single construct named GPΔmuc-W615L-L-foldon, or simply GPΔmuc-$WL^2$-foldon. This construct, along with GPΔmuc-foldon, was expressed transiently in 1-liter 293 F cells and purified using an mAb100 column prior to SEC on a HiLoad Superdex 200 16/600 GL column. In three production runs, GPΔmuc-$WL^2$-foldon consistently outperformed the wildtype construct, showing a two-fold higher trimer peak in the SEC profile and an ~2.6-fold greater trimer yield after SEC (1.3 mg vs 0.5 mg). Thermostability was assessed by differential scanning calorimetry (DSC) for two purified GP trimers. The thermal denaturation midpoint (Tm) value of the stalk-stabilized trimer was 3° C. higher than that of the wildtype trimer (67° C. vs 64° C.). Consistently, stalk stabilization also increased the onset temperature (Ton) from 52.4° C. to 62.5° C., with a narrower half width of the peak ($\Delta T_{1/2}$) than the wildtype trimer (3.8° C. vs. 5.1° C.). Antigenicity was assessed for four mAb100/SEC-purified EBOV GP trimers in enzyme-linked immunosorbent assay (ELISA) (FIG. 3D-E). A panel of 10 antibodies was used, including three NAbs targeting the base (KZ52, c2G4 and c4G7), two human NAbs—mAb100 (IFL) and mAb114 (RBS), a non-NAb directed to the glycan cap (c13C6), and four pan-Ebolavirus bNAbs targeting the HR2-MPER epitope (BDBV223) and IFL (ADI-15878, ADI-15946, and CA45). The GPΔmuc trimer showed notably improved antibody binding with respect to the $GP_{ECTO}$ trimer with an up to 7.6-fold difference in half maximal effective concentration ($EC_{50}$), indicating that MLD can effectively shield GP from antibody recognition. The two HR2 stalk modifications led to further enhanced recognition of RBS by mAb114 and IFL by CA45, respectively, although the $EC_{50}$ values only showed moderate changes. A ~40% reduction in $EC_{50}$ was observed for GPΔmuc-$WL^2$-foldon binding to BDBV223. Taken together, two HR2 stalk mutations can effectively improve trimer yield, thermostability, and antigenicity for EBOV GP.

Example 3 Effect of the $HR1_C$ Bend on EBOV GP Metastability

We hypothesized that $HR1_C$ is essential to EBOV GP metastability. Since $HR1_C$ in wildtype EBOV GP is equivalent in length (8 aa) to a truncated HR1N in the prefusion-optimized HIV-1 Env, metastability in EBOV GP may not be sensitive to the $HR1_C$ length and likely requires a different solution. We thus hypothesized that a proline mutation in $HR1_C$, termed $P^{1-8}$, may rigidify the $HR1_C$ bend and improve the EBOV GP trimer stability.

To examine this possibility, eight GPΔmuc-W615L variants, each bearing a proline mutation in $HR1_C$ but without the L extension and foldon at the C terminus, were validated experimentally. All constructs were transiently expressed in 250-ml 293 F cells and purified using an mAb114 column, which captures all GP species. The proline mutation at most positions in HR1$_C$ showed little effect on the composition of GP species except for T577P (P$^2$) and L579P (P$^4$), which displayed notable trimer peaks at ~11 ml in the SEC profiles. In a separate experiment, all eight constructs were transiently expressed in 250-ml 293 F cells and purified using an mAb100 column. Only P$^2$ and P$^4$ showed any measurable trimer yield, with a notably high SEC peak observed for P$^4$ that corresponds to well-formed trimers. The mAb100-purified GP was also analyzed by BN-PAGE, which showed a trimer band for P$^2$ and P$^4$. Overall, the T577P mutation, P$^2$, can substantially increase trimer yield, while the L579P mutation, P$^4$, exhibited a less pronounced effect.

Next, the T577P mutation (P$^2$) was incorporated into the GPΔmuc-WL$^2$-foldon construct, resulting in a construct named GPΔmuc-WL$^2$P$^2$-foldon. This construct was expressed transiently in 1-liter 293 F cells and purified using an mAb100 column for SEC characterization on a HiLoad Superdex 200 16/600 GL column. In three production runs, GPΔmuc-WL$^2$P$^2$-foldon generated a trimer peak that was two- and four-fold higher than GPΔmuc-WL$^2$-foldon and wildtype GPΔmuc-foldon, respectively, with an average yield of 2.6 mg after SEC. Protein collected in the SEC range of 55.5-62.0 ml was analyzed by BN-PAGE, which displayed a trimer band across all fractions without any hint of impurity. The thermostability of GPΔmuc-WL$^2$P$^2$-foldon was determined by DSC after mAb100 and SEC purification.

Unexpectedly, two transition peaks were observed in the thermogram, one registered at a lower Tm of 61.6° C. and the other at a higher Tm of 68.2° C. To this end, a second construct bearing the L579P mutation (P$^4$), termed GPΔmuc-WL$^2$P$^4$-foldon, was also assessed by DSC. Although only one peak was observed in the thermogram with a Tm of 67.0° C., a slight widening at the onset of the peak suggested a similar unfolding behavior upon heating. DSC thus revealed the complexity associated with a proline-rigidified HR1$_C$ bend, which may increase the trimer yield at the cost of reducing GP thermostability. The antigenicity of GPΔmuc-WL$^2$P$^2$-foldon was assessed using the same panel of 10 antibodies by ELISA (FIG. 3F-G) and bio-layer interferometry (BLI). The T577P mutation (P$^2$) appeared to improve GP binding to most antibodies with respect to GPΔmuc-WL$^2$-foldon (FIG. 3G), with a 40% reduction in EC$_{50}$ observed for bNAb BDBV223, which targets HR2-MPER. Although BLI profiles were almost indistinguishable between wildtype and redesigned GPΔmuc-foldon trimers—all with fast on-rates and flattened dissociation curves, a two-fold higher signal at the lowest concentration (12.5 nM) was observed for GPΔmuc-WL$^2$P$^2$-foldon binding to bNAb BDBV223, consistent with the ELISA data.

Our results thus demonstrated the importance of HR1$_C$ to EBOV GP metastability and an unexpected sensitivity of HR1$_C$ to proline mutation. Recently, Rutten et al. tested proline mutations in HR1$_C$ along with a K588F mutation to stabilize filovirus GP trimers (*Cell Rep*. 30, 4540-50, 2020). While a similar pattern of increased trimer yield was observed for the T577P mutant, the reported thermostability data appeared to be inconsistent with our DSC measurement. Further investigation is warranted to fully understand the role of HR1$_C$ in filovirus-cell fusion and its impact on GP stability.

Example 4 GP Stabilization with Disulfide Bond Mutations

Since EBOV GP already contains an endogenous SS bond linking GP1 and GP2 (C53-C609), we examined whether inter-GP SS bonds can be used to promote trimer formation and to lock GP in a "closed" trimer. Based on a high-resolution EBOV GPΔmuc structure (PDB: 5JQ3), we identified inter-GP amino acid pairs whose C$_\alpha$-C$_\alpha$ distances are within a cutoff of 4.72 Å. A total of nine pairs were identified. After visual inspection, three were removed as they may interfere with an existing SS bond or a hydrophobic cluster. The remaining six were divided into three groups: the IFL-head group (SS1/2/4), the IFL-NHR group (SS/5), and the HR2 group (SS6). Six GPΔmuc-SS constructs were designed and then characterized by SEC following transient expression in 250-ml 293 F cells and mAb114 purification. Diverse SEC profiles were observed, with SS2 showing a substantial trimer peak, consistent with a band of slightly below 440 kD on the BN gel. The mAb100-purified materials were also analyzed by BN-PAGE, with trimer bands observed for SS2, SS3, and SS5. Antigenicity was assessed for the three SS mutants in ELISA using six antibodies. While all three SS mutants outperformed wildtype GPΔmuc, SS2 showed higher affinity for NAbs targeting the base and IFL. Taken together, a well-positioned inter-GP SS bond can effectively stabilize EBOV GP in a native-like trimer conformation.

Example 5 Crystallographic Analysis of Redesigned EBOV GPΔmuc Trimers

To understand how the stalk and HR1$_C$ mutations affect EBOV GP, we solved crystal structures for an unliganded GPΔmuc-foldon trimer with WL$^2$ and WL$^2$P$^2$ at 2.3 Å and 3.2 Å, respectively. Both proteins showed a three-lobed, chalice-like structure, with Cα root-mean-square deviations (r.m.s.d.) of 0.92-1.14 Å to a high-resolution structure (PDB: 5JQ3) at a single subunit level. WL$^2$P$^2$ yielded a more complete structure than WL$^2$ at the glycan cap (R302-V310) and the HR2 stalk (1627-D637). In the WL$^2$P$^2$ structure, the glycan cap covers the RBS with glycan moieties visible for N238/N257/N268 in GP1 and for N563 in GP2, while in the WL$^2$ structure for N238/N257 in GP1 and N563/N618 in GP2. GP1 consists mainly of β-strands which form a broad semi-circular groove that clamps the α3 helix and the β19-β20 strands in GP2. The T577P mutation appeared to have a minimum effect on the conformation of the HR1$_C$ bend, as indicated by a Cα r.m.s.d. of 0.19 Å for this 8-aa segment.

In the WL$^2$P$^2$ structure, the backbone carbonyl (CO) groups of R574, A575, and T576 in one subunit formed moderate-to-strong hydrogen bonds with the head group of R164 side chain in an adjacent subunit, whereas only one CO—NH distance was within the 3.5 Å cutoff in wildtype GPΔmuc. The W615L mutation exerted a visible structural effect on the HR2 stalk. We have speculated that a bulky, inward-facing W615 at the top of the coiled-coil destabilizes the HR2 stalk and a W615L mutation would improve its packing. Indeed, the Cα-Cα/Cβ-Cβ distances between two W615$_S$ of adjacent subunits in wildtype GPΔmuc, 11.1/9.0 Å, were reduced to 10.1/8.0 Å and 10.6/8.2 Å in WL$^2$ and WL$^2$P$^2$, respectively. As a result, the coiled-coil region in EBOV HR2 stalk added one more helical turn, thus resembling MARV HR2 stalk. The "L" extension in the WL$^2$P$^2$ structure could be fully modeled to D637 as a well-ordered loop anchored to the C-terminal foldon motif, rendering a complete HR2 stalk and partial MPER. Superposition of HR2 stalks yielded Cα r.m.s.d. values of 1.46 Å, 2.05 Å, and 1.85 Å with respect to EBOV-Mayinga (PDB: 5JQ3), SUDV (PDB: 3S88), and BDBV (PDB: 6EA5) GPs, respectively, suggesting some degree of structural variability in this region.

The WL$^2$P$^2$ structure was then compared to a recently reported Makona GPΔmuc structure (PDB: 6VKM) containing the T577P/K588F mutation. In total, 353 of 398 residues in the WL$^2$P$^2$ structure matched with the double mutant with a Cα r.m.s.d. of 0.89 Å. A more complete cathepsin cleavage loop was modeled in WL$^2$P$^2$ than previous structures (aa 197-210 vs. aa 193-213), suggesting that this loop bridges over the IFL and interacts with IFL-directed NAbs such as mAb100 (42). In addition, we observed more electron densities for the β18 loop in the glycan cap (aa 294-310) and the HR2 stalk than the double mutant. For the HR1$_C$ bend, WL$^2$P$^2$ showed more favorable hydrogen bonding patterns with a Ca r.m.s.d of 0.26 Å. A Ca r.m.s.d of 1.7 Å was obtained for the IFL region between the two structures. Lastly, the WL$^2$P$^2$ structure was docked into a panel of known GP/antibody complexes. Overall, WL$^2$P$^2$ has preserved all critical GP-antibody contacts. The mAb100/GP complex is of most interest as mAb100 has been used for GP purification with substantial purity. Cryo-EM has revealed additional electron density near the mAn100 light chain that likely corresponds to portions of the β13-β14 loop (aa 190-210) (Misari et al., Science 351: 1343-46, 2016). However, this density was not observed in a 6.7 Å-resolution crystal structure of the same complex (PDB: 5FHC). In the WL$^2$P$^2$ structure, density could be seen for up to H197, which would be in the proximity of mAb100 light chain in the docked WL$^2$P$^2$/mAb100 model. Collectively, our structures validated the rationally designed mutations and provide atomic details for regions that are unavailable in previous structures. The WL$^2$P$^2$ structure also provides a potential explanation for the increased trimer yield, although the cause of the two-peak thermogram remains unclear.

Example 6 Display of EBOV GPΔmuc Trimers on Multilayered Hyperstable Nanoparticles Self-assembling NPs provide an alternative to recombinant VLPs for vaccine development. We tested several protein NPs as "multivalent carriers" to display the redesigned GPΔmuc trimers for in vivo assessment. Specifically, we modeled the GPΔmuc trimer structure on ferritin (FR), E2p, and I3-01, resulting in GP-presenting NPs of 34.5 nm, 45.9 nm, and 49.2 nm, respectively. Superposition of the GPΔmuc C termini onto the FR and E2p N termini yielded Cα r.m.s.d. values of 7.0 Å and 5.5 Å, suggesting that GPΔmuc can be fused to FR with a short G$_4$S linker and to E2p without linker, respectively. However, the large spacing between the N termini of I3-01 subunits (~50.5 Å) requires a long linker to connect with the C termini of a GPΔmuc trimer, which form a long, narrow stalk. Based on computational modeling, a 10-aa (G$_4$S)$_2$ linker would suffice and result in a Cα r.m.s.d. of 0.8 Å. Here, we first displayed two GPΔmuc trimers, wildtype and WL$^2$P$^2$, on FR, E2p, and I3-01 with a 5-aa linker, no linker, and a 10-aa linker, respectively. All six GP-NP constructs were transiently expressed in 100-ml ExpiCHO cells followed by mAb100 purification and SEC on a Superose 6 10/300 GL column. Overall, WL$^2$P$^2$ outperformed wildtype GPΔmuc with greater NP yield and purity. Based on molecular weight (m.w.), the SEC peaks centered at 15 ml could be unassembled GP-NP species, suggesting an inherent instability for wildtype E2p and I3-01. The mAb100-purified GPΔmuc-WL$^2$P$^2$-presenting NP samples were further analyzed by negative stain EM, showing NPs mixed with impurity.

Previously, we demonstrated the use of a pan-reactive T-cell epitope as both a linker and as a built-in T-cell help in an HIV-1 NP construct based on I3-01 (55), suggesting that additional structural and functional components can be incorporated into such large 60-mers. Here, we sought to stabilize the E2p and I3-01 NPs via engineering. To this end, we fused a dimeric locking domain (LD) to the C terminus of an NP subunit, and then a T-cell epitope to the C terminus of a LD. We hypothesized that LD can stabilize the non-covalent NP-forming interface and the T-cell epitopes can form a cluster at the NP core to elicit a strong T-cell response upon vaccination. To test this hypothesis, we selected nine LDs from 815 homodimers in the protein database (PDB) (FIG. 4A). Based on structural modeling, LDs 1-7 were tested for E2p and five LDs (4-5 and 7-9) were tested for to I3-01, all displaying GPΔmuc-WL$^2$P$^2$. Following transient expression in 100-ml ExpiCHO cells and mAb100 purification, 12 LD-S containing NP samples were characterized by SEC. Notably, LD4 and LD7 increased the NP peak (UV$_{280}$ value) by 5- and 2.5-fold for E2p and I3-01, respectively, with substantially improved NP purity. Further incorporation of a T-cell epitope, PADRE, didn't alter or slightly improved the NP yield and purity.

A total of seven GP-NP samples, with three variants for each 60-mer, were further analyzed by BN-PAGE. FR and two E2p variants displayed a single high-m.w. band corresponding to well-formed NPs, whereas wildtype E2p and all three I3-01 samples showed additional low-m.w. bands at 232-440 kD on the gel, indicative of unassembled GP-NP species. The mAb100/SEC-purified GPΔmuc-WL$^2$P$^2$-presenting FR, E2p-LD4-PADRE (E2p-L4P), and I3-01-LD7-PADRE (I3-01-L7P) samples were analyzed by negative stain EM. In addition to high-purity NPs for all three samples, an array of well-formed GPΔmuc spikes could be readily seen on the surface of FR and E2p-L4P NPs, consistent with SEC and BN-PAGE. Antigenicity was assessed for these three purified NP samples by ELISA against the same antibody panel (FIG. 4B-C). Compared to the individual WL$^2$P$^2$ trimer, three NPs exhibited an epitope-specific binding pattern. Overall, NP display appeared to improve antibody binding to the RBS and glycan cap in GP1 and reduce antibody binding for bNAbs targeting the base and IFL at the GP1/GP2 interface and the GP2 stalk. This finding raised concerns that these conserved bNAb epitopes at the GP base and IFL on the NP-displayed trimers may not be as accessible as on the soluble trimers. To this end, BLI was performed to further probe antibody recognition of various GP epitopes (FIG. 4D-G). Using comparable molar concentrations for GP, three NPs showed considerably higher binding signals than the soluble trimer, suggesting that GP-presenting NPs may be more effective in promoting BCR clustering due to the avidity effect. Nonetheless, three NPs based on FR, E2p-L4P, and I3-01v9-L7P (FIG. 4H), in which I3-01v9 is a previously reported I3-01 variant, were selected for in vivo evaluation and comparison with trimers in mice and rabbits.

Example 7 Immunogenicity of EBOV GP Trimers and NPs in BALB/c Mice

We immunized BALB/c mice four times with three-week intervals to obtain an initial readout of immunogenicity for three EBOV GP/GPΔmuc trimers and three NPs. A soluble GP$_{ECTO}$ trimer, GP-foldon, was included to represent the wildtype GP (with MLD) used by EBOV vaccines in clinical testing. For the I3-01v9-L7P group, mice were immunized with 20 μg mAb100-purified instead of 50 μg mAb100/SEC-purified protein due to the low yield of this NP. We first assessed the GP-specific antibody response in mouse sera using GPΔmuc-WL²P²-1TD0 as a probe, in which 1TD0 (PDB: 1TD0) is a trimerization motif (FIG. 5A-C). Both GPΔmuc groups significantly outperformed the $GP_{ECTO}$ group throughout the immunization with P values<0.0064, suggesting that MLD can shield GP from antibody recognition. In contrast, little difference was found between the two GPΔmuc groups, with WL²P² showing a slightly higher average $EC_{50}$ titer at w2 and w5 that was reversed at later time points. Compared to the GPΔmuc-WL²P² trimer group, all NP groups showed lower $EC_{50}$ titers except for the E2p-L4P NP group at w2, which yielded a P value of 0.0381.

This finding was somewhat unexpected, as significant differences were found between E2 core and NP groups at both w2 and w5 in a recent HCV vaccine study (He et al., Sci. Adv. 6: eaaz6225, 2020), suggesting that antibody titers induced by antigen-presenting NPs may be greatly influenced by antigen size, structure, and epitope distribution. NP display may occlude antibody access to the base and stalk epitopes, which are the targets of many bNAbs. This result may also be attributed to other factors such as dosage. As the NP carrier accounts for 21-33% of the total mass of an NP vaccine and the same dose (50 μg protein) has been used for all vaccine groups except for the I3-01v9-L7P NP group, mice in the NP groups would receive significantly less GP antigen than mice in the trimer group.

We then validated the Ebolavirus pseudoparticle (Ebolavirus-pp) neutralization assay using a panel of 10 antibodies against EBOV-Makona and a BDBV strain in 293 T cells. As expected, early EBOV NAbs KZ52, c2G4, and c4G7 neutralized EBOV but not BDBV. NAbs mAb100 and mAb114 neutralized both Ebolavirus species with different potencies. Four bNAbs, three directed to IFL and one targeting HR2-MPER, cross-neutralized EBOV and BDBV. A non-NAb, c13C6, which binds the glycan cap and is part of a therapeutic antibody cocktail, appeared to enhance viral infection, suggesting a potential ADE effect. The Ebolavirus-pp assay was also performed in TZM-bl cells (FIG. 5D), which were used to screen small-molecule inhibitors. While all the tested NAbs/bNAbs blocked pseudovirus infection, c13C6 exhibited a similar pattern of ADE. When tested against pseudoparticles bearing the murine leukemia virus (MLV) Env, MLV-pps, c13C6 showed enhancement of infection while NAbs and bNAbs remained non-reactive (FIG. 5E).

We next assessed the immunized mouse samples against EBOV and BDBV in the Ebolavirus-pp assay. Immunoglobulin G (IgG) was purified from the mouse serum at the last time point (w11) to eliminate non-specific, anti-viral activities. Distinct patterns of antibody response were observed, suggesting the elicitation of NAbs and c13C6-like ADE-causing non-NAbs. Among the three trimer groups, while $GP_{ECTO}$ showed a moderate NAb response with ADE observed for 2-4 mice, a substantial increase in both NAb and c13C6-like responses was observed for GPΔmuc, suggesting that the removal of MLD can equally expose NAb epitopes and the glycan cap, a main target for ADE-causing antibodies in natural infection. The WL²P² mutation appeared to have largely reversed the adversary effect caused by the removal of MLD. Among the three NP groups, E2p-L4P was the best performer and showed primarily NAb response with little hint of ADE. However, a c13C6-like antibody response was observed for 2-3 mice in the FR group and for all mice in the I3-01v9-L7P group. Since c13C6 but not any of the NAbs/bNAbs reacted with MLV-pps (FIG. 5E), we sought to use the MLV-pp assay to "gauge" c13C6-like antibody responses induced by different vaccines (FIG. 5F). Indeed, we observed enhanced MLV-pp infection in excellent agreement with the ADE effect observed in the Ebolavirus-pp assay. The MLV-pp assay also indicated that the E2p-L4P NP induced a minimum c13C6-like response comparable to $GP_{ECTO}$ with the MLD shielding. The high level of ADE effect observed for the GPΔmuc and I3-01v9-L7P groups appeared to be associated with the presence of open trimers and unassembled GP-NP species, respectively.

The mouse data offered critical insights into the effect of various GP forms and NP carriers on vaccine-induced antibody response. In brief, a multilayered E2p NP with 20 closed GPΔmuc trimers on the surface provides a promising vaccine candidate. The benefit of NP display may not be fully reflected by binding antibody titers and should be judged by the type of antibodies elicited. The c13C6-like antibodies that target the glycan cap and cross-react with small secreted GP (ssGP) may cause adverse effects in vaccination.

Example 8 Immunogenicity of EBOV GP Trimers and NPs in Rabbits

Figure 6:
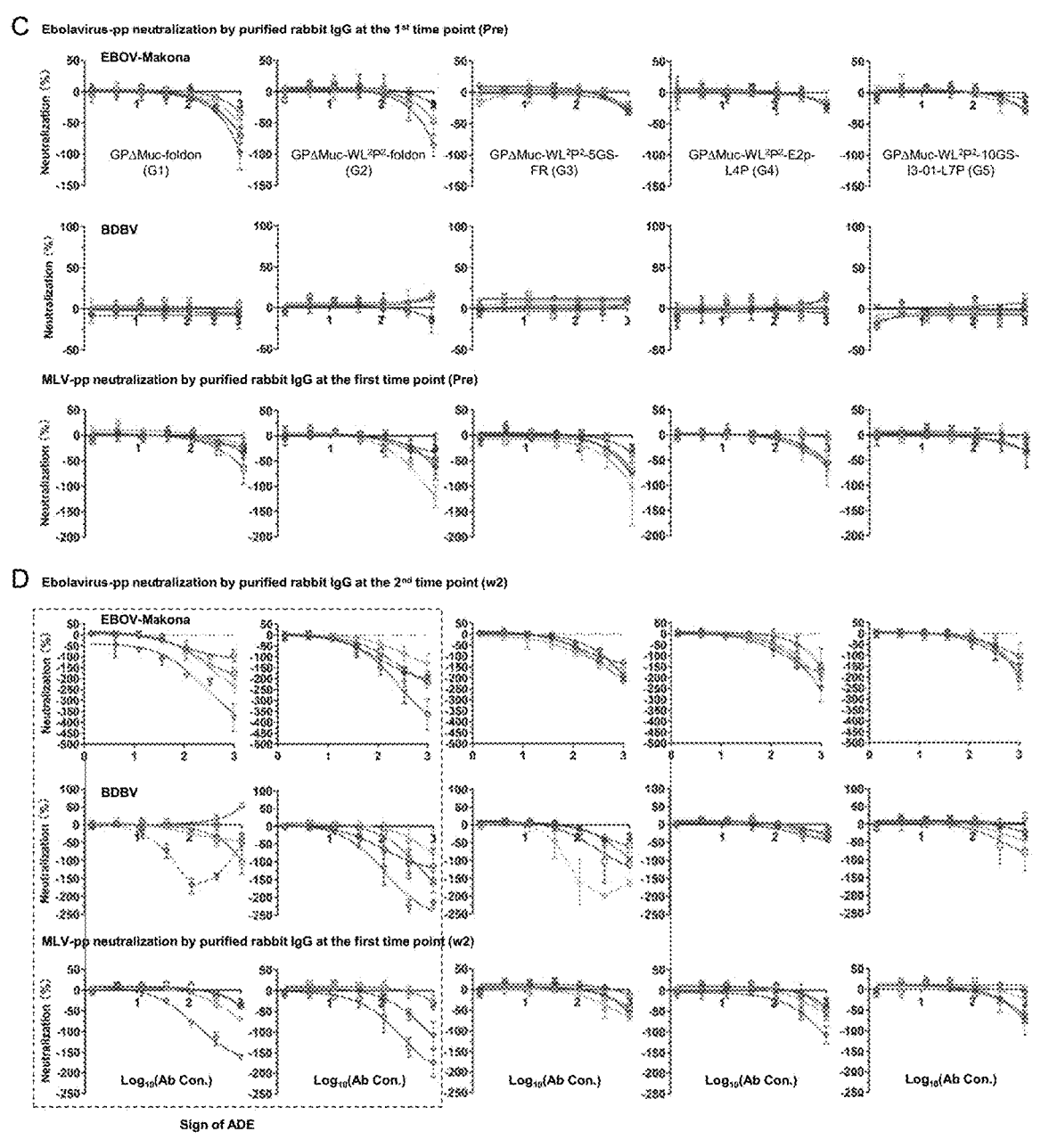

Two GPΔmuc trimers, wildtype and WL²P², and three NPs presenting the WL²P² trimer were also assessed in rabbits with four injections over three-week intervals. Rabbit sera collected at six timepoints during immunization were analyzed by ELISA using the same trimer probe (FIG. 6A-B). Of note, rabbits were immunized with 20 μg of mAb100/SEC-purified I3-01v9-L7P NP to reduce the c13C6-like responses. Between the GPΔmuc groups, the WL²P² group showed higher $EC_{50}$ titers for all six time points except for w11, with a significant P value of 0.0229 obtained for w5 (two weeks after the second injection). Among the three NP groups, a consistent pattern was observed, with the I3-01v9 group showing the highest $EC_{50}$ tier and the FR group the lowest throughout the immunization. A significant difference was found between the I3-01v9-L7P group and the E2p-L4P group for w8, w11, and w13 (four weeks after the last injection), with a P value of 0.0021-0.0053.

Compared to the GPΔmuc-WL²P² trimer group, the I3-01v9-L7P NP group showed higher $EC_{50}$ tiers for all six time points, with significant P values obtained for w8, w11, and w13. In contrast, the FR and E2p-L4P groups yielded lower $EC_{50}$ titers than their respective trimer group at w2 and w5, but this pattern was reversed at w8 and w11 with significant P values (0.0421 and 0.0492 for FR and E2p, respectively) at w8. However, the advantage of these two NP groups diminished at w11, showing lower $EC_{50}$ tiers than the trimer group at the last time point, w13. Purified IgGs from time points Pre, w2, w5, w8, and w11 were analyzed in Ebolavirus-pp and MLV-pp assays (FIG. 6C-F). At the last time point, all vaccine groups showed NAb responses to both Ebolavirus species with no sign of ADE, suggesting a different pattern compared to the mixed NAb/c13C6-like responses in mice. Of note, the I3-01v9-L7P NP group yielded higher average $IC_{50}$ (50% inhibitory concentration) titers, at 211.3 μg/ml and 11.72 μg/ml for EBOV and BDBV, respectively, than other groups, confirming that the unassembled GP-NP species—not the NP itself—were the cause of ADE in mouse immunization.

Consistently, all vaccine groups at w11 showed no enhancement of MLV-pp infection, in contrast to the mouse data (FIG. 5F). Therefore, c13C6-like antibodies appeared to be absent in serum toward the end of rabbit immunization. However, rabbit IgGs obtained from the earlier time points demonstrated an increasing NAb response accompanied by a declining c13C6-like antibody response (FIG. 6C-F). In Ebolavirus-pp neutralization assays against EBOV-Makona, ADE was first observed for the two trimer groups, the FR group, and the two multilayered NP groups at w2, w5, and w8, but then disappeared at w5, w8, and w11, respectively. Our analysis thus revealed a unique pattern for vaccine-induced c13C6-like antibodies in rabbits, which might change epitope specificity through the mechanism of "gene conversion" upon repeated antigen stimulation.

Example 9 B Cell Response Profiles Associated with EBOV GP Trimers and NPs

Figure 7:
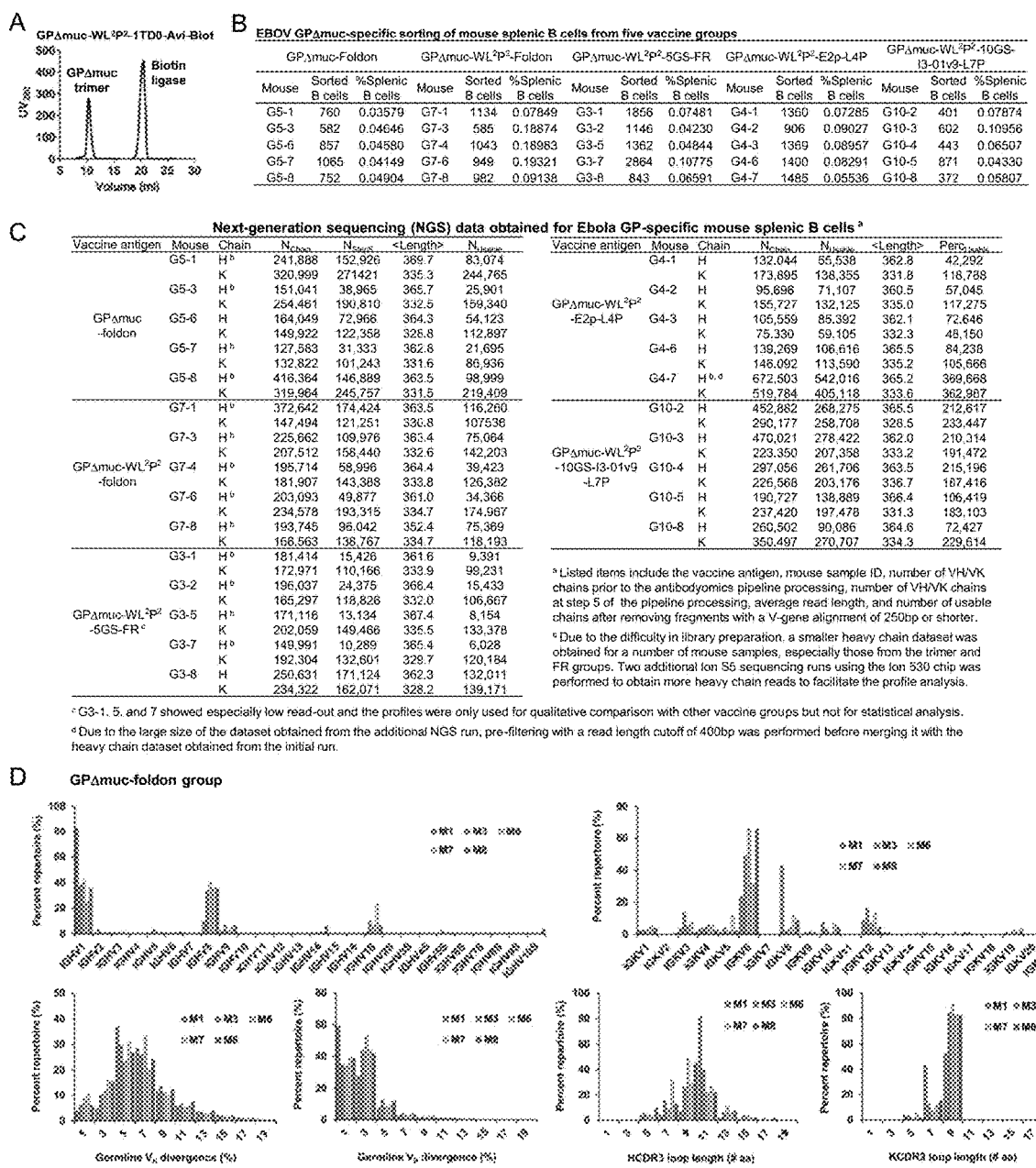
FIG. 7 shows unbiased NGS repertoire analysis of bulk-sorted Ebola GP-specific mouse splenic B cells. (A) SEC profile of a biotinylated Avi-tagged Ebola GPΔmuc trimer, termed GPΔmuc-$WL^2P^2$-1TD0-Avi-Biot, obtained from a HiLoad Superdex 200 16/600 column. 1TD0 is a trimeric scaffold used to stabilize GPΔmuc in a trimeric state and to deselect B cells directed to foldon in the two trimer groups. (B) Summary of Ebola GPΔmuc-specific bulk sorting of mouse splenic B cells from five vaccine groups. (C) Antibodyomics analysis of NGS data obtained for Ebola GPΔmuc-specific mouse splenic B cells. Distribution of critical B-cell properties are shown for three vaccine groups, in which mice were immunized with (D) GPΔmuc-foldon, (E) GPΔmuc-$WL^2P^2$-5GS-FR, and (F) GPΔmuc-$WL^2P^2$-10GS-I3-01v9-L7P. For each group, distributions are shown for germline VH/VK gene usage (top), germline VH/VK divergence (bottom left) and CDRH/K3 loop length (bottom right).

Previously, we combined antigen-specific B cell sorting and NGS to obtain a quantitative readout of B cell responses induced by HCV E2 core (E2mc3) and E2mc3-E2p NP (He et al., Sci. Adv. 6: eaaz6225, 2020). Diverse heavy-chain variable gene ($V_H$) usage, a higher degree of $V_H$ mutations, and a broader range of heavy chain complementarity determining region 3 (HCDR3) length were observed for E2p, alluding to a common B cell mechanism for effective NP vaccines. Can this mechanism be generalized to EBOV NP vaccines? Here, we applied the same strategy to obtain GP-specific B cell response profiles for different EBOV vaccine platforms. We first created an Avi-tagged GPΔmuc-WL$^2$P$^2$-1TD0 trimer probe to sort GP-specific mouse splenic B cells (FIG. 7A). Sorted B cells from 25 mice (FIG. 7B), five per group, were subjected to NGS on Ion GeneStudio S5. The NGS data were analyzed by a mouse Antibodyomics pipeline (FIG. 7C). Detailed B cell profiles were derived to facilitate the comparison of different vaccine platforms (FIG. 7D-F).

We mainly focused on the GPΔmuc-WL$^2$P$^2$-foldon group and the multilayered E2p group to compare B cell responses induced by GPΔmuc in its soluble form versus NP-displayed form. In terms of germline gene usage, similar patterns were observed for $V_H$ and $V_K$ genes. Namely, the stabilized GPΔmuc trimer activated more $V_H/V_L$ genes (9.4/9.4) than its NP form (6/7), with significant P values of 0.0163 and 0.0076 for $V_H$ and $V_L$, respectively. In contrast, the E2p NP decorated with 60 HCV E2 cores activated more $V_H$—but not $V_L$—genes than the E2 core. In terms of the degree of somatic hypermutation (SHM), no significant difference was found between the two groups. Nonetheless, the NP group showed a visible shift in the SHM distribution, with higher germline $V_H/V_K$ divergence, on average 6.4%/2.9%, than the trimer group, on average 5.3%/2.6%. In the HCDR3 analysis, two metrics—the average loop length and the r.m.s. fluctuation (r.m.s.f) of loop length—were calculated for comparison. Unlike in the HCV vaccine study where HCDR3 r.m.s.f. yielded a P value of <0.0001 between the E2 core and NP groups, no significant difference was found between the EBOV trimer and NP groups, although the E2p-L4P NP induced antibodies with longer HCDR3 loops. Overall, EBOV and HCV NPs demonstrated differential B cell patterns with respect to individual antigens. There were no apparent correlations between B cell profiles and vaccine-induced NAb/c13C6-like responses. Our results suggest that antigen size, structure, glycosylation, and epitope distribution, other than the multivalent NP display, may also be critical to shaping the B cell response.

Example 9 Some Exemplified Materials and Methods

Expression and purification of EBOV GPΔmuc and GPΔmuc-presenting NPs: Wildtype and redesigned GPΔmuc constructs were transiently expressed in HEK293 F cells (Thermo Fisher) for biochemical, biophysical, and antigenic analyses. Briefly, 293 F cells were thawed and incubated with FreeStyle™ 293 Expression Medium (Life Technologies, CA) in a shaker incubator at 37° C., 135 rpm and 8% $CO_2$. When the cells reached a density of $2.0 \times 10^6$/ml, expression medium was added to reduce cell density to $1.0 \times 10^6$ ml$^{-1}$ for transfection with polyethyleneimine (PEI) (Polysciences, Inc). Next, 900 μg of plasmid in 25 ml of Opti-MEM transfection medium (Life Technologies, CA) was mixed with 5 ml of PEI-MAX (1.0 mg/ml) in 25 ml of Opti-MEM. After 30-min incubation, the DNA-PEI-MAX complex was added to 1 L 293 F cells. Culture supernatants were harvested five days after transfection, clarified by centrifugation at 2200 rpm for 22 min, and filtered using a 0.45 μm filter (Thermo Scientific). GPΔmuc proteins were extracted from the supernatants using an mAb114 antibody column or an mAb100 antibody column. Bound proteins were eluted three times, each with 5 ml of 0.2 M Glycine (pH=2.2) and neutralized with 0.5 ml of Tris-Base (pH=9.0). The proteins were further purified by size exclusion chromatography (SEC) on a Superdex 200 Increase 10/300 GL column or a HiLoad Superdex 200 16/600 column (GE Healthcare). GPΔmuc-presenting nanoparticles were produced in ExpiCHO cells (Thermo Fisher). Briefly, ExpiCHO cells were thawed and incubated with ExpiCHO™ Expression Medium (Thermo Fisher) in a shaker incubator at 37° C., 135 rpm and 8% $CO_2$. When the cells reached a density of $10 \times 10^6$ ml$^{-1}$, ExpiCHO™ Expression Medium was added to reduce cell density to $6 \times 10^6$ ml$^{-1}$ for transfection. The ExpiFectamine™ CHO/plasmid DNA complexes were prepared for 100-ml transfection in ExpiCHO cells following the manufacturer's instructions. For these nanoparticle constructs, 100 μg of plasmid and 320 μl of ExpiFectamine™ CHO reagent were mixed in 7.7 ml of cold OptiPRO™ medium (Thermo Fisher). After the first feed on day one, ExpiCHO cells were cultured in a shaker incubator at 33° C., 115 rpm and 8% $CO_2$ following the Max Titer protocol with an additional feed on day five (Thermo Fisher). Culture supernatants were harvested 13 to 14 days after transfection, clarified by centrifugation at 4000 rpm for 25 min, and filtered using a 0.45 μm filter (Thermo Fisher). The mAb100 antibody column was used to extract nanoparticles from the supernatants, which was followed by SEC on a Superose 6 10/300 GL column. For GPΔmuc and GPΔmuc-presenting nanoparticles, protein concentration was determined using $UV_{280}$ absorbance with theoretical extinction coefficients.

Blue Native Polyacrylamide Gel Electrophoresis (BN-PAGE): EBOV GPΔmuc and GPΔmuc-presenting nanoparticles were analyzed by blue native polyacrylamide gel electrophoresis (BN-PAGE) and stained with Coomassie blue. The proteins were mixed with sample buffer and G250 loading dye and added to a 4-12% Bis-Tris NativePAGE™ gel (Life Technologies). BN-PAGE gels were run for 2 to 2.5 hours at 150 V using the NativePAGE™ running buffer (Life Technologies) according to the manufacturer's instructions.

Enzyme-Linked Immunosorbent Assay (ELISA): Each well of a Costar™ 96-well assay plate (Corning) was first coated with 50 μl PBS containing 0.2 μg of the appropriate antigens. The plates were incubated overnight at 4° C., and then washed five times with wash buffer containing PBS and 0.05% (v/v) Tween 20. Each well was then coated with 150 μl of a blocking buffer consisting of PBS, 40 mg ml$^{-1}$ blotting-grade blocker (Bio-Rad), and 5% (v/v) FBS. The plates were incubated with the blocking buffer for 1 hour at room temperature, and then washed five times with wash buffer. For antigen binding, antibodies were diluted in the blocking buffer to a maximum concentration of 10 μg ml⁻¹ followed by a 10-fold dilution series. For each antibody dilution, a total of 50 μl volume was added to the appropriate wells. For animal sample analysis, serum or plasma was diluted by 10-fold for mouse and 50-fold for rabbit in the blocking buffer and subjected to a 10-fold dilution series. For each sample dilution, a total of 50 μl volume was added to the wells. Each plate was incubated for 1 hour at room temperature, and then washed 5 times with PBS containing 0.05% Tween 20. For antibody binding, a 1:5000 dilution of goat anti-human IgG antibody (Jackson ImmunoResearch Laboratories, Inc), or for animal sample analysis, a 1:2000 dilution of horseradish peroxidase (HRP)-labeled goat anti-mouse or anti-rabbit IgG antibody (Jackson ImmunoResearch Laboratories), was then made in the wash buffer (PBS containing 0.05% Tween 20), with 50 μl of this diluted secondary antibody added to each well. The plates were incubated with the secondary antibody for 1 hour at room temperature, and then washed 5 times with PBS containing 0.05% Tween 20. Finally, the wells were developed with 50 μl of TMB (Life Sciences) for 3-5 min before stopping the reaction with 50 μl of 2 N sulfuric acid. The resulting plate readouts were measured at a wavelength of 450 nm. Of note, the week 2 serum binding did not reach the plateau (or saturation) to allow for accurate determination of $EC_{50}$ titers. Nonetheless, the $EC_{50}$ values calculated in Prism were used as a quantitative measure of antibody titers to facilitate the comparison of different vaccine groups at week 2.

Bio-Layer interferometry (BLI): The kinetics of GPΔmuc and GPΔmuc-presenting nanoparticle binding to a panel of 10 antibodies was measured using an Octet Red96 instrument (fortéBio, Pall Life Sciences). All assays were performed with agitation set to 1000 rpm in fortéBio 1×kinetic buffer. The final volume for all the solutions was 200 μl per well. Assays were performed at 30° C. in solid black 96-well plates (Geiger Bio-One). 5 μg ml⁻¹ of antibody in 1×kinetic buffer was loaded onto the surface of anti-human Fc Capture Biosensors (AHC) for GPΔmuc and of anti-human Fc Quantitation Biosensors (AHQ) for nanoparticles for 300 s. A 60 s biosensor baseline step was applied prior to the analysis of the association of the antibody on the biosensor to the antigen in solution for 200 s. A two-fold concentration gradient of antigen, starting at 400 nM for GPΔmuc trimers, 25 nM for FR NP, and 10 for E2p/I3-01v9 NPs was used in a titration series of six. The dissociation of the interaction was followed for 300 s. Correction of baseline drift was performed by subtracting the mean value of shifts recorded for a sensor loaded with antibody but not incubated with antigen and for a sensor without antibody but incubated with antigen. Octet data were processed by FortéBio's data acquisition software v.8.1. Experimental data were fitted with the binding equations describing a 2:1 interaction to achieve optimal fitting. Of note, GPΔmuc trimer binding was also measured using AHQ to facilitate the comparison of antibody binding with nanoparticles.

Differential scanning calorimetry (DSC): Thermal melting curves of WT and redesigned GPΔmuc trimers were obtained with a MicroCal VP-Capillary calorimeter (Malvern). The purified GPΔmuc produced from 293F cells were buffer exchanged into 1×PBS and concentrated to 27-50 μM before analysis by the instrument. Melting was probed at a scan rate of 90° C.·h⁻¹ from 25° C. to 110° C. Data processing, including buffer correction, normalization, and baseline subtraction, was conducted using the standardized protocol from the Origin 7.0 software.

Protein production, crystallization and data collection: Two Zaire EBOV GPΔmuc-foldon constructs, one with the W615L mutation and the L extension (to aa 637) and the other with an additional T577P mutation, were expressed in HEK293 S cells. The expressed GP was purified using an mAB100 antibody column followed by size-exclusion chromatography (SEC) on a HiLoad Superdex 200 16/600 column (GE Healthcare). The freshly purified samples of GP were used for crystallization. The crystallization experiments were carried out using the sitting drop vapor diffusion method on an automated CrystalMation™ robotic system (Rigaku) at both 4° C. and 20° C. at The Scripps research Institute (TSRI) (Elsliger et al., *Acta Crystallogr. Sect. F Struct. Biol. Cryst. Commun.* 66, 1137-1142, 2010). EBOV GP was concentrated to ~10 mg/ml in 50 mM Tris-HCl pH 8.0. The reservoir solution contained 12% (w/v) PEG 6000 and 0.1 M Sodium citrate, pH 4.5. The diffractable crystals were obtained after two weeks at 20° C. The crystals of EBOV GP were cryoprotected with 25% glycerol, mounted in a nylon loop and flash frozen in liquid nitrogen. The data were collected for two crystals of GPΔmuc-WL²-foldon and GPΔmuc-WL²P²-foldon at Advanced Photon Source (APS) beamline 23IDB, which were diffracted to 2.3 Å and 3.2 Å resolution, respectively. The diffraction data sets were processed with HKL-2000. Crystals belonged to rhombohedral H32 and tetragonal P321 space groups with cell dimensions of GPΔmuc-WL²-foldon a=114.58 Å, b=114.58 Å and c=312.38 Å and GPΔmuc-WL²P²-foldon a=114.06 Å, b=114.06 Å and c=136.22 Å, respectively. The overall completeness of the two data sets was 95.77% and 99%, respectively.

Structure determination and refinement: The structures of EBOV GP were determined by molecular replacement (MR) using Phaser from the CCP4i suite with the coordinates of Zaire Ebola GP (PDB: 5JQ3) and the program MOLREP. The polypeptide chains were manually adjusted into electron density using Coot, with structure validation carried out using MolProbity. The final $R_{cryst}$ and $R_{free}$ values for the refined structures are 19.2% and 22.9% and 25% and 29.3 for GPΔmuc-WL²-foldon and GPΔmuc-WL²P²-foldon, respectively. The data processing and refinement parameters are listed in table S1.

Electron microscopy (EM) assessment of nanoparticle constructs: The initial EM assessment of EBOV GPΔMuc nanoparticles was conducted at the Scripps Core Microscopy Facility. Briefly, nanoparticle samples were prepared at the concentration of 0.01 mg/ml. Carbon-coated copper grids (400 mesh) were glow-discharged and 8 μL of each sample was adsorbed for 2 minutes. Excess sample was wicked away and grids were negatively stained with 2% uranyl formate for 2 minutes. Excess stain was wicked away and the grids were allowed to dry. Samples were analyzed at 80 kV with a Talos L120C transmission electron microscope (Thermo Fisher) and images were acquired with a CETA 16M CMOS camera.

Mouse immunization and sample collection: The Institutional Animal Care and Use Committee (IACUC) guidelines were followed with animal subjects tested in the immunization study. Eight-week-old BALB/c mice were purchased from The Jackson Laboratory. Mice were housed in ventilated cages in environmentally controlled rooms at Scripps Research, in compliance with an approved IACUC protocol and AAALAC guidelines. Mice were immunized at weeks 0, 3, 6 and 9 for a total of four times. Each immunization consisted of 200 μl of antigen/adjuvant mix containing 50 μg of vaccine antigen (or 20 μg for the I3-01v9 NP) and 100 μl of adjuvant, AddaVax or Adju-Phos (InvivoGen), via the intraperitoneal (i.p.) route. Blood was collected two weeks after each immunization. All bleeds were performed through the facial vein (submandibular bleeding) using lancets (Goldenrod). While intermediate bleeds were collected without anticoagulant, terminal bleeds were collected using EDTA-coated tubes. Serum and plasma were heat inactivated at 56° C. for 30 min, spun at 1000 RPM for 10 min, and sterile filtered. The cells were washed once in PBS and then resuspended in 1 ml of ACK Red Blood Cell lysis buffer (Lonza). After two rounds of washing with PBS, peripheral blood mononuclear cells (PBMCs) were resuspended in 2 ml of Bambanker Freezing Media (Lymphotec). In addition, spleens were also harvested and grounded against a 70-μm cell strainer (BD Falcon) to release the splenocytes into a cell suspension. Splenocytes were centrifuged, washed in PBS, treated with 5 ml of Red Blood Cell Lysis Buffer Hybri-Max (Sigma-Aldrich), and frozen with 10% of DMSO in FBS. While serum and plasma were used in EBOV neutralization assays, 80% of the plasma from individual mice at week 11 was purified using a 0.2-ml protein G spin kit (Thermo Scientific) following the manufacturer's instructions. Purified mouse IgGs at week 11 (w11) were assessed in pseudovirus neutralization assays. Rabbit immunization and blood sampling were carried out under a subcontract at ProSci (San Diego, Calif.). Five groups of female New Zealand White rabbits, four rabbits per group, were immunized intramuscularly (i.m.) with 50 μg (20 μg for the I3-01v9 NP) of vaccine antigen formulated in 250 μl of adjuvant, AddaVax or Adju-Phos (InvivoGen), with a total volume of 500 μl, at weeks 0, 3, 6, and 9. Blood samples, 20 ml each time, were collected from the auricular artery at day 0 (Pre), weeks 2, 5, 8, and 11. For the last time point (week 13), more than 100 ml of blood was taken via cardiac puncture. Serum was separated from blood and heat inactivated for ELISA binding assays. Purified rabbit IgGs were assessed in pseudovirus neutralization assays.

Pseudovirus neutralization assay: Ebolavirus pseudoviral particle (Ebolavirus-pp) neutralization assays were utilized to assess the neutralizing activity of previously reported mAbs and vaccine-induced antibody responses in mice and rabbits. Ebolavirus-pps were generated by co-transfection of HEK293 T cells with the pNL4-3.lucR-E-plasmid (NIH AIDS reagent program) and the expression plasmid encoding the GP gene of an EBOV Makona strain (GenBank Accession number: KJ660346) or a BDBV Uganda strain (GenBank Accession number: KR063673) at a 4:1 ratio by lipofectamine 3000 (Thermo Fisher Scientific). After 48 to 72 h, Ebolavirus-pps were collected from the supernatant by centrifugation at 4000 rpm for 10 min, aliquoted, and stored at −80° C. before use. The mAbs at a starting concentration of 10 μg/ml, or purified IgGs at a starting concentration 300 μg/ml for mouse and 1000 μg/ml for rabbit, were mixed with the supernatant containing Ebolavirus-pps and incubated for 1 h at 37° C. in white solid-bottom 96-well plate (Corning). Based on recent studies on EBOV infectivity in various cell lines, HEK293 T cells or TZM-bl cells were used for Ebolavirus-pp neutralization assays. Briefly, HEK293 T cells or TZM-bl cells at $1\times10^4$ were added to each well and the plate was incubated at 37° C. for 48 h. After incubation, overlying media was removed, and cells were lysed. The firefly luciferase signal from infected cells was determined using Bright-Glo Luciferase Assay System (Promega) according to the manufacturer's instructions. Data were retrieved from a BioTek microplate reader with Gen 5 software, the average background luminescence from a series of uninfected wells was subtracted from each well, and neutralization curves were generated using GraphPad Prism 8.4.3, in which values from wells were compared against a well containing Ebolavirus-pp only. Lentiviral vectors pseudotyped with the murine leukemia virus (MLV) Env gene, termed MLV-pps, were produced in HEK293 T cells and included in the neutralization assays as a negative control. As non-NAb c13C6 exhibited enhanced MLV-pp infection, the MLV-pp assay was also used to detect the c13C6-like, ADE-causing antibody response in immunized animal samples.

Bulk sorting of EBOV GPΔmuc-specific mouse B cells: Spleens were harvested from immunized mice 15 days after the last immunization and cell suspension was prepared. Cells were stained as follows: dead cells were excluded by staining with Fixable Aqua Dead Cell Stain kit (Thermo Fisher L34957). Receptors FcγIII (CD16) and FcγII (CD32) were blocked by adding 20 μl of 2.4G2 mAb (BD Pharmigen N553142). Cells were then incubated with 10 μg/ml of biotinylated GPΔmuc, WT or UFOg$^2$. Briefly, GPΔmuc was generated by biotinylation of the individual Avi-tagged EBOV GPΔmuc using biotin ligase BirA according to the manufacturer's instructions (Avidity LLC). Biotin excess was removed by SEC on a HiLoad Superdex 200 16/600 column (GE Healthcare). In the SEC profile, the Avi-tagged GPΔmuc peak is centered at 14.5 ml, while a broader peak of biotin ligase can be found at 65-70 ml (WT) or 60-65 ml (UFOg$^2$). Cells and biotinylated proteins were incubated for 5 min at 4° C., followed by the addition of 2.5 μl of anti-mouse IgG fluorescently labeled with FITC (Jackson ImmunoResearch 115-095-071) and incubated for 15 min at 4° C. Finally, 5 μl of premium-grade allophycocyanin (APC)-labeled streptavidin were added to the cells and incubated for 15 min at 4° C. In each step, cells were washed with DPBS and the sorting buffer was 0.5 ml FACS buffer. $FITC^+$ $APC^+$ GPΔmuc-specific B cells were sorted using BD FACSAria II into Eppendorf tube with 500 μl of FACS buffer.

Next-generation sequencing (NGS) and Bioinformatics Analysis of Mouse B cells: A 5'-rapid amplification of cDNA ends (RACE) protocol has been reported for unbiased sequencing of mouse B cell repertoires. Here, this protocol was applied to bulk-sorted, E2-specific mouse splenic B cells. Briefly, 5'-RACE cDNA was obtained from bulk-sorted splenic B cells of each mouse with SMART-Seq v4 Ultra Low Input RNA Kit for Sequencing (TaKaRa). The immunoglobulin PCRs were set up with Platinum Taq High-Fidelity DNA Polymerase (Life Technologies) in a total volume of 50 μl, with 5 μl of cDNA as template, 1 μl of 5'-RACE primer, and 1 μl of 10 μM reverse primer. The 5'-RACE primer contained a PGM/S5 P1 adaptor, while the reverse primer contained a PGM/S5 A adaptor. We adapted the mouse 3'-$C_\gamma$1-3/3'-$C_\mu$ inner primers and 3'-$mC_\kappa$ outer primer as reverse primers for 5'-RACE PCR processing of heavy and light (κ) chains. A total of 25 cycles of PCR was performed and the expected PCR products (500-600 bp) were gel purified (Qiagen). NGS was performed on the Ion S5 GeneStudio system. Briefly, heavy and light (κ) chain libraries from the same mouse were quantitated using Qubit® 2.0 Fluorometer with Qubit® dsDNA HS Assay Kit, and then mixed using a ratio of 3:1 before being pooled with antibody libraries of other mice at an equal ratio for sequencing. Template preparation and (Ion 530) chip loading were performed on Ion Chef using the Ion 520/530 Ext Kit, followed by sequencing on the Ion S5 system with default settings. The mouse Antibodyomics pipeline was used to process the raw data and determine distributions for germline gene usage, somatic hypermutation (SHM), germline divergence, and H/KCDR3 loop length.

The invention thus has been disclosed broadly and illustrated in reference to representative embodiments described above. It is understood that various modifications can be made to the present invention without departing from the spirit and scope thereof.

It is further noted that all publications, sequence accession numbers, patents and patent applications cited herein are hereby expressly incorporated by reference in their entirety and for all purposes as if each is individually so denoted. Definitions that are contained in text incorporated by reference are excluded to the extent that they contradict definitions in this disclosure.

What is claimed is:

1. An engineered Ebolavirus glycoprotein (GP) protein, comprising (a) substitution of residue W615 in heptad repeat 2 (HR2) with residue L, A, V, I or F, and (b) one or more proline substitutions in heptad repeat 1 C segment (HR1$_C$); wherein the amino acid numbering is based on Zaire Ebolavirus GP sequence with UniProt ID Q05320 (SEQ ID NO:1).

2. The engineered Ebolavirus GP protein of claim 1, wherein the Ebolavirus is Zaire Ebolavirus (EBOV), Sudan virus (SUDV), Taï forest virus (TAFV), Bundibugyo virus (BDBV), or Reston Ebolavirus (RESTV).

3. The engineered Ebolavirus GP protein of claim 1, wherein the proline substitutions comprise T577P or L579P.

4. The engineered Ebolavirus GP protein of claim 1, further comprising a truncation at the C-terminus of the membrane proximal external region (MPER).

5. The engineered Ebolavirus GP protein of claim 4, further comprising (a) a deletion of the mucin-like domain (MLD) deleted from the GP1 subunit, and/or (b) a deletion of MPER from the GP2 subunit.

6. An engineered Ebolavirus glycoprotein (GP) protein, comprising: (a) a truncated soluble GP of an Ebolavirus that has the mucin-like domain (MLD) deleted from the GP1 subunit and the membrane proximal external region (MPER) deleted from the GP2 subunit, and (b) substitution of residue W615 in heptad repeat 2 (HR2) with residue L, A, V, I or F; wherein the amino acid numbering is based on Zaire Ebolavirus GP sequence corresponding to UniProt ID Q05320 (SEQ ID NO:1).

7. The engineered Ebolavirus GP protein of claim 6, further comprising one or more modifications selected from (i) an extension of HR2 at the C terminus, (ii) one or more proline substitutions in heptad repeat 1 C segment (HR1$_C$), and (iii) one or more engineered inter-GP disulfide bonds.

8. The engineered Ebolavirus GP protein of claim 6, wherein the truncated soluble GP comprises SEQ ID NO:2 or SEQ ID NO:3, or a variant thereof with at least 99% sequence identity.

9. The engineered Ebolavirus GP protein of claim 6, comprising the sequence SEQ ID NO:4, or a variant thereof with at least 99% sequence identity.

10. The engineered Ebolavirus GP protein of claim 6, further comprising an extension of HR2 at the C-terminus.

11. The engineered Ebolavirus GP protein of claim 10, wherein the HR2 extension comprises (a) extending HR2 C terminus with a N-terminal fragment of the adjacent membrane proximal external region (MPER) of the Ebolavirus glycoprotein or (b) replacing a HR2 C-terminal fragment with a longer leucine zipper motif.

12. The engineered Ebolavirus GP protein of claim 10, wherein the HR2 extension comprises (a) extending the HR2 C terminus from residue 632 to residue 637 in MPER, (b) extending the HR2 C terminus from residue 632 to residues 643 in MPER, or (c) replacing residues 617-632 with a GCN4 leucine zipper sequence shown in SEQ ID NO:34.

13. The engineered Ebolavirus GP protein of claim 10, wherein the W615 substitution comprises W615L substitution or P612G/W615F double mutation.

14. The engineered Ebolavirus GP protein of claim 10, comprising (a) W615L substitution and (b) extension of the HR2 C terminus from residue 632 to residue 637 in MPER of the Ebolavirus GP.

15. The engineered Ebolavirus GP protein of claim 10, comprising (a) P612G/W615F double mutation in HR2 and (b) replacement of residues 617-632 with a GCN4 leucine zipper sequence shown in SEQ ID NO:34.

16. The engineered Ebolavirus GP protein of claim 10, comprising an amino acid sequence as set forth in any one of SEQ ID NOs:5-8, or a variant thereof with at least 99% sequence identity.

17. The engineered Ebolavirus GP protein of claim 10, further comprising a C-terminal trimerization motif.

18. The engineered Ebolavirus GP protein of claim 17, wherein the C-terminal trimerization motif comprises SEQ ID NO:29 or SEQ ID NO:30, or a variant thereof with at least 99% sequence identity.

19. The engineered Ebolavirus GP protein of claim 6, further comprising one or more proline substitutions in the $HR1_C$ segment.

20. The engineered Ebolavirus GP protein of claim 19, comprising an amino acid sequence as set forth in any one of SEQ ID NOs:9-17 and 20, or a variant thereof with at least 99% sequence identity.

21. The engineered Ebolavirus GP protein of claim 19, comprising (a) W615L substitution, (b) proline substitution T577P or L579P, and (c) HR2 extension from residue 632 to residue 637 in MPER.

22. The engineered Ebolavirus GP protein of claim 19, further comprising a C-terminal trimerization motif.

23. The engineered Ebolavirus GP protein of claim 6, further comprising an engineered disulfide bond between two neighboring GP protomers.

24. The engineered Ebolavirus GP protein of claim 23, wherein the engineered disulfide bond is engineered between residues G91/A575 (SS2), F153/Y534 (SS1), T520/A575 (SS3), G157/I532 (SS4), D522/A575 (SS5) or K56/G599 (SS6).

25. A pharmaceutical composition, comprising the engineered Ebolavirus GP protein of claim 6, and a pharmaceutically acceptable carrier.

26. A vaccine composition, comprising an engineered Ebolavirus GP protein of claim 6 that is displayed on the surface of a self-assembling nanoparticle.

27. The vaccine composition of claim 26, comprising (1) a polypeptide sequence containing from N terminus to C terminus (a) the engineered Ebolavirus GP protein, linker sequence G4S (SEQ ID NO:43), nanoparticle sequence ferritin, (b) the engineered Ebolavirus GP protein, linker sequence $G_4S$ (SEQ ID NO:43), nanoparticle sequence E2p, or (c) the engineered Ebolavirus GP protein, linker sequence $(G_4S)_2$ (SEQ ID NO:42), nanoparticle sequence I3-01v9; wherein the engineered Ebolavirus GP protein comprises W615L substitution, proline substitution T577P, and HR2 extension from residue 632 to residue 637 in MPER.

28. The vaccine composition of claim 27, further comprising a locking domain and/or a T-cell epitope that is fused to the C-terminus of the nanoparticle subunit sequence.

29. The vaccine composition of claim 28, comprising (1) a polypeptide sequence containing from N-terminus to C-terminus (a) the engineered Ebolavirus GP protein shown in SEQ ID NO:17, nanoparticle subunit sequence shown in SEQ ID NO:36 (E2p), locking domain shown in SEQ ID NO:39 (LD4), and T cell epitope shown in SEQ ID NO:31 or (b) the engineered Ebolavirus GP protein shown in SEQ ID NO:17, nanoparticle sequence shown in SEQ ID NO:37 (I3-01v9), locking domain shown in SEQ ID NO:40 (LD7), or (2) a variant of the polypeptide sequence with at least 99% sequence identity.

* * * * *

UNITED STATES PATENT AND TRADEMARK OFFICE
CERTIFICATE OF CORRECTION

| | |
|---|---|
| PATENT NO. | : 11,305,004 B2 |
| APPLICATION NO. | : 17/397340 |
| DATED | : April 19, 2022 |
| INVENTOR(S) | : He et al. |

It is certified that error appears in the above-identified patent and that said Letters Patent is hereby corrected as shown below:

In the Specification

Column 1, Line 15, replace the paragraph with the paragraph below:
-- This invention was made with government support under grant numbers AI129698, AI123861, AI140844 and AI124337 awarded by the National Institutes of Health. The government has certain rights in the invention. --

Signed and Sealed this
Sixth Day of December, 2022

*Katherine Kelly Vidal*

Katherine Kelly Vidal
*Director of the United States Patent and Trademark Office*